US008846052B2

(12) United States Patent
Sawada et al.

(10) Patent No.: US 8,846,052 B2
(45) Date of Patent: Sep. 30, 2014

(54) BACTERIAL TOXIN VACCINE

(75) Inventors: Kazutoshi Sawada, Sodegaura (JP); Kazuya Yoshida, Ikoma (JP); Mayumi Yoshida, legal representative, Nara (JP); Nobuo Yoshida, legal representative, Nishinomiya (JP); Kyoko Yoshida, legal representative, Nishinomiya (JP); Takeshi Matsui, Ikoma (JP)

(73) Assignees: Idemitsu Kosan Co., Ltd., Tokyo (JP); National University Corporation Nara Institute of Science and Technology, Ikoma-shi (JP)

( * ) Notice: Subject to any disclaimer, the term of this patent is extended or adjusted under 35 U.S.C. 154(b) by 596 days.

(21) Appl. No.: 12/990,597

(22) PCT Filed: Apr. 28, 2009

(86) PCT No.: PCT/JP2009/058345
§ 371 (c)(1),
(2), (4) Date: Nov. 1, 2010

(87) PCT Pub. No.: WO2009/133882
PCT Pub. Date: Nov. 5, 2009

(65) Prior Publication Data
US 2011/0231960 A1 Sep. 22, 2011

(30) Foreign Application Priority Data
May 2, 2008 (JP) ................................. 2008-120573

(51) Int. Cl.
A61K 39/02 (2006.01)
C07K 19/00 (2006.01)
A01H 5/00 (2006.01)
C12N 15/62 (2006.01)
C12N 15/82 (2006.01)
C12N 15/66 (2006.01)
A61K 39/108 (2006.01)
C07K 14/25 (2006.01)
C07K 14/245 (2006.01)
A61K 39/00 (2006.01)

(52) U.S. Cl.
CPC ....... *C12N 15/8258* (2013.01); *A61K 2039/517* (2013.01); *A61K 39/0258* (2013.01); *C07K 14/25* (2013.01); *C07K 14/245* (2013.01); *A61K 39/00* (2013.01); *C07K 2319/55* (2013.01)
USPC .................... 424/192.1; 435/69.7; 424/241.1; 424/194.1; 424/236.1; 800/295; 800/288

(58) Field of Classification Search
None
See application file for complete search history.

(56) References Cited

U.S. PATENT DOCUMENTS

2008/0107653 A1  5/2008  Vermeij
2011/0002950 A1  1/2011  Sawada et al.

FOREIGN PATENT DOCUMENTS

EP       0863211 A1 *  9/1998  ............. C12N 15/62
WO    WO 01/89456 A3     11/2001
WO    WO 2005/011733 A1  2/2005

OTHER PUBLICATIONS

O'Dowd et al, Vaccine 17:1442-1453, 1999.*
O'Dowd et al (Vaccine, 17, p. 1442-1453, 1999).*
Faye et al (Vaccine, 23, p. 1770-1778, 2005).*
George et al (Protein Engineering, 15(11), p. 871-879, 2003).*
Jin et al (J Immunol, 180, p. 58-63, 2008).*
Schmidt (see UniProt accession Q9MBZ7, entry date to UniProt Oct. 1, 2000).*
Satoh et al (J Biosci Bioeng, 98(1), p. 1-8, 2004).*
Limaye et al (FASEB J, 20(7), p. 959-961, 2006).*
Sawada K., et al., "Research and Development of Production of Proteins for Oral Vaccines for Livestock using Recombinant Lettuce," Biotechnology Symposium, pp. 28-31, (Nov. 6, 2007) (with English language translation).
Sawada K., et al., "Development of Technique for Producing Vaccine Components Using Lettuce," Preprints of Biotechnology Symposium, pp. 107-108, (Nov. 6, 2007) (with English language translation).
Matsui, T., et al., "Lettuce Vesicular Transport Engineering for Production of Vaccine Proteins for Pig Edema Disease," Abstract of the 25th Meeting and Symposium in CHIBA of the Japanese Association for Plant Tissue Culture, p. 180, (Aug. 8, 2007) (with English language translation).
Yasuda, H., et al., "The Correlation between Expression and Localization of a Foreign Gene Product in Rice Endosperm," Plant Cell Physiology, vol. 47, No. 6, pp. 756-763, (2006).
International Search Report issued Jun. 16, 2009 in PCT/JP09/058345 filed Apr. 28, 2009.
Office Communication pursuant to Article 94(3) EPC issued Jan. 16, 2012, in European Patent Application No. 09 738 819.3.
A.M. O'Dowd, et al., "Novel modifications to the C-terminus of LTB that facilitate site-directed chemical coupling of antigens and the development of LTB as a carrier for mucosal vaccines", Vaccine, Elsevier Ltd., vol. 17, No. 11-12, XP004158272, Mar. 1, 1999, pp. 1442-1453.

(Continued)

*Primary Examiner* — Cathy Kingdon Worley
*Assistant Examiner* — Stephen Uyeno
(74) *Attorney, Agent, or Firm* — Oblon, Spivak, McClelland, Maier & Neustadt, L.L.P.

(57) ABSTRACT

A bacterial toxin protein such as a Shiga toxin protein is efficiently produced using plant cells. The plant cells are transformed using a DNA construct containing DNA encoding a hybrid protein in which the bacterial toxin proteins such as the Shiga toxin proteins are tandemly linked through a peptide having the following characteristics (A) and (B) to produce the bacterial toxin protein in the plant cells: (A) a number of amino acids is 12 to 30; and (B) a content of proline is 20 to 35%.

26 Claims, 23 Drawing Sheets

(56) References Cited

OTHER PUBLICATIONS

Malin Gustavsson, et al., "Stable linker peptides for a cellulose-binding domain-lipase fusion protein expressed in *Pichia pastoris*", Protein Engineering, vol. 14, No. 9, XP009118009, Sep. 1, 2001, pp. 711-715.

Liang Jin, et al., A Th1-Recognized Peptide P277, When Tandemly Repeated, Enhances a Th2 Immune Response toward Effective Vaccines against Autoimmune Diabetes in Nonobese Diabetic Mice, The Journal of Immunology, vol. 180, No. 1, XP009155180, Jan. 1, 2008, pp. 58-63 (with cover page and corrections page).

Jon Oscherwitz, et al., "A V3 loop haptenic peptide sequence, when tandemly repeated, enhances immunogenicity by facilitating helper T-cell responses to a covalently linked carrier protein", Vaccine, Elsevier Ltd., vol. 17, No. 19, XP004168970, May 14, 1999, pp. 2392-2399.

Extended Search Report issued May 20, 2011 in Europe Application No. 09738819.3.

Richard A. George, et al., "An analysis of protein domain linkers: their classification and role in protein folding", Protein Engineering, vol. 15, No. 11, 2003, pp. 871-879.

Xue Qin Ran, et al., "The immunogenicity of fusion protein linking the carboxyl terminus of the B subunit of Shiga toxin 2 to the B subunit of *E. coli* heat-labile enterotoxin", Vetrinary Microbiology, vol. 127, No. 1-2, 2008, pp. 209-215.

Xiang Gao, et al., "Immunogenicity of a novel Stx2B-Stx1B fusion protein in a mice model of Enterohemorrhagic *Escherichia coli* O157:H7 infection", Vaccine, vol. 27, No. 14, 2009, pp. 2070-2076.

Junko Satoh, et al., "The 5'-Untranslated Region of the Tobacco Alcohol Dehydrogenase Gene Functions as an Effective Translational Enhancer in Plant", Journal of Bioscience and Bioengineering, vol. 98, No. 1, 2004, pp. 1-8.

Hugh S. Mason, et al., "Edible Plant Vaccines: applications for prophylactic and therapeutic molecular medicine", Trends in Molecular Medicine, vol. 8, No. 7, Jul. 2002, pp. 324-329.

Takao Tsuji, et al., "A nasal vaccine comprising B-subunit derivative of Shiga toxin 2 for cross-protection against Shiga toxin types 1 and 2", Vaccine, vol. 26, No. 17, 2008, pp. 2092-2099.

Sharon X. Wen, et al., "A plant-based oral vaccine to protect against systemic intoxication by Shiga toxin type 2", Proceedings of the National Academy of Sciences of the United States of America, vol. 103, No. 18, May 2, 2006, pp. 7082-7087.

Takeshi Matsui, et al., "Production of double repeated B subunit of Shiga toxin 2e at high levels in transgenic lettuce plants as vaccine material for procine edema disease", Transgenic Res., Oct. 2010, 14 pages.

Takeshi Matsui, et al., "Transgenic Lettuce Producing a Candidate Protein for Vaccine against Edema Disease", Biosc. Biotechnol. Biochem., vol. 73, No. 7, 2009, pp. 1628-1634.

J. Recktenwald, et al., "Shiga toxin 2e B-subunit [Enterobacteria phage phiP27]", Genbank database, NP 543078, Jan. 19, 2002, 1 page.

A. P. M. Areas, et al., "Cholera toxin subunit B, partial [synthetic construct]", Genbank database, AAL01411.1, Aug. 20, 2002, 1 page.

\* cited by examiner

1 × Stx2eB-YFP

ADH | Stx2eB | PG | YFP | H HD
 | | 12 | | A E

2 × Stx2eB(PG12)-YFP

ADH | Stx2eB | PG | Stx2eB | PG | YFP | H HD
 | | 12 | | 11 | | A E

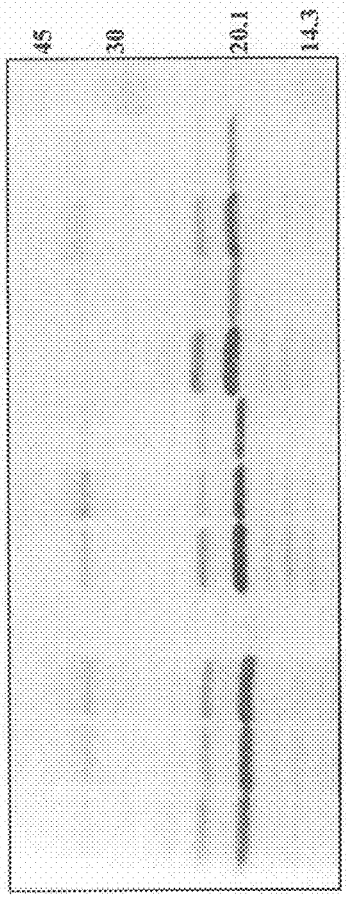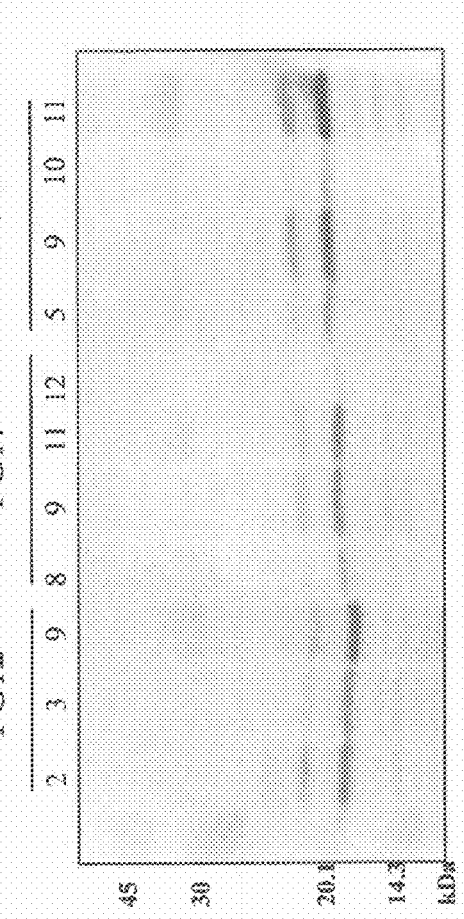
FIG. 22

BACTERIAL TOXIN VACCINE

The present application is a 35 U.S.C. §371 National Stage patent application of International patent application PCT/JP2009/058345, filed on Apr. 28, 2009, which claims priority to Japanese patent application JP 2008-120573, filed on May 2, 2008.

TECHNICAL FIELD

The present invention relates to a hybrid protein used for vaccines for diseases caused by bacterial toxins such as Shiga toxins, cholera toxins, and *Escherichia coli* heat-labile toxins, and a DNA construct for producing the hybrid protein.

BACKGROUND ART

Shiga toxins (Stxs, verotoxins) are proteinous exotoxins produced by enterohemorrhagic *Escherichia coli* of pathogenic *Escherichia coli* species. The Shiga toxins cause hemorrhagic enteritis, hemolytic uremic syndrome, encephalopathy, and the like.

The Shiga toxins are broadly classified into Stx1 and Stx2, each of which is further classified into subclasses. An example of the Stx2 includes Stx2e which causes swine edema disease. The swine edema disease is known to frequently occur in baby pigs one to two weeks after weaning. A fatality due to infection with edema disease bacteria is 50 to 90%, which is extremely high.

Further, cholera toxins (CTs) are proteinous exotoxins produced by *Vibrio cholerae*. The CTs are known to cause severe diarrhea and emesis.

Still further, *Escherichia coli* heat-labile toxins (LTs) are proteinous endotoxins produced by enterotoxigenic *Escherichia coli*. The LTs are known to cause diarrhea and emesis.

The bacterial toxins, Stxs, LTs, and CTs are all known to include a B-subunit pentamer involved in adhesion to cells and an A-subunit monomer having a toxicity. The LTs and the CTs are also known to be similar structurally and functionally.

As a method of preventing the diseases caused by those bacterial toxins, methods of administering a vaccine by an injection or a nasal spray and administering the vaccine orally are known.

For example, a technology where an attenuated Stx2e protein is produced using recombinant *Escherichia coli* and administered to pigs by an injection is known (Non-patent Document 1). However, for example, an amount of the attenuated Stx2e protein produced by the recombinant *Escherichia coli* is not sufficient and the administration of the vaccine by an injection requires human labor. This has been a problem.

Further, the method of administering the vaccine orally draws increasing attention in terms of reducing the labor in a stockbreeding field. In such a context, a technology where the bacterial toxin protein is produced by plants using a transgenic technology has been being developed. For example, a transgenic plant containing DNA encoding an LT protein B subunit (LTB) and expressing the DNA has been described (Patent Documents 1 and 2). A transgenic plant expressing DNA encoding the LT protein or the CT protein has been also described (Patent Document 3). However, there has been a problem that the amount of the produced protein is not sufficient in those technologies. An example of producing the LTB in *Lactuca sativa* has been reported (Non-patent Document 2). In this study, a gene of the LT protein B subunit including modified codons is expressed in *Lactuca sativa* using both a cauliflower mosaic virus 35S RNA promoter (CaMV35S) which is a promoter expressed highly in a plant and Kozak sequence which is an enhancer. As a result, it has been reported that the LT protein B subunit is accumulated in an amount of about 2.0% by mass of a total soluble protein of *Lactuca sativa*. However, this extent of the accumulated protein is thought to be insufficient to efficiently prevent a bacterial disease by utilizing the transgenic plant. That is, it is necessary to efficiently produce and accumulate the target bacterial toxin protein in plant cells.

The inventors of the present invention found that the Stx2e protein could be produced efficiently in a plant such as *Lactuca sativa* and accumulated at a high concentration in a plant body by expressing the Stx2e protein where a secretory signal peptide derived from a plant had been added to its amino terminus, using a 5'-untranslated region (ADH 5'-UTR) of an alcohol dehydrogenase gene derived from a plant, and filed the patent (Patent Document 4).

[Patent Document 1] JP 10-507916 A
[Patent Document 2] JP 2000-166411 A
[Patent Document 3] JP 2002-533068 A
[Patent Document 4] WO 2009/004842 A1
[Non-patent Document 1] Makino et al., Microbial Pathogenesis, Volume 31, Number 1, Jul. 2001, pp. 1-8(08)
[Non-patent Document 2] Kim et al., Protein Expression and Purification, Volume 51, Number 1, Jan. 2006, pp. 22-27 (06)

SUMMARY OF INVENTION

It is an object of the present invention to more efficiently produce a Stx protein and other bacterial toxin proteins having a conformation similar thereto using plant cells.

Through production of a hybrid protein in which two or three bacterial toxin proteins such as Stx2e and CT are tandemly linked through a peptide having a particular sequence in plant cells, the inventors of the present invention have succeeded in accumulating the bacterial toxin protein at a high concentration in the plant cells and completed the present invention.

The present invention is as follows.
(1) a hybrid protein, in which two or three of Shiga toxin proteins, cholera toxin proteins, or *Escherichia coli* heat-labile toxin proteins are each tandemly linked through a peptide having the following characteristics (A) and (B):
 (A) the number of amino acids is 12 to 30; and
 (B) the content of proline is 20 to 35%;
(2) the hybrid protein according to Item (1), in which the peptide further has the following characteristic (C):
 (C) proline is allocated every two or three amino acids;
(3) the hybrid protein according to Item (2), in which the peptide has an amino acid sequence represented by SEQ ID NO: 2, 82, or 84;
(4) the hybrid protein according to Item (3), in which two of the Shiga toxin proteins, cholera toxin proteins, or *Escherichia coli* heat-labile toxin proteins are tandemly linked through the peptide having the amino acid sequence represented by SEQ ID NO: 2;
(5) the hybrid protein according to any one of Items (1) to (4), in which the Shiga toxin proteins are Shiga toxin protein B subunits;
(6) the hybrid protein according to any one of Items (1) to (5), in which the Shiga toxin proteins are Stx2e proteins;
(7) the hybrid protein according to any one of Items (1) to (4), in which the cholera toxin proteins are cholera toxin protein B subunits;

(8) the hybrid protein according to Item (4), including an amino acid sequence represented by SEQ ID NO: 10, 12, 14, or 16;
(9) the hybrid protein according to Item (3), including an amino acid sequence represented by SEQ ID NO: 86, 88, 90, 92, 94, 96, 98, or 100;
(10) the hybrid protein according to any one of Items (1) to (9), in which a secretory signal peptide derived from a plant is added to its amino terminus;
(11) the hybrid protein according to Item (10), in which an endoplasmic reticulum retention signal peptide is added to its carboxyl terminus;
(12) the hybrid protein according to any one of Items (1) to (9), in which a chloroplast transit signal peptide is added to its amino terminus;
(13) a DNA construct, including DNA encoding the hybrid protein according to any one of Items (1) to (12);
(14) the DNA construct according to Item (13), including DNA having a base sequence represented by SEQ ID NO: 9, 11, 13, or 15;
(15) the DNA construct according to Item (13), including DNA having a base sequence represented by SEQ ID NO: 85, 87, 89, 91, 93, 95, 97, or 99;
(16) the DNA construct according to any one of Items (13) to (15), in which DNA encoding a hybrid protein is operably-linked to a 5'-untranslated region of an alcohol dehydrogenase gene derived from a plant;
(17) the DNA construct according to Item (16), in which the 5'-untranslated region of the alcohol dehydrogenase gene derived from the plant is derived from *Nicotiana tabacum;*
(18) a DNA construct according to Item (17), including a base sequence represented by any one of SEQ ID NOS: 24 to 29;
(19) a DNA construct according to Item (17), including a base sequence represented by any one of SEQ ID NOS: 101 to 111;
(20) a recombinant vector, including the DNA construct according to any one of Items (13) to (19);
(21) a transformant transformed with the recombinant vector according to Item (20);
(22) a transformant according to Item (21), in which the transformant is a transformed plant cell or a transformed plant;
(23) a seed, which is obtained from the transformant according to Item (21) or (22); and
(24) a peptide, having an amino acid sequence represented by SEQ ID NO: 2, 82, or 84.

BRIEF DESCRIPTION OF DRAWINGS

In the accompanying drawings.

DESCRIPTION OF EMBODIMENTS

Figure 1:
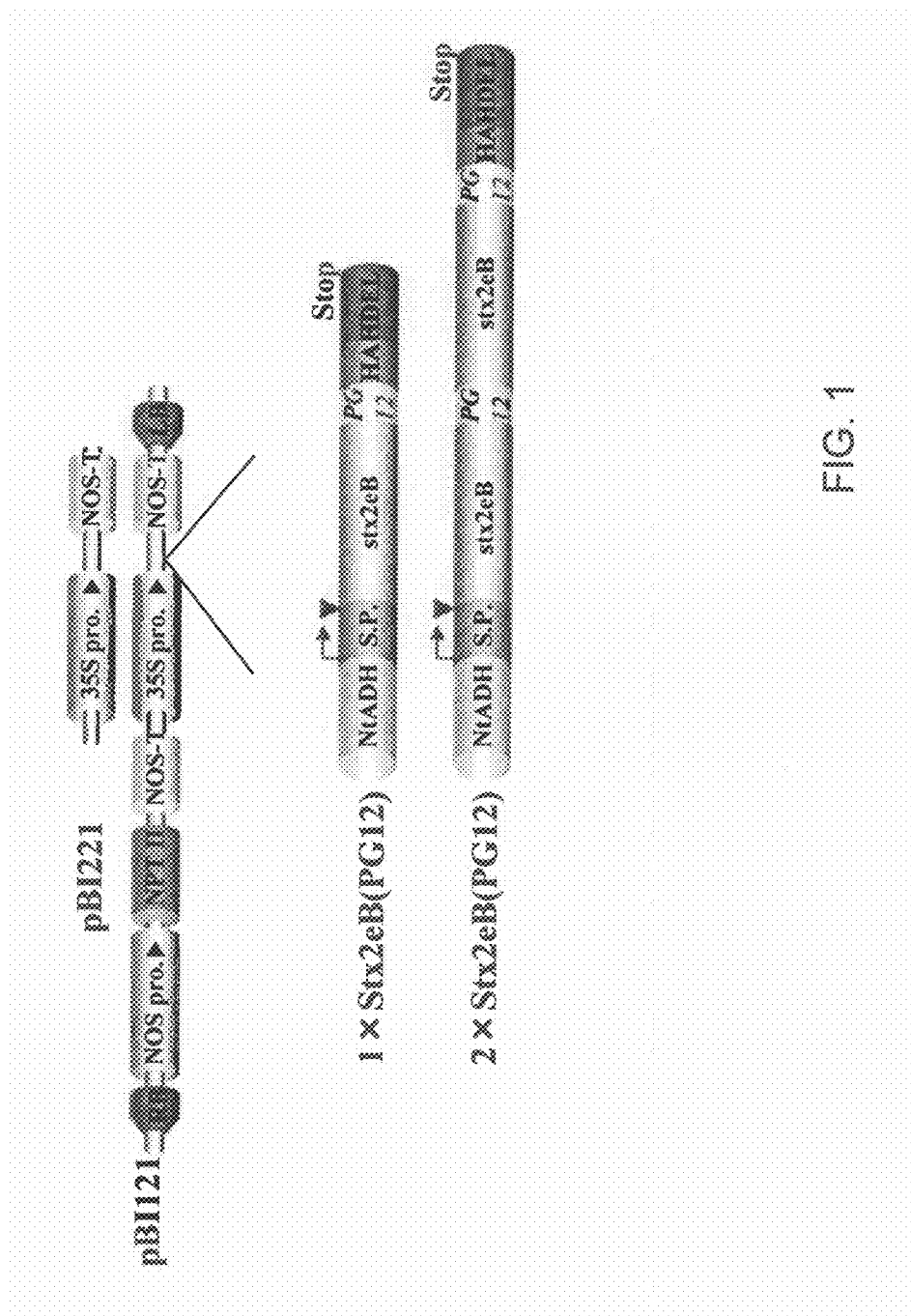
FIG. 1 is a view illustrating a design of Stx2eB expression vectors, in which an arrow denotes a translation initiation site, and an inverted triangle denotes a site to be cleaved after the transl

In a hybrid protein of the present invention, two or three of Shiga toxin (Stx) proteins, cholera toxin (CT) proteins, or *Escherichia coli* heat-labile toxin (LT) proteins are each tandemly linked through a peptide having the following characteristics (A) and (B):
(A) the number of amino acids is 12 to 30; and
(B) the content of proline is 20 to 35%.

Shiga toxins (Stxs) are classified into type 1 (Stx1) and type 2 (Stx2). The Stx1 is further classified into subclasses a to d, and the Stx2 is further classified into subclasses a to g, respectively. The Shiga toxin includes one A subunit which is a toxin main body and five B subunits involved in invasion into intestinal mucosa.

Of those, for example, Stx2e is known as a swine edema disease toxin, and its A subunit (Stx2eA) is represented by an amino acid sequence of SEQ ID NO: 4 and its B subunit (Stx2eB) is represented by an amino acid sequence of SEQ ID NO: 6.

In Stx2eA and Stx2eB, one or several amino acids may be substituted, deleted, inserted, or added in the amino acid sequences represented by SEQ ID NO: 4 or 6 as long as they can cause an immune response by administering to pigs. For example, the term "several" means the number of preferably 2 to 30, more preferably 2 to 20, and still more preferably 2 to 10, in Stx2eA, and means the number of preferably 2 to 10, more preferably 2 to 5, and still more preferably 2 to 3, in Stx2eB.

Further, Stx2eA and Stx2eB may be those having an identity of preferably 85% or more, more preferably 90% or more, and still more preferably 95% or more to the amino acid sequences represented by SEQ ID NOS: 4 and 6, and being capable of causing the immune response by administering to the pig.

The cholera toxin (CT) includes one A subunit (CTA) which is the toxin main body and five B subunits (CTB) represented by SEQ ID NO: 8 and involved in the invasion into intestinal mucosa.

In CTB, one or several amino acids may be substituted, deleted, inserted, or added in the amino acid sequence represented by SEQ ID NO: 8 as long as CTB can cause the immune response by administering to animals. The term "several" means preferably 2 to 10, more preferably 2 to 5, and still more preferably 2 to 3.

Further, CTB may be those having an identity of preferably 85% or more, more preferably 90% or more, and still more preferably 95% or more to the amino acid sequences represented by SEQ ID NO: 8, and being capable of causing the immune response by administering to the animals.

The *Escherichia coli* heat-labile toxin (LT) protein includes one A subunit which is the toxin main body and five subunits involved in the invasion into intestinal mucosa.

The Shiga toxin, the cholera toxin, and the *Escherichia coli* heat-labile toxin are also collectively referred to as "bacterial toxins" herein.

The number of the amino acids in the peptide is preferably 12 to 25 and more preferably 12 to 22. The content of proline in the peptide is preferably 20 to 27% and more preferably 20 to 25%.

Further, proline is allocated preferably every two or three residues in the peptide. But, in this case, the amino acids other than proline may be consecutive within 5 residues and preferably 4 residues in the terminus of the peptide.

In addition, the total content of serine, glycine, arginine, lysine, threonine, glutamine, asparagine, histidine, and aspartic acid in the amino acids other than proline is preferably 70% or more, more preferably 80% or more, and still more preferably 90% or more in the peptide. Further, the total content of serine, glycine, and asparagine in the amino acids other than proline is preferably 70% or more, more preferably 80% or more, and still more preferably 90% or more in the peptide. Still further, the total content of serine and glycine in the amino acids other than proline is preferably 70% or more, more preferably 80% or more, and still more preferably 90% or more in the peptide. This is because the peptide containing those amino acids abundantly is hard to form a secondary structure (β-sheet structure and helix structure).

Meanwhile, the total content of alanine, methionine, and glutamic acid in the amino acids other than proline is preferably 30% or less, more preferably 20% or less, and still more preferably 10% or less in the peptide. This is because the peptide containing those amino acids abundantly easily forms the helix structure. The total content of tryptophan, leucine, isoleucine, tyrosine, phenylalanine, and valine in the amino acids other than proline is preferably 20% or less, more preferably 10% or less, and still more preferably 5% or less in the peptide. This is because the peptide containing those amino acids abundantly easily forms the (β-sheet structure and the helix structure.

The peptide is preferably selected from the peptide (PG12) having the amino acid sequence represented by SEQ ID NO: 2, the peptide (PG17) having the amino acid sequence represented by SEQ ID NO: 82, and the peptide (PG22) having the amino acid sequence represented by SEQ ID NO: 84.

In the hybrid protein of the present invention, two or three hybrid proteins of the A subunit and the B subunit may be tandemly linked through the above peptide, or two or three A subunits may be tandemly linked through the peptide, or two or three B subunits may be tandemly linked through the peptide. When the hybrid protein contains the A subunit, the A subunit is preferably attenuated. In the hybrid protein of the present invention, preferably two or three B subunits are tandemly linked through the peptide. In the hybrid protein of the present invention, preferably two B subunits are tandemly linked through PG12.

Further, in the hybrid protein of the present invention, the peptide is preferably added to its C terminus. PG12 is particularly preferably added to its C terminus in the hybrid protein of the present invention.

The hybrid protein of the present invention has the amino acid sequence represented by SEQ ID NO: 10, 12, 14, 16, 86, 88, 90, 92, 94, 96, 98, or 100, for example. In the hybrid protein having the amino acid sequence represented by SEQ ID NO: 10, two Stx2eBs are tandemly linked through PG12. In the hybrid protein having the amino acid sequence represented by SEQ ID NO: 12, two CTBs are tandemly linked through PG12. In the hybrid protein having the amino acid sequence represented by SEQ ID NO: 14, two Stx2eBs are tandemly linked through PG12 and further PG12 is linked to the C terminus thereof. In the hybrid protein having the amino acid sequence represented by SEQ ID NO: 16, two CTBs are tandemly linked through PG12 and further PG12 is linked to the C terminus thereof. In the hybrid protein having the amino acid sequence represented by SEQ ID NO: 86, three Stx2eBs are each tandemly linked through PG12. In the hybrid protein having the amino acid sequence represented by SEQ ID NO: 88, three Stx2eBs are each tandemly linked through PG12 and further PG12 is linked to the C terminus thereof. In the hybrid protein having the amino acid sequence represented by SEQ ID NO: 90, two Stx2eBs are tandemly linked through PG17 and further PG12 is linked to the C terminus thereof. In the hybrid protein having the amino acid sequence represented by SEQ ID NO: 92, two Stx2eBs are tandemly linked through PG22 and further PG12 is linked to the C terminus thereof. In the hybrid protein having the amino acid sequence represented by SEQ ID NO: 94, three CTBs are each tandemly linked through PG12. In the hybrid protein having the amino acid sequence represented by SEQ ID NO: 96, three CTBs are each tandemly linked through PG12 and further PG12 is linked to the C terminus thereof. In the hybrid protein having the amino acid sequence represented by SEQ ID NO: 98, two CTBs are tandemly linked through PG17 and further PG12 is linked to the C terminus thereof. In the hybrid protein having the amino acid sequence represented by SEQ ID NO: 100, two CTBs are tandemly linked through PG22 and further PG12 is linked to the C terminus thereof.

By using the peptide such as PG12, PG17, or PG22 as a linker for linking the bacterial toxin proteins, the level of the bacterial toxin protein accumulated in the plant cell is increased.

In the hybrid protein of the present invention, a secretory signal peptide derived from a plant or a chloroplast transit signal peptide is preferably added to its amino terminus. Here, the term "addition" is a concept including both the case where the secretory signal peptide is directly bound to the amino terminus of the two or three bacterial toxin proteins linked through the peptide and the case where the secretory signal peptide is bound thereto through another peptide.

The secretory signal peptide is derived from preferably a plant belonging to the family Solanaceae, Brassicaceae, or Asteraceae, further preferably a plant belonging to the genus *Nicotiana, Arabidopsis, Lactuca*, etc., and more preferably *Nicotiana tabacum* or *Arabidopsis thaliana, Lactuca sativa*, etc.

Moreover, it is preferably derived from a β-D-glucan exohydrolase of *Nicotiana tabacum* or a 38-kDa peroxidase of *Nicotiana tabacum* (GenBank ACCESSION D42064).

An example of the secretory signal peptide includes a peptide that is derived from a β-D-glucan exohydrolase of *Nicotiana tabacum* and has the amino acid sequence represented by SEQ ID NO: 18.

An example of the chloroplast transit signal peptide includes a chloroplast transit signal peptide (transit peptide, T.P., SEQ ID NO: 79) derived from *Lactuca sativa* Rbcs (Rubisco small subunit) (GenBank ACCESSION D14001). A base sequence of DNA which encodes the chloroplast transit signal peptide derived from *Lactuca sativa* Rbcs is represented by SEQ ID NO: 80. Herein, the hybrid protein including the chloroplast
transit signal peptide added to its amino terminus is also referred to as a chloroplast-type (Chl) hybrid protein, and a DNA construct encoding the chloroplast-type (Chl) hybrid protein is also referred to as a chloroplast-type DNA construct. The chloroplast-type hybrid protein is efficiently accumulated particularly in a plant whose chloroplast is developed well such as *Nicotiana tabacum*.

The hybrid protein in which neither the secretory signal peptide nor the chloroplast transit signal protein is added to its amino terminus is referred to as a cytoplasm-type (Cyt) hybrid protein, and the DNA construct encoding the cytoplasm-type hybrid protein is referred to as a cytoplasmic-type DNA construct. In the cytoplasm-type hybrid protein, particularly preferably three bacterial toxin protein B subunits are tandemly linked through the peptide.

In the hybrid protein of the present invention, the signal peptide such as an endoplasmic reticulum retention signal peptide and a vacuolar transport signal peptide may be added to its carboxyl terminus. Here, the term "addition" is the concept including both the case where the signal peptide is directly bound to the carboxyl terminus of the hybrid protein and the case where the signal peptide is bound thereto through another peptide. Herein, the hybrid protein in which the secretory signal peptide is added to its amino terminus and the endoplasmic reticulum retention signal peptide is added to the carboxyl terminus is also referred to as an endoplasmic reticulum-type (ER) hybrid protein, and the DNA construct encoding the endoplasmic reticulum-type hybrid protein is also referred to as an endoplasmic reticulum-type DNA construct. The endoplasmic reticulum-type hybrid protein is efficiently accumulated particularly in a plant such as *Lactuca sativa*.

In the hybrid protein of the present invention, the endoplasmic reticulum retention signal peptide is preferably added to its carboxyl terminus. Examples of the endoplasmic reticulum retention signal peptide include an endoplasmic reticulum retention signal peptide including KDEL sequence (SEQ ID NO: 19), HDEL sequence (SEQ ID NO: 20), KDEF sequence (SEQ ID NO: 21), or HDEF sequence (SEQ ID NO: 22).

The vacuolar transport signal peptide is derived from preferably a plant belonging to the family Solanaceae, Brassicaceae, or Asteraceae, further preferably a plant belonging to the genus *Nicotiana, Arabidopsis, Armoracia*, etc., and more preferably *Nicotiana tabacum, Arabidopsis thaliana, Armoracia rusticana*, etc. In addition, the peptide is preferably derived from a chitinase. The amino acid sequence of a vacuolar transport signal peptide derived from a tobacco chitinase is represented by SEQ ID NO: 76. Meanwhile, the base sequence of DNA encoding a vacuolar transport signal peptide derived from a tobacco chitinase is represented by SEQ ID NO: 75, for example.

Moreover, the peptide is preferably derived from a horseradish peroxidase C1a isozyme. The amino acid sequence of a vacuolar transport signal peptide derived from a horseradish peroxidase C1a isozyme is represented by SEQ ID NO: 78. Meanwhile, the base sequence of DNA encoding a vacuolar transport signal peptide derived from a horseradish peroxidase C1a isozyme is represented by SEQ ID NO: 77, for example. Herein, the hybrid protein in which the secretory signal peptide is added to its amino terminus, and the vacuolar transport signal peptide is added to its carboxyl terminus is also referred to as a vacuole-type (Vac) hybrid protein, and a DNA construct encoding the vacuole-type hybrid protein is also referred to as a vacuole-type DNA construct.

The hybrid protein of the present invention may be synthesized chemically, or may be produced by genetic engineering. A method of producing by the genetic engineering is described later.

The DNA construct of the present invention is characterized by containing DNA encoding the hybrid protein of the present invention.

That is, the DNA construct of the present invention includes DNA in which DNAs encoding the two or three bacterial toxin proteins are tandemly linked through DNA encoding the peptide. The DNA encoding the peptide is represented by, for example, SEQ ID NO: 1 (PG12), SEQ ID NO: 81 (PG17), and SEQ ID NO: 83 (PG22). Examples of the DNA encoding the bacterial toxin protein include DNA (SEQ ID NO: 3) encoding Stx2eA, DNA (SEQ ID NO: 5) encoding Stx2eB, and DNA (SEQ ID NO: 7) encoding CTB. The DNA encoding the peptide and the DNA encoding the bacterial toxin protein are linked by matching their reading frames except stop codons.

The DNA encoding the bacterial toxin protein can be obtained by a common genetic engineering technique based on the base sequence of SEQ ID NO: 3, 5, or 7, for example. Specifically, a cDNA library is prepared from a bacterium which produces each bacterial toxin according to a conventional method, and a desired clone is selected using a probe prepared from the library based on the base sequence. Alternatively, the DNA can also be synthesized chemically based on the base sequence, or synthesized by PCR with genomic DNA as a template using a 5'- and 3'-terminal base sequence of the base sequence as primers, for example.

The DNA encoding the hybrid protein of the present invention is represented by SEQ ID NO: 9, 11, 13, 15, 85, 87, 89, 91, 93, 95, 97, or 99.

In the DNA encoding the hybrid protein, preferably a codon corresponding to an amino acid which composes the hybrid protein is appropriately modified so that the amount of the translated hybrid protein is increased depending on a host cell in which the hybrid protein is produced.

As the method of modifying the codon, a method of Kang et al. (2004) may serve as a reference, for example. And, the method of selecting the codon frequently used in the host cell, the method of selecting the codon in which the content of GC is high, or the method of selecting the codon frequently used in house keeping genes in the host cell is exemplified.

Further, the DNA encoding the hybrid protein may be DNA which hybridizes with DNA having the base sequence of SEQ ID NO: 9, 11, 13, 15, 85, 87, 89, 91, 93, 95, 97, or 99 under a stringent condition. The term "stringent condition" refers to the condition where a so-called specific hybrid is formed whereas no non-specific hybrid is formed. There is exemplified the condition where two DNAs with high identity, e.g., two DNAs having the identity of preferably 80% or more, more preferably 90% or more, and particularly preferably 95% or more are hybridized with each other whereas two DNAs with lower identity than that are not hybridized. Further, there is exemplified the condition of 2×SSC (330 mM NaCl, 30 mM citric acid) at 42° C. and preferably 0.1×SSC (330 mM NaCl, 30 mM citric acid) at 60° C.

In the DNA construct of the present invention, preferably the DNA encoding the hybrid protein is operably-linked to an enhancer. The term "operably" refers to the fact that the hybrid protein is produced in host cells when a vector obtained by inserting the DNA construct of the present invention into a vector including a suitable promoter is introduced into suitable host cells. In addition, the term "linked" refers to both a case where two DNAs are directly linked and a case where two DNAs are linked via another base sequence.

Examples of the enhancer include Kozak sequence and a 5'-untranslated region of an alcohol dehydrogenase gene derived from a plant. Particularly preferably, the DNA encoding the hybrid protein is operably-linked to the 5'-untranslated region of an alcohol dehydrogenase gene derived from a plant.

The 5'-untranslated region of an alcohol dehydrogenase gene refers to a region including a sequence between the base at the transcription initiation site of a gene encoding an alcohol dehydrogenase and the base before the translation initiation site (ATG, methionine). The region has a function to increase a translation level. The phrase "function to increase a translation level" refers to a function to increase an amount of a protein produced by translation when the information encoded in a structural gene is transcribed and then translated to produce a protein. The region may be derived from a plant, and it is preferably derived from a plant belonging to the family Solanaceae, Brassicaceae, or Asteraceae, further preferably derived from a plant belonging to the genus *Nicotiana, Arabidopsis, Lactuca*, etc., and more preferably derived from *Nicotiana tabacum, Arabidopsis thaliana, Lactuca sativa*, etc.

The 5'-untranslated region of an alcohol dehydrogenase gene is particularly preferably a region including the base sequence represented by SEQ ID NO: 23, which is the 5'-untranslated region of an alcohol dehydrogenase gene (NtADH 5'-UTR) derived from *Nicotiana tabacum*, for example.

The 5'-untranslated region of an alcohol dehydrogenase gene derived from a plant can be isolated from an alcohol dehydrogenase gene of a plant cultured cell where an alcohol dehydrogenase is highly expressed, for example (see JP 2003-79372 A). Meanwhile, in the case of a region having a determined base sequence, such as the 5'-untranslated region of an alcohol dehydrogenase gene derived from *Nicotiana tabacum*, the region can also be synthesized by chemical synthesis, PCR using a genomic DNA as a template and using the base sequences of the 5'- and 3'-termini of the region as primers, or the like. In addition, if a part of the region having a determined base sequence is used as a probe, the 5'-untranslated region of an alcohol dehydrogenase gene derived from another plant can be searched and isolated.

The 5'-untranslated region of an alcohol dehydrogenase gene represented by the base sequence of SEQ ID NO: 23 may have substitution, deletion, insertion, or addition of one or several bases as long as the region has a function to increase a translation level. The term "several" means the number of preferably 2 to 10, further preferably 2 to 5, and particularly preferably 2 to 3.

In addition, DNA having an identity of preferably 85% or more and particularly preferably 90% or more to the 5'-untranslated region of an alcohol dehydrogenase gene and having an ability to increase a translation level may be used.

Whether the region has an intended function to increase a translation level or not can be confirmed by, for example, a transient assay using a GUS (β-glucuronidase) gene or a luciferase gene as a reporter gene in tobacco cultured cells, or an assay in transformed cells engineered to carry those genes in a chromosome.

The DNA construct of the present invention has the base sequence represented by any one of SEQ ID NOS: 24 to 29 and SEQ ID NOS: 101 to 111, for example.

The DNA construct having the base sequence represented by SEQ ID NO: 24 is the DNA construct in which DNA (SEQ ID NO: 9) encoding the hybrid protein in which two Stx2eB proteins are tandemly linked through PG12 is linked to the 5'-untranslated region (NtADH 5'-UTR, SEQ ID NO: 23) of an alcohol dehydrogenase gene derived from *Nicotiana tabacum*. Further, the DNA construct having the base sequence represented by SEQ ID NO: 25 is the DNA construct in which DNA (SEQ ID NO: 11) encoding the hybrid protein in which two CTB proteins are tandemly linked through PG12 is linked to NtADH 5'-UTR.

The DNA construct having the base sequence represented by SEQ ID NO: 26 is the DNA construct in which DNA encoding the hybrid protein in which two Stx2eB proteins are tandemly linked through PG12, the secretory signal peptide is added to its amino terminus, and the endoplasmic reticulum retention signal peptide is added to its carboxyl terminus is linked to NtADH 5'-UTR. Further, the DNA construct having the base sequence represented by SEQ ID NO: 27 is the DNA construct in which DNA encoding the hybrid protein in which two CTB proteins are tandemly linked through PG12, the secretory signal peptide is added to its amino terminus, and the endoplasmic reticulum retention signal peptide is added to its carboxyl terminus is linked to NtADH 5'-UTR.

The DNA construct having the base sequence represented by SEQ ID NO: 28 is the DNA construct in which DNA encoding the hybrid protein in which two Stx2eB proteins are tandemly linked through PG12, the secretory signal peptide is added to its amino terminus, PG12 is linked to its carboxyl terminus, and further the endoplasmic reticulum retention signal peptide is added to its carboxyl terminus is linked to NtADH 5'-UTR. Further, the DNA construct having the base sequence represented by SEQ ID NO: 29 is the DNA construct in which DNA encoding the hybrid protein in which two CTB proteins are tandemly linked through PG12, the secretory signal peptide is added to its amino terminus, PG12 is linked to its carboxyl terminus, and further the endoplasmic reticulum retention signal peptide is added to its carboxyl terminus is linked to NtADH 5'-UTR.

The DNA construct having the base sequence represented by SEQ ID NO: 101 is the DNA construct in which DNA encoding the hybrid protein in which two Stx2eB proteins are tandemly linked through PG12 and PG12 is linked to its carboxyl terminus is linked to NtADH 5'-UTR.

The DNA construct having the base sequence represented by SEQ ID NO: 102 is the DNA construct in which DNA encoding the hybrid protein in which two Stx2eB proteins are tandemly linked through PG17 to NtADH 5'-UTR, the secretory signal peptide is added to its amino terminus, PG12 is linked to its carboxyl terminus, and further the endoplasmic reticulum retention signal peptide is added to its carboxyl terminus is linked to NtADH 5'-UTR. Further, the DNA construct having the base sequence represented by SEQ ID NO: 103 is the DNA construct in which DNA encoding the hybrid protein in which two Stx2eB proteins are tandemly linked through PG22, the secretory signal peptide is added to its amino terminus, PG12 is linked to its carboxyl terminus, and further the endoplasmic reticulum retention signal peptide is added to its carboxyl terminus is linked to NtADH 5'-UTR.

The DNA construct having the base sequence represented by SEQ ID NO: 104 is the DNA construct in which DNA encoding the hybrid protein in which two Stx2eB proteins are tandemly linked through PG12, the chloroplast transit signal peptide is added to its amino terminus, and PG12 is linked to its carboxyl terminus is linked to NtADH 5'-UTR.

The DNA construct having the base sequence represented by SEQ ID NO: 105 is the DNA construct in which DNA encoding the hybrid protein in which three Stx2eB proteins are each tandemly linked through PG12 and PG12 is linked to its carboxyl terminus is linked to NtADH 5'-UTR.

The DNA construct having the base sequence represented by SEQ ID NO: 106 is the DNA construct in which DNA encoding the hybrid protein in which three Stx2eB proteins are each tandemly linked through PG12, the secretory signal peptide is added to its amino terminus, and PG12 is linked to its carboxyl terminus, and further the endoplasmic reticulum retention signal peptide is added to its carboxyl terminus is linked to NtADH 5'-UTR.

The DNA construct having the base sequence represented by SEQ ID NO: 107 is the DNA construct in which DNA encoding the hybrid protein in which three Stx2eB proteins are each tandemly linked through PG12, the chloroplast transit signal peptide is added to its amino terminus, and PG12 is linked to its carboxyl terminus is linked to NtADH 5'-UTR.

The DNA construct having the base sequence represented by SEQ ID NO: 108 is the DNA construct in which DNA encoding the hybrid protein in which two CTB proteins are tandemly linked through PG12 and PG12 is linked to its carboxyl terminus is linked to NtADH 5'-UTR.

The DNA construct having the base sequence represented by SEQ ID NO: 109 is the DNA construct in which DNA encoding the hybrid protein in which two CTB proteins are tandemly linked through PG17, the signal peptide is added to its amino terminus, PG12 is linked to its carboxyl terminus, and further the endoplasmic reticulum retention signal peptide is added to the its carboxyl terminus is linked to NtADH 5'-UTR. Further, the DNA construct having the base sequence represented by SEQ ID NO: 110 is the DNA construct in which DNA encoding the hybrid protein in which two CTB proteins are tandemly linked through PG22, the signal peptide is added to its amino terminus, PG12 is linked to its carboxyl terminus, and further the endoplasmic reticulum retention signal peptide is added to the its carboxyl terminus is linked to NtADH 5'-UTR.

The DNA construct having the base sequence represented by SEQ ID NO: 111 is the DNA construct in which DNA encoding the hybrid protein in which two CTB proteins are tandemly linked through PG12, the chloroplast transit signal peptide is added to its amino terminus, and PG12 is linked to its carboxyl terminus is linked to NtADH 5'-UTR.

The DNA construct of the present invention can be prepared by a general genetic engineering technique, which includes the following procedures: digesting DNAs including the 5'-untranslated region of an alcohol dehydrogenase gene derived from a plant, a DNA encoding a secretory signal peptide derived from a plant, a DNA encoding a chloroplast transit signal peptide, a DNA encoding a bacterial toxin protein, and a DNA encoding an endoplasmic reticulum retention signal peptide with suitable restriction enzymes; and ligating the resultant fragments with a suitable ligase.

The recombinant vector of the present invention is characterized by including the DNA construct of the present invention. The recombinant vector of the present invention may be a vector obtained by inserting a DNA encoding a hybrid protein of the present invention into a vector so that the DNA can be expressed in host cells to be introduced with the vector. The vector is not particularly limited as long as it can replicate in host cells, and examples thereof include a plasmid DNA and a viral DNA. In addition, the vector preferably includes a selective marker such as a drug resistance gene. The plasmid DNA can be prepared from *Escherichia coli* or *Agrobacterium* by the alkaline extraction method (Birnboim, H. C. & Doly, J. (1979) Nucleic acid Res 7: 1513) or a modified method thereof. Commercially available plasmids such as pBI221, pBI121, pBI101, and pIG121Hm may be used. The viral DNA may be, for example, pTB2 (Donson et al., 1991) (see Donson J., Kerney C M., Hilf M E., Dawson W O. Systemic expression of a bacterial gene by a tobacco mosaic virus-based vector. Proc. Natl. Acad. Sci.(1991) 88: 7204-7208).

Promoters to be used in vectors may be appropriately selected depending on host cells to be introduced with vectors. The promoters are preferably a cauliflower mosaic virus 35S promoter (Odell et al., 1985, Nature 313:810), a rice actin promoter (Zhang et al. 1991 Plant Cell 3:1155), a corn ubiquitin promoter (Cornejo et al., 1993, Plant Mol. Biol., 23:567), etc. for example. Meanwhile, terminators to be used in vectors may be appropriately selected depending on host cells to be introduced with vectors. The terminators are preferably a nopaline synthase gene transcription terminator, a cauliflower mosaic virus 35S terminator, etc.

The recombinant vector of the present invention may be prepared as follows.

First, a DNA construct of the present invention is digested with a suitable restriction enzyme, or a restriction enzyme site is added to the DNA construct by PCR. Subsequently, the DNA construct is inserted into the restriction enzyme site or multicloning site of a vector.

The transformant of the present invention is characterized by being transformed with the recombinant vector of the present invention. The host cells to be used for transformation may be eukaryotic cells or prokaryotic cells.

The eukaryotic cells are preferably plant cells, particularly preferably cells of plants belonging to the family Asteraceae, Solanaceae, Brassicaceae, and Chenopodiaceae. Moreover, the eukaryotic cells are preferably cells of plants belonging to the genus *Lactuca*, particularly preferably *Lactuca sativa* cells. In the case of using *Lactuca sativa* cells as host cells, a cauliflower mosaic virus 35S RNA promoter or the like may be used in the vector.

The prokaryotic cells may be cells of *Escherichia coli*, *Agrobacterium tumefaciens*, etc.

The transformant of the present invention can be prepared by a general genetic engineering technique by introducing a vector of the present invention into host cells. For example, the transformant can be prepared by the introduction method using *Agrobacterium* (Hood, et al., 1993, Transgenic, Res. 2:218, Hiei, et al., 1994 Plant J. 6:271), an electroporation method (Tada, et al., 1990, Theor. Appl. Genet, 80:475), a polyethylene glycol method (Lazzeri, et al., 1991, Theor. Appl. Genet. 81:437), a particle gun method (Sanford, et al., 1987, J. Part. Sci. tech. 5:27), a polycation method (Ohtsuki), etc.

After introduction of the vector of the present invention into host cells, a transformant of the present invention can be selected based on the phenotype of a selective marker. If the selected transformant is cultured, the bacterial toxin protein can be produced. The culture medium and conditions for culture may be suitably selected depending on the type of a transformant.

In addition, in the case of using a plant cell as a host cell, culture of selected plant cell in accordance with a conventional method can regenerate a plant and accumulate the bacterial toxin protein in the plant cells or outside the cell membranes of the plant cells. The method depends on the type of the plant cell, and examples thereof include the method of Visser et al. (Theor. Appl. Genet, 78:594 (1989)) for potato and the method of Nagata and Takebe (Planta, 99:12 (1971)) for *Nicotiana tabacum*.

In the case of *Lactuca sativa*, a shoot can be regenerated in MS medium containing 0.1 mg/l NAA (naphthalene acetic acid), 0.05 mg/l BA (benzyladenine), and 0.5 g/l polyvinylpyrrolidone, and culture of the regenerated shoot in a ½ MS medium containing 0.5 g/l polyvinylpyrrolidone may cause rooting.

The seed of the present invention can be obtained by collecting a seed from a plant regenerated as above. If the seed of the present invention are sown and cultivated by a suitable method, a plant capable of producing a bacterial toxin protein can be obtained and is included in the transformant of the present invention.

EXAMPLES

<1> Transient Expression Experiment (1) Construction of Stx2eB Transient Expression Vector A vector containing a DNA construct in which DNA (SEQ ID NO: 5) encoding an Stx2e protein B subunit (Stx2eB) was linked to a 5'-untranslated region (NtADH 5'-UTR) of a tobacco alcohol dehydrogenase gene was prepared as follows.

A design of the vector is shown in FIG. 1.

1×Stx2eB (PG12) denotes a DNA construct containing DNA in which DNA encoding PG12 is linked to DNA encoding Stx2eB. 2×Stx2eB (PG12) denotes a DNA construct containing DNA in which two DNAs encoding Stx2eB are linked using DNA encoding PG12 as a spacer.

In addition, a DNA construct, 3×Stx2eB (PG12) in which three DNAs encoding Stx2eB are linked using DNA encoding PG12 as a spacer, and a DNA construct, 4×Stx2eB (PG12) in which four DNAs encoding Stx2eB are linked using DNA encoding PG12 as a spacer were prepared as well.

Specific techniques are shown below.

PCR using a Kozak-stx2eb-F primer (SEQ ID NO: 30) and an stx2eb-R primer (SEQ ID NO: 31) was performed to amplify a DNA fragment encoding a mature region (except for a secretory signal peptide to periplasm, Ala 19 to Asn 87) of Stx2eB. The resulting DNA fragment was cloned into an EcoRV gap in pBluescript II SK. The resulting plasmid was cleaved with HindIII, and treated with T4 DNA polymerase, followed by self-ligation to convert a HindIII site to a NheI site (plasmid 1).

Stx2eB was inserted as follows into the multicloning site (MCS) of a transient expression vector in plant cells, pBI221 (Clontech).

In order to introduce SalI, KpnI, and SmaI sites into the MCS, SalKpnSma-F (SEQ ID NO: 32) and SalKpnSma-R (SEQ ID NO: 33) were annealed and phosphorylated with T4 polynucleotide kinase (T4 PNK) (TaKaRa) and inserted into the SacI gap of pBI221 (plasmid 2). Stx2eB was cleaved out from plasmid 1 using XbaI and KpnI to insert into plasmid 2, and the resultant product was arranged between a cauliflower mosaic virus 35S RNA promoter (35S pro.) and a nopaline synthase gene transcription terminator (NOS-T) (plasmid 3).

The 5'-untranslated region (NtADH 5'-UTR, SEQ ID NO: 23) of a tobacco alcohol dehydrogenase gene was amplified by PCR with ADH-221 (Sato et al., 2004, (see below)) as a template using ADH XbaI-F primer (SEQ ID NO: 34) and ADH NsiI-R primer (SEQ ID NO: 35). A DNA region (SEQ ID NO: 17) encoding a secretory signal peptide (SEQ ID NO: 18) of β-D glucan exohydrolase (GenBank ACCESSION AB017502) was amplified with a tobacco genomic DNA as a template using βD NsiI-F primer (SEQ ID NO: 36) and βD BamHI-R primer (SEQ ID NO: 37). The obtained respective DNA fragments of NtADH 5'-UTR and the secretory signal peptide were treated with NsiI (manufactured by Toyobo Co., Ltd.), ligated using Ligation High (manufactured by Toyobo Co., Ltd.), followed by being blunted, and cloned into the EcoRV gap in pBluescript II SK (manufactured by Stratagene) (plasmid 4).

Satoh et al., The 5'-untranslated region of the tobacco alcohol dehydrogenase gene functions as an effective translational enhancer in plant. J. Biosci. Bioeng. (2004) 98, 1-8

Plasmid 4 was treated with NsiI, and blunted with T4 DNA polymerase (manufactured by Toyobo Co., Ltd.), followed by performing self-ligation to be ligated so that the initiation codon (atg) of NtADH was matched to the initiation codon of the secretory signal peptide (plasmid 5).

A DNA obtained by ligating an NtADH 5'-UTR fragment and a secretory signal peptide was amplified using plasmid 5 as a template and using ADH XbaI-F primer (SEQ ID NO: 34) and βD BamHI-R primer (SEQ ID NO: 35). The resultant DNA fragment was treated with XbaI and BamHI and inserted into the XbaI-BamHI gap of plasmid 3 (plasmid 6).

In order to add an endoplasmic reticulum retention signal (SEQ ID NO: 38), an HDEL-F primer (SEQ ID NO: 39; 'HDEL' disclosed as SEQ ID NO: 20) and an HDEL-R primer (SEQ ID NO: 40; 'HDEL' disclosed as SEQ ID NO: 20) were annealed and phosphorylated with T4 PNK, and the resultant product was inserted into the BglII gap of plasmid 6, which had been dephosphorylated with alkaline phosphatase (AP) (TakaRa) (plasmid 7).

An HA tag was added as a peptide tag for detecting Stx2eB. In order to add the HA tag, an HA-F primer (SEQ ID NO: 41) and an HA-R primer (SEQ ID NO: 42) were annealed and phosphorylated with T4 PNK. The resultant phosphorylated HA fragment was inserted into the BglII gap of plasmid 7 (plasmid 8).

A PG12 spacer (SEQ ID NO: 2) was inserted between Stx2eB and the HA tag. A PG12-F primer (SEQ ID NO: 43) and a PG12-R primer (SEQ ID NO: 44) were annealed and phosphorylated with T4 PNK. The resulting phosphorylated DNA fragment was inserted into the BglII gap of plasmid 8 (1×Stx2eB (PG12)).

2×Stx2eB (PG12) was obtained by cleaving a 2eB-PG12 fragment out from 1×Stx2eB (PG12) with BamHI and BglII and then inserting the fragment into the BamHI gap of the 1×Stx2eB (PG12). 3×Stx2eB (PG12) was obtained by cleaving an Stx2eB-PG12 fragment out from 1×Stx2eB (PG12) with BamHI and BglII and then inserting the fragment into the BamHI gap of 2×Stx2eB (PG12). Further, 4×Stx2eB (PG12) was obtained by cleaving a 2×(Stx2eB-PG12) fragment out from 2×Stx2eB (PG12) with BamHI and BglII and then inserting the fragment into the BamHI gap of the 2×Stx2eB (PG12).

(2) Construction of CTB Transient Expression Vector

A vector containing a DNA construct (2×CTB (PG12)) in which DNA encoding a CT protein B subunit (CTB) had been linked to the 5'-untranslated region of a tobacco alcohol dehydrogenase gene was prepared as follows.

A DNA fragment (SEQ ID NO: 7) encoding the mature region (except for the secretory signal to the periplasm, Thr 22 to Asn 124) (SEQ ID NO: 8) of CTB was prepared. First, the following ten primers were prepared.

CTB1: SEQ ID NO: 45
CTB2: SEQ ID NO: 46
CTB3: SEQ ID NO: 47
CTB4: SEQ ID NO: 48
CTB5: SEQ ID NO: 49
CTB6: SEQ ID NO: 50
CTB7: SEQ ID NO: 51
CTB8: SEQ ID NO: 52
CTB9: SEQ ID NO: 53
CTB10: SEQ ID NO: 54

PCR using the primers synthesized above was performed under the condition described in Kang et al. (2004). That is, PCR was performed in combination of CTB1 and CTB2, CTB3 and CTB4, CTB5 and CTB6, CTB7 and CTB8, and CTB9 and CTB10, and DNA fragments of 72 bp (1+2), 74 bp (3+4), 67 bp (5+6), 82 bp (7+8) and 68 bp (9+10) were synthesized, respectively. Subsequently, the second PCR was performed in combination of CTB1+2 and CTB3+4, CTB3+4 and CTB5+6, CTB5+6 and CTB7+8, and CTB7+8 and CTB9+10, and DNA fragments of 135 bp (1+2+3+4), 132 bp (3+4+5+6), 138 bp (5+6+7+8), and 141 bp (7+8+9+10) were synthesized, respectively. Then, the third PCR was performed in combination of CTB1+2+3+4 and CTB3+4+5+6, and CTB5+6+7+8 and CTB7+8+9+10, and DNA fragments of 194 bp (1+2+3+4+5+6) and 198 bp (5+6+7+8+9+10) were synthesized, respectively. Finally, PCR was performed in combination of CTB1+2+3+4+5+6 and CTB5+6+7+8+9+ 10, and a DNA fragment of 315 bp in which a BamHI site and a BglII site were added to a CTB coding region was synthesized.

The DNA fragment prepared above was treated with BamHI and BglII, and inserted into a BamHI-BglII gap in plasmid 8 (plasmid 9).

The PG12 spacer (SEQ ID NO: 2) was inserted between CTB and the HA tag. A PG12-F primer (SEQ ID NO: 43) and a PG12-R primer (SEQ ID NO: 44) were annealed and phosphorylated with T4 PNK. The resulting phosphorylated DNA fragment was inserted into the BglII gap of plasmid 9 (1×CTB (PG12)).

A CTB-PG12 fragment was cut out from 1×CTB (PG12) using BamHI and BglII, and inserted into the BamHI gap of 1×CTB (PG12) (2×CTB (PG12)).

(3) Transient Expression Test Using *Lactuca sativa* Protoplast

A leaf of potted *Lactuca sativa* (green wave) (about 1 g) was cut into 0.5-cm square pieces using a surgical knife, to thereby prepare leaf discs. The leaf discs were immersed in 500 mM mannitol, and shaken for 1 hour. The leaf discs were immersed in 50 ml of a protoplastization enzyme solution (1.0% cellulose RS (Yakult Honsha Co., Ltd.), 0.25% macerozyme R-10 (Yakult Honsha Co., Ltd.), 400 mM mannitol, 8 mM $CaCl_2$, and 5 mM Mes-KOH, pH 5.6), and the whole was shaken at room temperature for 2 hours. The protoplast suspension was passed through meshes of 100 µm and 40 µm to remove the leaf discs. The protoplast suspension was centrifuged at 60 g for 5 minutes to precipitate the protoplast. The protoplast was resuspended in an aqueous solution containing 167 mM mannitol and 133 mM $CaCl_2$, and the suspension was centrifuged at 40 g for 5 minutes. The protoplast was resuspended in an aqueous solution containing 333 mM mannitol and 66.7 mM $CaCl_2$, and the suspension was centrifuged at 40 g for 5 minutes. The protoplast was suspended in W5 solution (154 mM NaCl, 125 mM $CaCl_2$, 5 mM KCl, 2 mM Mes-KOH, pH 5.6), and the suspension was allowed to stand on ice for 1 hour. The protoplast suspension was centrifuged at 40 g for 5 minutes, and the protoplast was suspended in an MaMg solution (400 mM mannitol, 15 mM $MgCl_2$, and 4 mM Mes-KOH, pH 5.6) to have a protoplast concentration of $2 \times 10^6$ cells/ml.

Each of the Stx2eB transient expression vector and the CTB transient expression vector prepared above was mixed with 120 µL of a protoplast suspension, subsequently 140 µL of PEG solution (400 mM mannitol, 100 mM $Ca(NO_3)_2$ and 40% PEG) was added thereto, and the resulting mixture was blended gently and incubated for 7 minutes. Then, 1 mL of W5 solution was added to the protoplast suspension over about 20 minutes. A solution (1 mL) obtained by mixing 400 mM mannitol and the W5 solution at a ratio of 4:1 was added to the protoplast precipitated by centrifugation. LS medium (1 mL) containing 1% sucrose, 400 mM mannitol, and 0.3 mM carbenicillin was added to the protoplast precipitated by centrifugation, and the mixture was then cultured in a dark place at 25° C. for 24 hours.

(4) Western Analysis

To the protoplast collected by centrifugation were added 30 µl of SDS-sample buffer (4% (w/v) SDS, 20% (w/v) glycerol, 0.05% (w/v) bromophenol blue, 300 mM β-mercaptoethanol, 125 mM Tris-HCl, pH 6.8), followed by thermal denaturation at 95° C. for 2 minutes, to thereby prepare samples. Proteins were separated using a 15% acrylamide gel and blotted on a PVDF membrane (Hybond-P; Amersham) using an electro transfer system. An anti-HA antibody (No. 11 867 423 001, Roche) was used to detect Stx2eB and CTB.

(a) Effects of Linking Number of Stx2eB

Figure 2:
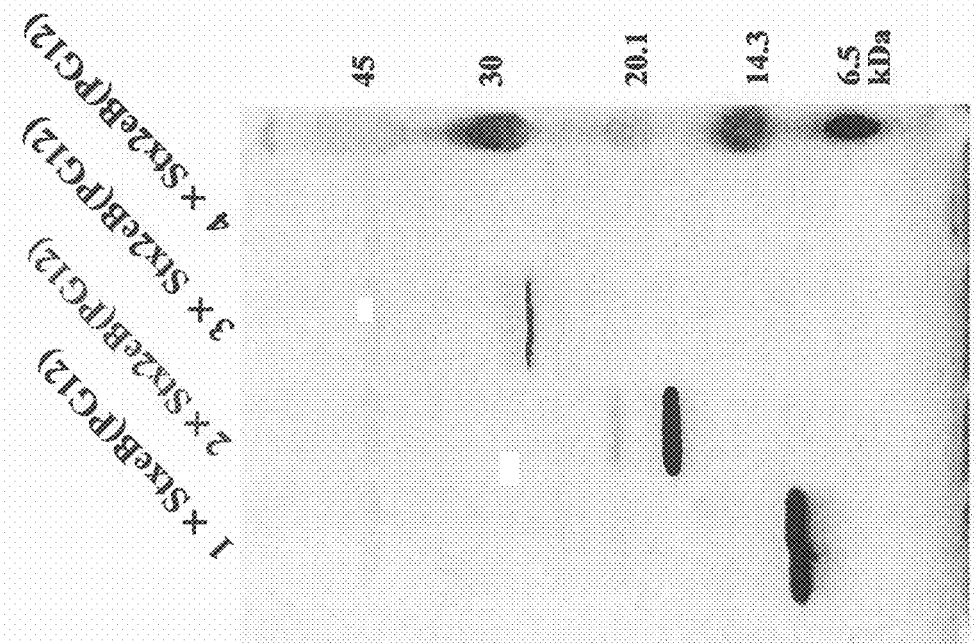
Figure 3:
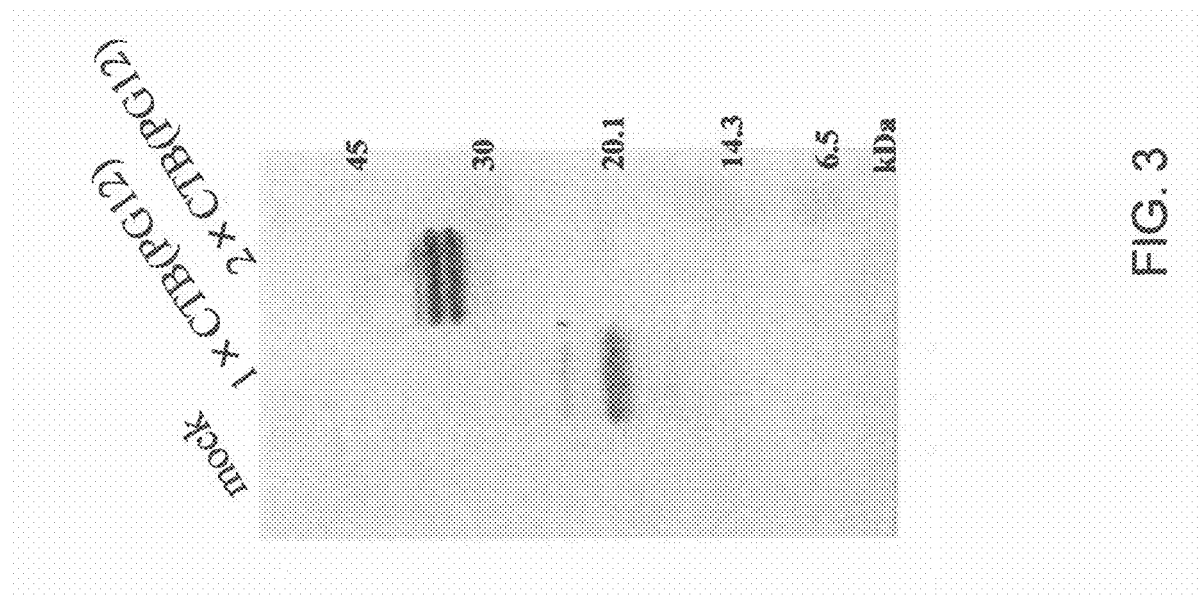
Figure 6:
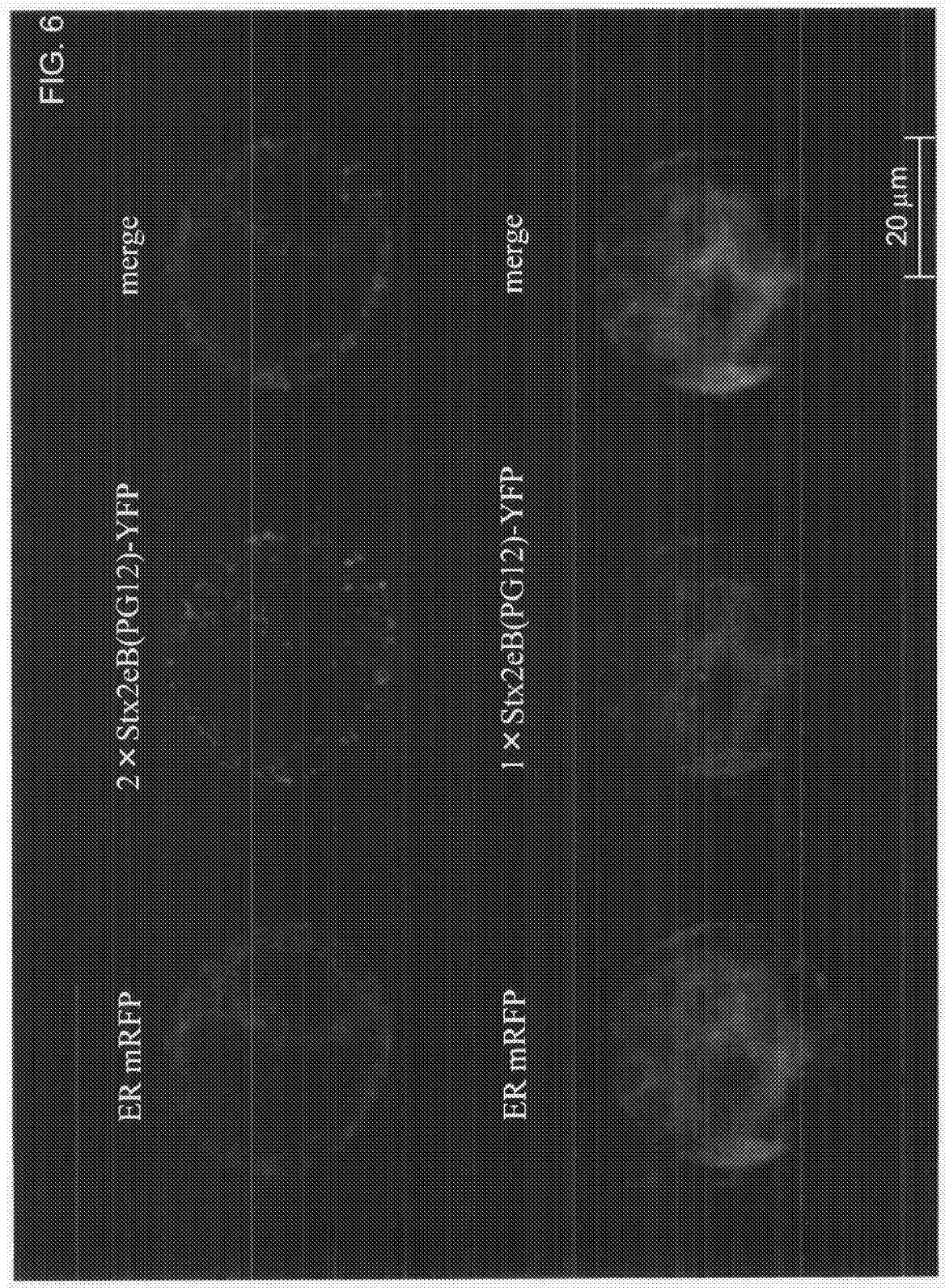

A result is shown in FIG. 2. When 1×Stx2eB (PG12) was expressed, a signal was detected at a position of about 8.5 kDa. When 2×Stx2eB (PG12) was expressed, a signal was detected at a position of about 17 kDa at the same level as when 1×Stx2eB (PG12) was expressed. When 3×Stx2eB (PG12) was expressed, a signal was detected at a position of about 26 kDa, the signal being smaller than that when 1×Stx2eB (PG12) was expressed. These corresponded to the molecular weights estimated from the design of the DNA constructs. When 4×Stx2eB (PG12) was expressed, the specific signal was below a detection limit.

From the above result, it was demonstrated that when 2×Stx2eB (PG12) and 3×Stx2eB (PG12) were expressed, hybrid proteins in which multiple Stx2eB proteins were linked could be produced.

Since each of the above DNA constructs contains one molecule of the HA tag (see FIG. 1), it is conceivable that a protein amount corresponding to about 2 times an Stx2eB protein amount when 1×Stx2eB (PG12) is expressed is accumulated when 2×Stx2eB (PG12) is expressed. That is, it has been found that when two DNAs encoding the Stx2eB protein are linked through DNA encoding PG12, the Stx2eB protein can be produced with very high efficiency.

Meanwhile, it has been also found that when three DNAs encoding the Stx2eB protein or four DNAs encoding the Stx2eB protein are linked through DNA encoding PG12, the amount of the produced Stx2eB protein is equal to or less than the amount when one Stx2eB protein is linked to PG12.

It has been found that the level of accumulated proteins tends to be higher in the Stx2eB protein (1×Stx2eB (PG12)) having PG12 added at its carboxyl terminus prepared in this experiment, compared with the Stx2eB protein having no PG12. This speculates that it is a favorable form that PG12 is added to the carboxyl terminus in the hybrid protein of the present invention.

(b) Effects of Linking Number of CTB

The results are shown in FIG. 3.

When 1×CTB (PG12) was expressed, a signal was detected at the position of about 20 kDa. When 2×CTB (PG12) was expressed, a larger signal than that when 1×CTB (PG12) was expressed was detected at the positions of about 33 kDa and about 35 kDa.

From the above results, it was demonstrated that the hybrid protein in which two CTB proteins were linked could be produced when 2×CTB (PG12) was expressed. These corresponded to the molecular weights estimated from the design of the DNA constructs.

Since each of the above DNA constructs contains one molecule of the HA tag, it is conceivable that the protein amount corresponding to the CTB protein amount which is larger than two times the protein amount when 1×CTB (PG12) is expressed is accumulated when 2×CTB (PG12) is expressed. That is, it has been found that when two DNAs encoding the CTB protein are linked through DNA encoding PG12, the CTB protein can be produced with very high efficiency.

(5) Analysis of Localization of Stx2eB

In order to analyze the localization of Stx2eB in the cell, a transient expression vector for the hybrid protein of Stx2eB and a yellow fluorescent protein YFP was prepared. The design for the vector is shown in FIG. 4. 1×Stx2eB (PG12)-YFP denotes a DNA construct in which DNA encoding the Stx2eB protein is linked to DNA encoding YFP. 2×Stx2eB (PG12)-YFP denotes a DNA construct in which DNA encoding the hybrid protein in which two Stx2eB proteins are linked through PG12 is linked to DNA encoding YFP. 2×Stx2eB (RS)-YFP using RS (Arg Ser) in place of PG12 as a spacer was also prepared.

A specific technique is shown below.

First, a DNA fragment of YFP was amplified by PCR with pEYFP (Clontech) as a template using a YFP-F primer (SEQ ID NO: 55) and a YEP-R primer (SEQ ID NO: 56). The resulting DNA fragment was treated with BamHI and BglII, and inserted into the BamHI-BglII gap of plasmid 8 (ER-YFP).

An Stx2eB fragment was cleaved out from plasmid 1 with BamHI and BglII and then inserted into the BamHI gap of the 1×Stx2eB (PG12) (2×Stx2eB (RS)).

An Stx2eB-PG12 fragment, a 2×(Stx2eB-RS) fragment, and a 2×(Stx2eB-PG12) fragment were cleaved out from 1×Stx2eB (PG12), 2×Stx2eB (RS), and 2×Stx2eB (PG12) with BamHI-BglII, respectively, and each fragment was inserted into the BamHI gap of ER-YFP (1×Stx2eB (PG12)-YFP, 2×Stx2eB (RS)-YFP, and 2×Stx2eB (PG12)-YFP).

Meanwhile, an expression vector for a red fluorescent protein (mRFP, Campbell R. E. et al., 2002, (see below)) localized in the endoplasmic reticulum was prepared as a vector for visualizing the endoplasmic reticulum. PCR was performed using an mRFP-F primer (SEQ ID NO: 57) and an mRFP-R primer (SEQ ID NO: 58). The resulting DNA fragment was treated with BamHI and BglII, and inserted into the BamHI-BglII gap of plasmid 8 (ER-mRFP).

Campbell R. E. et al., A monomeric red fluorescent protein (2002), Proc. Nat. Acad. Sci., 99: 7877-7882.

The Stx2eB expression vector and the mRFP expression vector were introduced into the protoplasts of cultured tobacco cells (BY2) in the same way as the above methods, and observed using a confocal microscope observation system (LSM510, Zeiss).

The results are shown in FIGS. 5 and 6.

Figure 5:
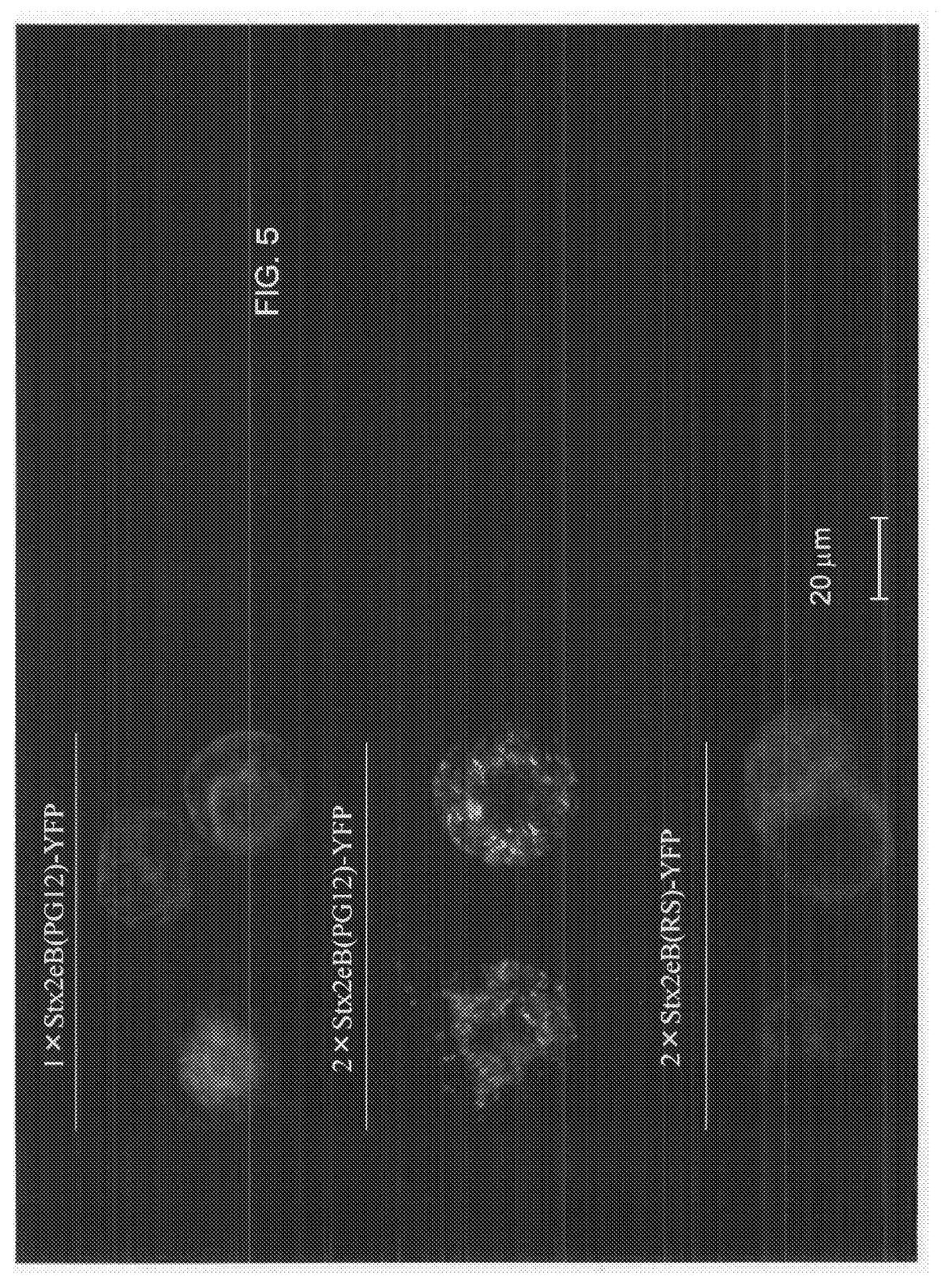

FIG. 5 shows the localization of the hybrid protein of Stx2eB-YFP. When 2×Stx2eB (PG12)-YFB was expressed, it was observed that the hybrid protein of Stx2eB-YFP was localized granularly at about 100 granules/cell. When 1×Stx2eB (PG12)-YFP and 2×Stx2eB (RS)-YFP were expressed, no granule was observed.

In FIG. 6, an image A in a leftmost column shows the localization of mRFP in a certain protoplast. The localization of mRFP reflects the location of the endoplasmic reticulum. An image B in a middle column shows the localization of the hybrid protein of Stx2eB-YFP in the identical protoplast. An image in a rightmost column is a composite image of the image A and the image B. It is found from this composite image that the hybrid protein of Stx2eB-YFP is localized granularly in the endoplasmic reticula.

(6) Effect of Vesicular Transport Function

It was examined in which process after the protein translation the accumulation and aggregation of 2×Stx2eB (PG12) occur.

2×Stx2eB (PG12)-YFP was co-expressed with an *Arabidopsis* vesicular transport regulation protein ARF1 or a dominant negative mutant thereof ARF1 (Q71L) (ARF1DN). As a reporter for inhibition of protein transport to Golgi apparatus by the co-expression with ARF1DN, vacuole-GFP was co-expressed with each ARF1. An expression vector for each ARF1 was constructed as follows. An expression vector for the vacuole-GFP can be prepared with reference to the following document.

Di Sansebastiano et. al., Specific accumulation of GFP in a non-acidic vacuolar compartment via a C-terminal propeptide-mediated sorting pathway. Plant J. (1998) 15, 449-457

As the vesicular transport regulation protein, expression vectors for *Arabidopsis* ARF1 (GenBank ACCESSION No. M95166) and for the dominant negative mutant thereof ARF1 (Q71L) (Misaki Takeuchi et al., 2002, (see below)) were constructed. PCR using cDNA prepared from *Arabidopsis* embryo plant as a template was performed using an ARF1-F primer (SEQ ID NO: 59) and an ARF1-R primer (SEQ ID NO: 60). The resulting DNA fragment was subcloned into the EcoRV gap in pBluescript (Stratagene). Another PCR was performed using an ARFQL-F primer (SEQ ID NO: 61) and an ARFQL-R primer (SEQ ID NO: 62) to substitute a glutamine residue at position 71 with a leucine residue. Each resulting ARF1 fragment was subcloned into a transient expression vector pBI221, Each of the vectors prepared was introduced into the protoplast of the cultured tobacco cell in the same manner as that described above, and the respective proteins were co-expressed to examine the localization of 2×Stx2eB (PG12).

Figure 7:
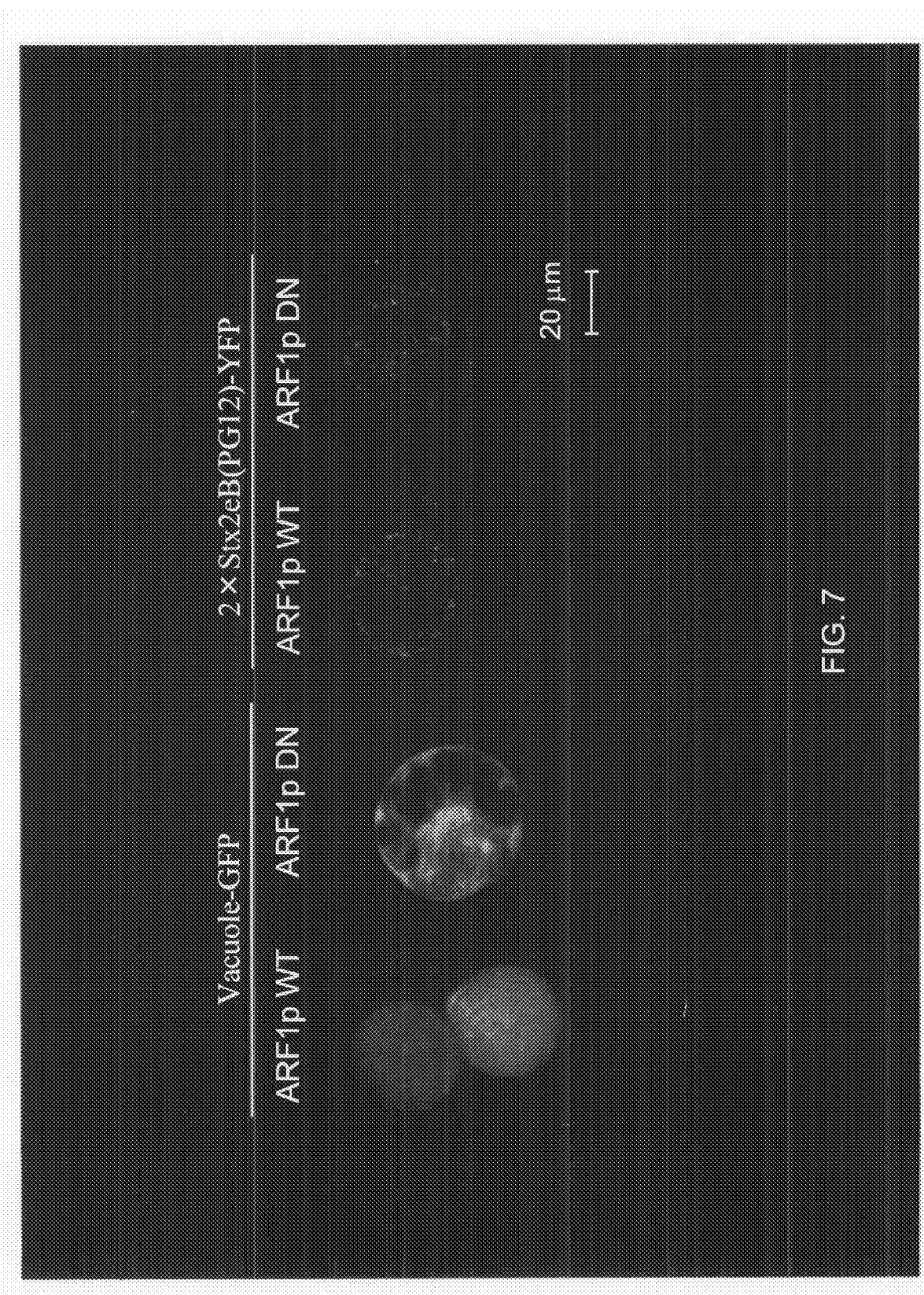
Figure 8:
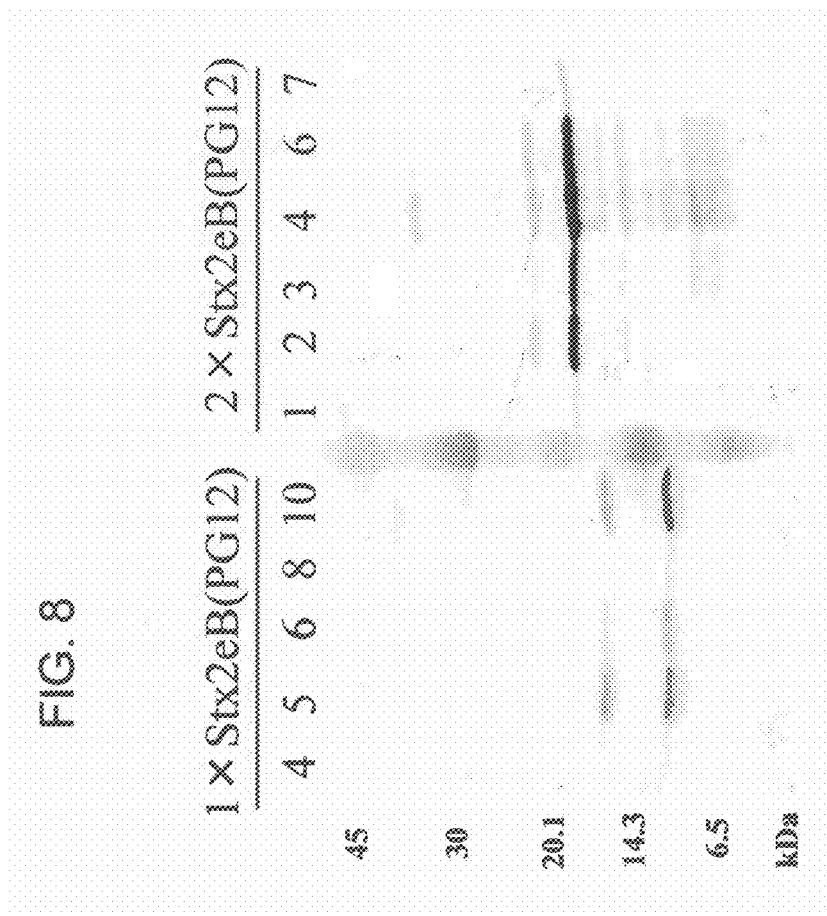
Figure 9:
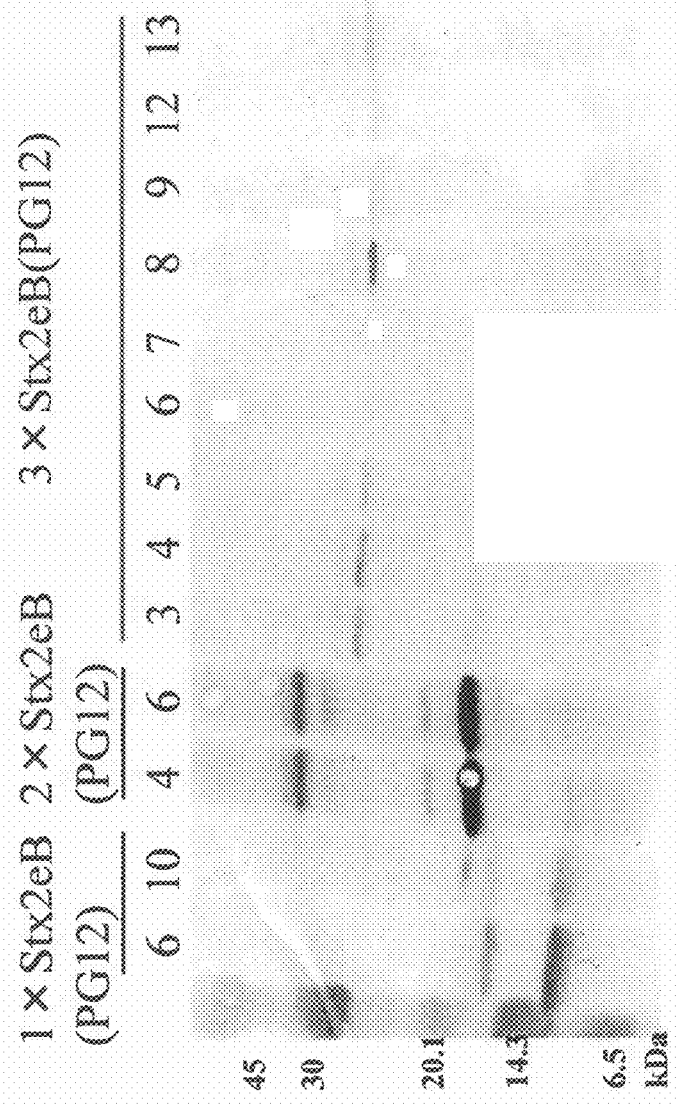
Figure 10:
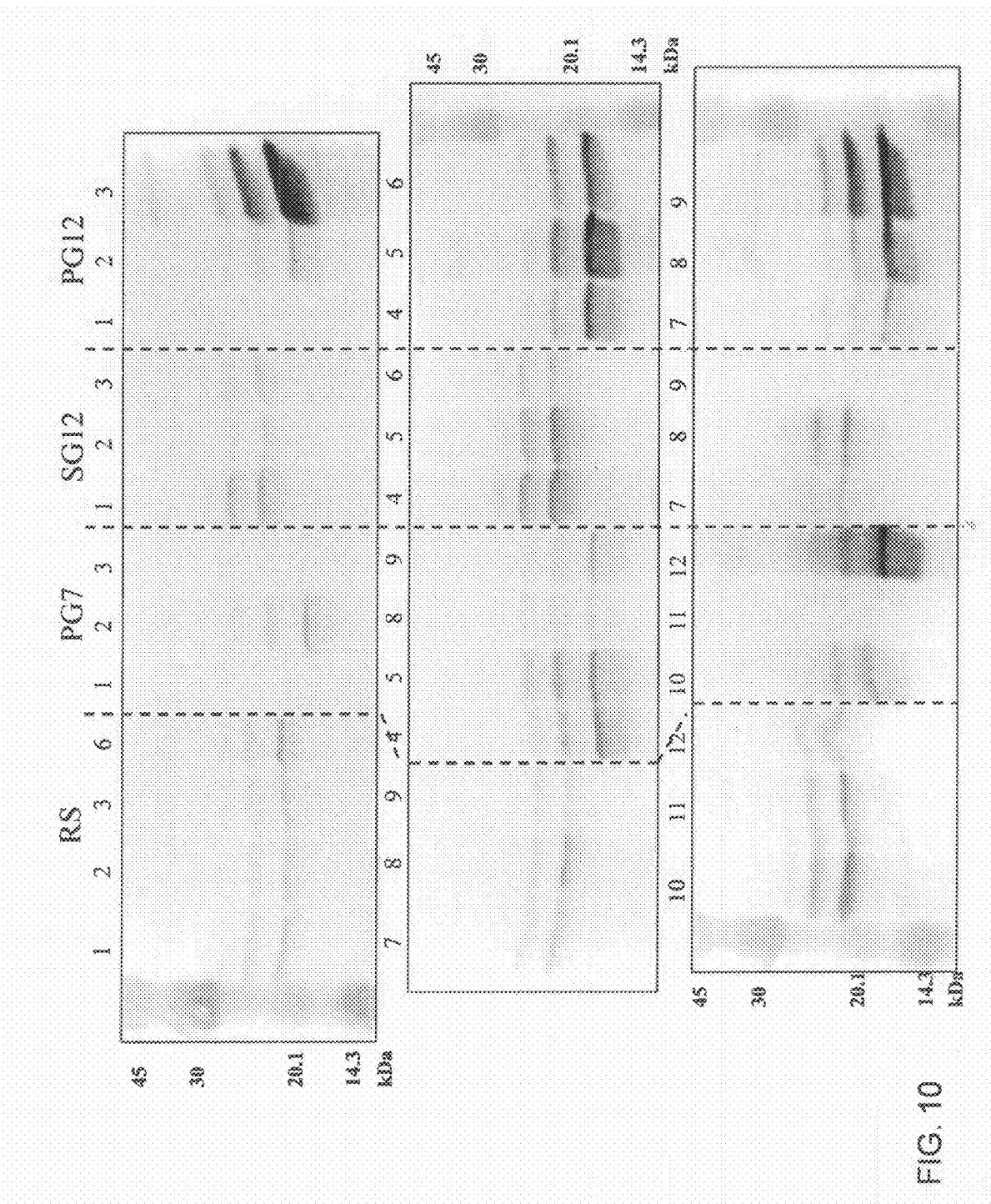
Figure 11:
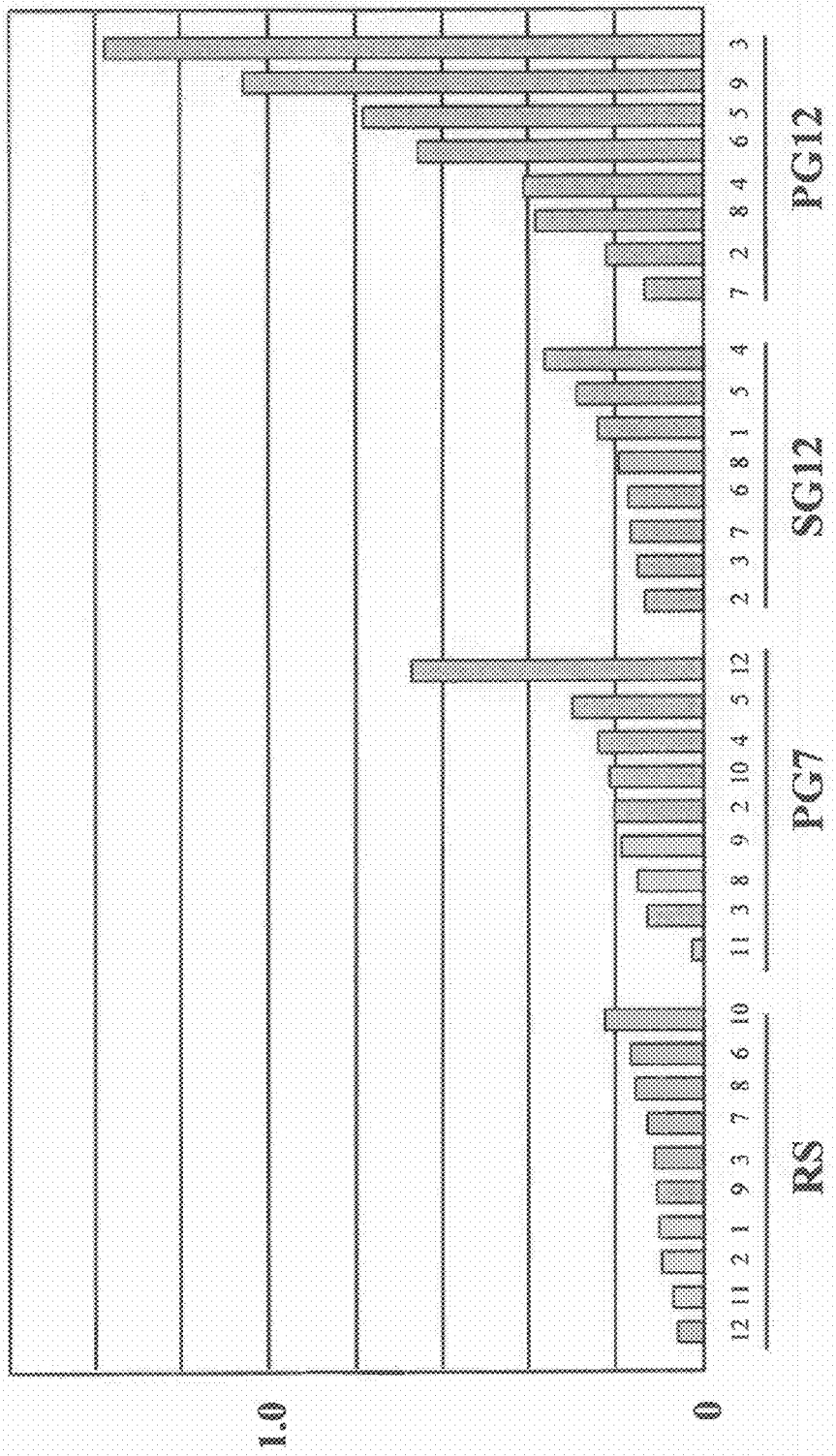

The result is shown in FIG. 7.

Both when 2×Stx2eB (PG12)-YFP was co-expressed with ARF1 and co-expressed with ARF1 (Q71L), granules were formed as observed in an expression of 2×Stx2eB (PG12)-YFP alone. On the other hand, co-expression of ARF1 (Q71L) inhibited the exit of vacuole-GFP from ER. It was speculated from these that the granule formation is not dependent on vesicular transport process from the ER to Golgi apparatus.

<2> Transformation Experiments Using Cultured Tobacco Cells (1) Construction of Vectors for Transformation 1×Stx2eB (PG12), 2×Stx2eB (PG12), 3×Stx2eB (PG12), and 4×Stx2eB (PG12) were prepared in the same way as above.

Further, by using RS (Arg, Ser), PG7 (SEQ ID NO: 63), or SG12 (SEQ ID NO: 64) as a spacer instead of PG12, DNA constructs, 2×Stx2eB (RS), 2×Stx2eB (PG7), and 2×Stx2eB (SG12) were prepared by the following methods.

A PG7 spacer (SEQ ID NO: 63) was inserted between Stx2eB and the HA tag in the plasmid 8. A PG7-F primer (SEQ ID NO: 65) and a PG7-R primer (SEQ ID NO: 66) were annealed and phosphorylated with T4 PNK. The obtained phosphorylated DNA fragment was inserted into the BglII gap of plasmid 8 (plasmid 10).

An SG12 spacer (SEQ ID NO: 64) was inserted between Stx2eB and the HA tag. An SG12-F primer (SEQ ID NO: 67) and an SG12-R primer (SEQ ID NO: 68) were annealed and phosphorylated with T4 PNK. The obtained phosphorylated DNA fragment was inserted into the BglII gap of plasmid 8 (plasmid 11).

An Stx2eB fragment was cleaved out from plasmid 1 with BamHI and BglII and then inserted into the BamHI gap of 1×Stx2eB (PG12) (2×Stx2eB (RS)). An Stx2eB-PG7 fragment was cleaved out from plasmid 10 with BamHI and BglII and then inserted into the BamHI gap of 1×Stx2eB (PG12) (2×Stx2eB (PG7)). An Stx2eB-SG12 fragment was cleaved out from plasmid 11 with BamHI and BglII and then inserted into the BamHI gap of 1×Stx2eB (PG12) (2×Stx2eB (SG12)).

In order to produce Stx2eB using a stable transformant of the plant, each of the DNA constructs of the above Stx2eB was subcloned into a vector for transformation (for the design of the vectors, see FIG. 1). Each of 1×Stx2eB (PG12), 2×Stx2eB (PG12), 3×Stx2eB (PG12), 4×Stx2eB (PG12), 2×Stx2eB (RS), 2×Stx2eB (PG7), and 2×Stx2eB (SG12) was inserted into pBI121 (Clontech) using XbaI and SacI, and allocated between a cauliflower mosaic virus 35S RNA promoter (35S pro.) and a nopaline synthetase gene transcription terminator (NOS-T).

(2) Transformation of Cultured Tobacco Cells

The produced vector for transformation was introduced into *Agrobacterium* tumefacience EHA105 using an electroporation method. An *Agrobacterium* medium (100 μL) cultured in 5 mL of LB medium containing 100 mg/L of kanamycin at 28° C. for 2 nights was mixed with 5 to 10 mL of a suspension of cultured tobacco cells (*Nicotiana tabacum*, cv BY2) on the fourth day of the culture in a petri-dish, and the mixture was co-cultured by being left to stand in a dark place at 25° C. for 2 nights. In order to remove *Agrobacterium*, the medium in the petri-dish was transferred into a 15-mL centrifuging tube, which was then centrifuged (1,000 rpm, 5 minutes, 4° C.), and a supernatant was removed. A modified LS medium was charged, and the tube was centrifuged (1,000 rpm, 5 minutes, 4° C.) to wash the cells. This washing operation was repeated four times to remove *Agrobacterium*. The resultant BY2 cells were then placed in a modified LS agar medium containing kanamycin (100 mg/L), and cultured by being left to stand in the dark place at 25° C. After about 2 to 3 weeks, cells which has formed a callus were transferred to a new plate, and a growing clone was selected.

(3) Semi-Quantification of Stx2eB Protein Using Western Analysis

Cultured tobacco cells cultured in a plate medium were collected in a centrifuging tube, and 1 μL of SDS sample buffer per mg of cell weight was added. The cells were denatured at 95° C. for 2 minutes to make a sample for electrophoresis. Proteins were separated using 15% acrylamide gel, and then blotted onto a PVDF membrane (Hybond-P; Amersham) using an electrotransfer apparatus. An Stx2eB protein was detected using an anti-HA antibody (No. 11 867 423 001, Roche). Serial dilution of Stx2eB having the HA tag at known concentrations was prepared, and loaded on the gel. A calibration curve was prepared based on their signal intensities, and the amount of Stx2eB proteins in each sample was calculated.

The results are shown below.

(a) Effects of Linking Number of Stx2eB

The results are shown in FIGS. 8 and 9.

When 1×Stx2eB (PG12) was expressed, signals were detected at the positions of about 10 kDa and about 17 kDa. They are presumed to be Stx2eB in which the signal peptide was cleaved and Stx2eB in which the signal peptide is not cleaved, respectively. When 2×Stx2eB (PG12) was expressed, a signal was detected at the position of about 19 kDa at the similar level to that when 1×Stx2eB (PG12) was expressed. When 3×Stx2eB (PG12) was expressed, a signal was detected at the position of about 26 kDa, the signal being smaller than that when 1×Stx2eB (PG12) was expressed. These corresponded to the molecular weights estimated from the design of the DNA constructs. When 4×Stx2eB (PG12) was expressed, a specific signal was below the detection limit (data not shown).

It has been found from the above that 2×Stx2eB (PG12) accumulates the larger amount of Stx2eB than 1×Stx2eB (PG12) and 3×Stx2eB (PG12).

(b) Effects of Spacer

The results are shown in FIGS. 10 and 11.

Based on the intensity of the signal corresponding to Stx2eB, the level of accumulated Stx2eB was the highest when PG12 was used as a spacer. The levels were secondly high when PG7 and SG12 were used, which were in the similar degree. The level was lowest when RS was used. This indicates that the length and the amino acid sequence of the spacer between two Stx2eBs affect the level of the accumulated 2×Stx2eB protein.

(4) Quantification of mRNA by Real-Time PCR

It was examined whether the level of the accumulated protein was influenced by a transcription level or not.

RNA was prepared using RNeasy Mini Kit (Qiagen) from each of the transformed BY2 cells obtained above. The resulting RNA was treated with DNase, and then reversely transcribed using Transcriptor Reverse Transcriptase (Roche). Real-time PCR was performed using SYBR Green PCR Master Mix (Applied Biosystems). A primer set (SEQ ID NO: 69 and SEQ ID NO: 70) which amplified the region containing NtADH 5'-UTR and the signal peptide which were common in the respective constructs was used for the quantification of Stx2eB mRNA. The amount of an expressed BY2 ubiquitin gene was quantified using a UBQ-F primer (SEQ ID NO: 71) and a UBQ-R primer (SEQ ID NO: 72) to compensate the mRNA level of an Stx2eB gene. Note that the mRNA level of 1×Stx2eB (PG12) was calculated by multiplying a quantified value by ½.

Figure 12:
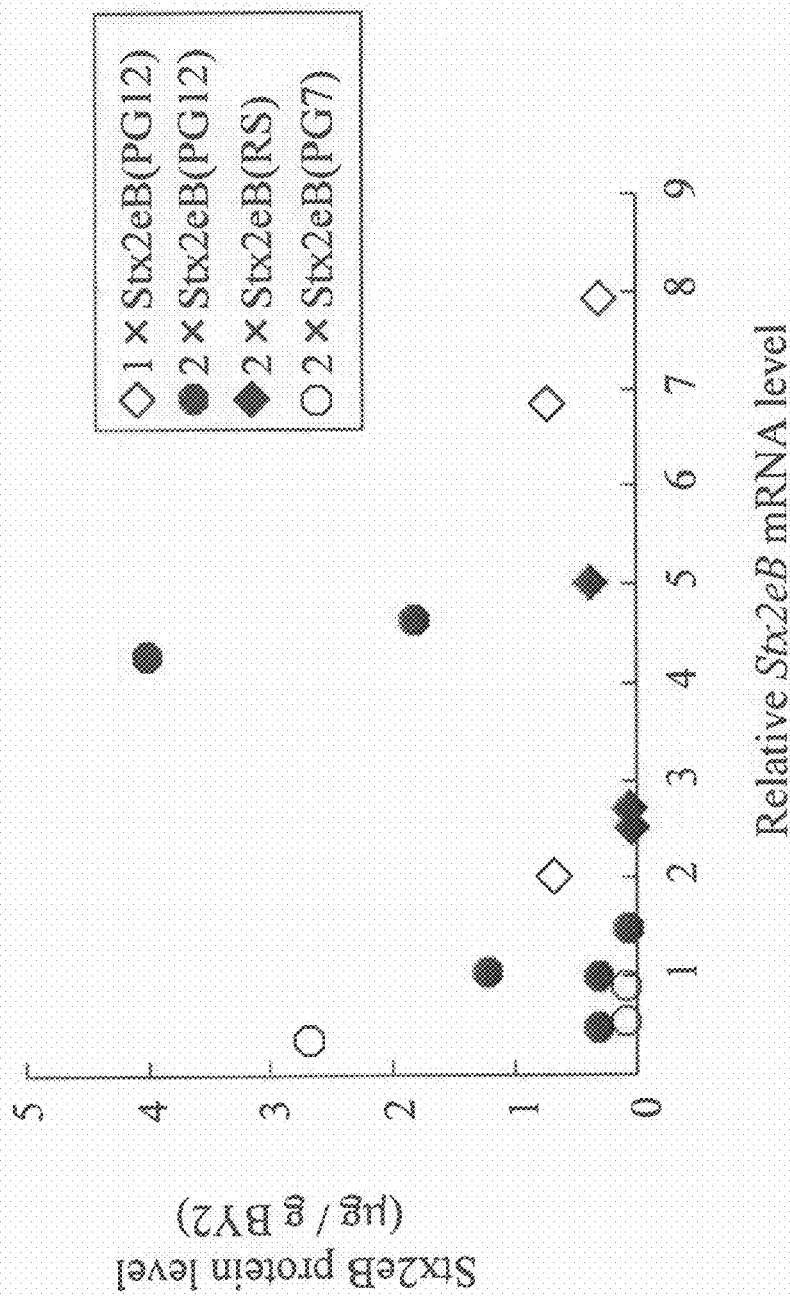

The results are shown in FIG. 12.

The accumulation levels of Stx2eB protein per mRNA tend to be higher in cells expressing 2×Stx2eB (PG12) than those in cells expressing 2×Stx2eB (RS) or 1×Stx2eB (PG12). This indicates that the difference of the spacer does not influence on the transcription level but influences on a translation level or stability of the protein after the translation. Considering together the result that the 2×Stx2eB protein was localized granularly, it is conceivable that the spacer influences on the stability of the protein after the translation.

Figure 13:
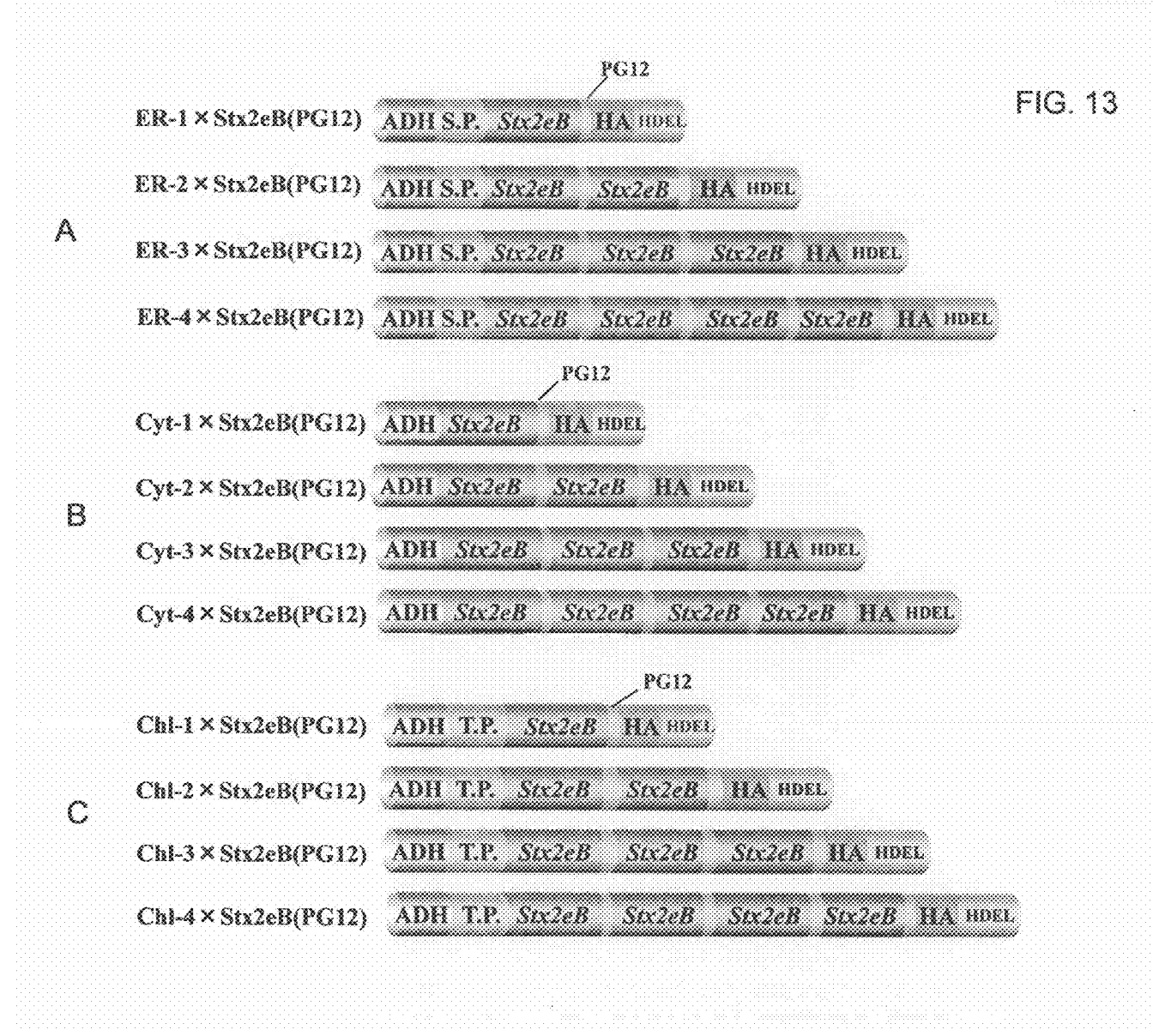

<3> Transient Expression Experiments (1) Construction of Stx2eB Transient Expression Vectors Transient expression vectors for 1×Stx2eB (PG12), 2×Stx2eB (PG12), 3×Stx2eB (PG12), and 4×Stx2eB (PG12) were constructed by the method in above <1> (1) (FIG. 13-A). These vectors are referred to as ER-1×Stx2eB (PG12), ER-2×Stx2eB (PG12), ER-3×Stx2eB (PG12), and ER-4×Stx2eB (PG12), respectively. Note that "ER" means the endoplasmic reticulum type.

Further, transient expression vectors containing the cytoplasm (Cyt) type of DNA construct (FIG. 13-B) and expression vectors containing the chloroplast (Chl) type of DNA construct (FIG. 13-C) were constructed by the following method. These DNA constructs were designed to contain DNA encoding the endoplasmic reticulum retention signal peptide, for the purpose of expressing the hybrid protein having as close a structure as possible to that of the endoplasmic reticulum type of hybrid protein. But, since these DNA constructs do not contain DNA encoding the secretory signal peptide, the endoplasmic reticulum retention signal peptide does not exert its function (retention of the protein in the endoplasmic reticulum) in the produced hybrid protein.

An NtADH 5'-UTR fragment was amplified by PCR using an ADH XbaI-F primer (SEQ ID NO: 34) and an ADH BamHI-R primer (SEQ ID NO: 112), and the resulting DNA fragment was treated with XbaI and BamHI. The XbaI-BamHI fragment of NtADH 5'-UTR was inserted into the XbaI-BamHI gap of each of ER-1×Stx2eB (PG12), ER-2×Stx2eB (PG12), ER-3×Stx2eB (PG12), and ER-4×Stx2eB (PG12) to prepare Cyt-1×Stx2eB (PG12), Cyt-2×Stx2eB (PG12), Cyt-3×Stx2eB (PG12), and Cyt-4×Stx2eB (PG12) which were cytoplasm type Stx2eB vectors.

The NtADH 5'-UTR fragment was amplified by PCR using an ADH XbaI-F primer (SEQ ID NO: 34) and an ADH NsiI-R primer (SEQ ID NO: 35). A DNA fragment (SEQ ID NO: 80) encoding the transit signal peptide, the chloroplast being derived from *Lactuca sativa* Rbcs (Rubisco small subunit) (GenBank ACCESSION D14001) (transit peptide, T.P.), was amplified by PCR with cDNA of a *Lactuca sativa* leaf as a template using a TP NsiI-F primer (SEQ ID NO: 113) and a TP BamHI-R primer (SEQ ID NO: 114). Each resulting DNA fragment of NtADH 5'-UTR and each DNA fragment of the secretory signal peptide was treated with NsiI (manufactured by Toyobo Co., Ltd.), ligated using Ligation High (Toyobo Co., Ltd.) followed by being blunted, and cloned into the EcoRV gap of pBluescript II SK (manufactured by Stratagene) (plasmid 12). Plasmid 12 was treated with NsiI, blunted with T4 DNA polymerase (Toyobo Co., Ltd.), and then self-ligated to be fused so that the initiation codon of NtADH and the initiation codon of Rbcs were matched (plasmid 13). An NtADH 5'-UTR-T.P. fusion fragment was cut out from plasmid 13 using XbaI and BamHI, and inserted into the XbaI-BamHI gap of each of ER-1×Stx2eB (PG12), ER-2×Stx2eB (PG12), ER-3×Stx2eB (PG12), and ER-4×Stx2eB (PG12) to prepare Chl-1×Stx2eB (PG12), Chl-2×Stx2eB (PG12), Chl-3×stx2eB (PG12), and Chl-4×Stx2eB (PG12), which were chloroplast type Stx2eB vectors.

(2) Production of CTB Transient Expression Vectors

Figure 14:
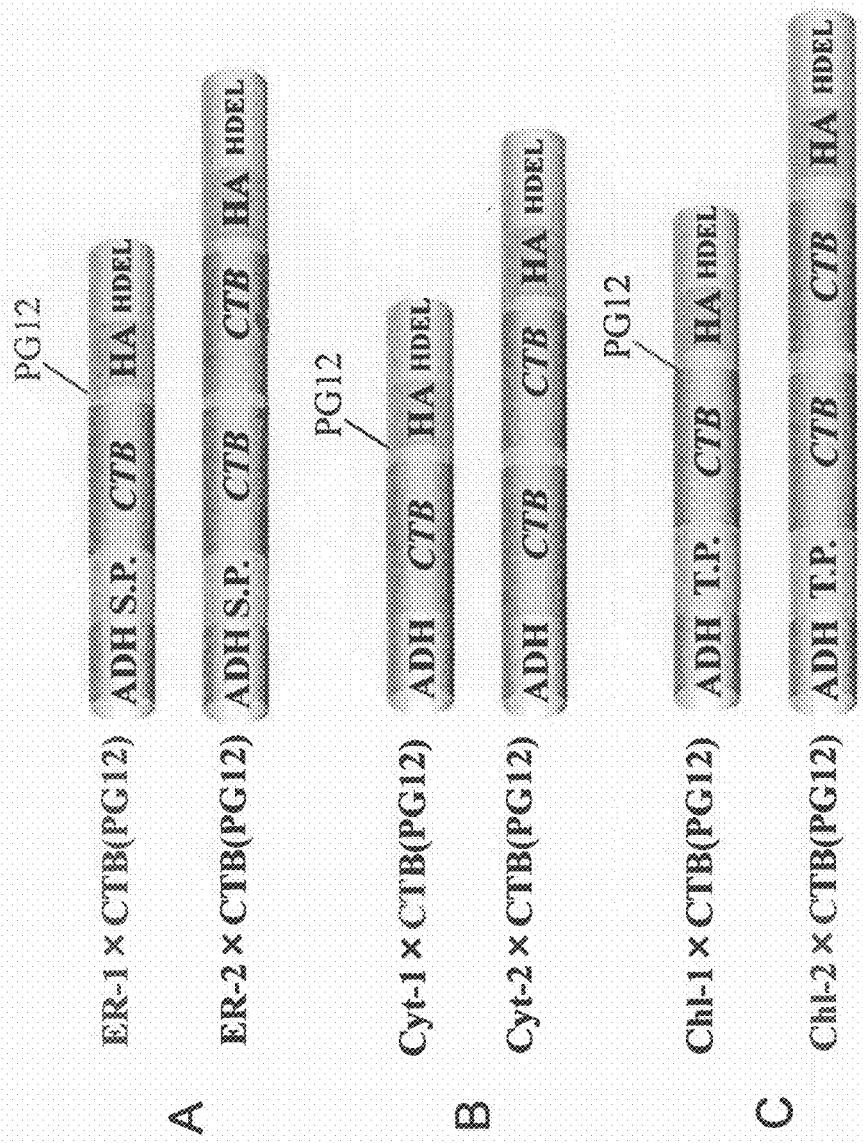
Figure 15:
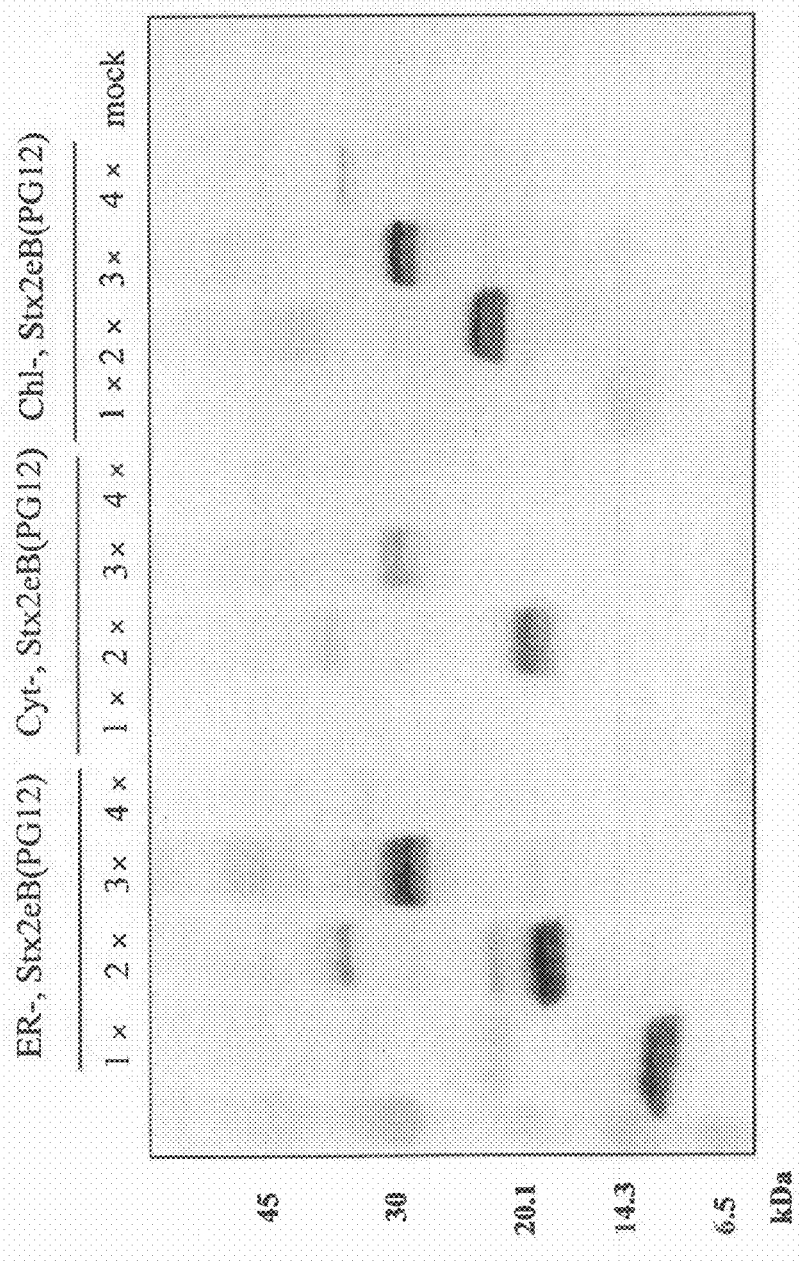
Figure 16:
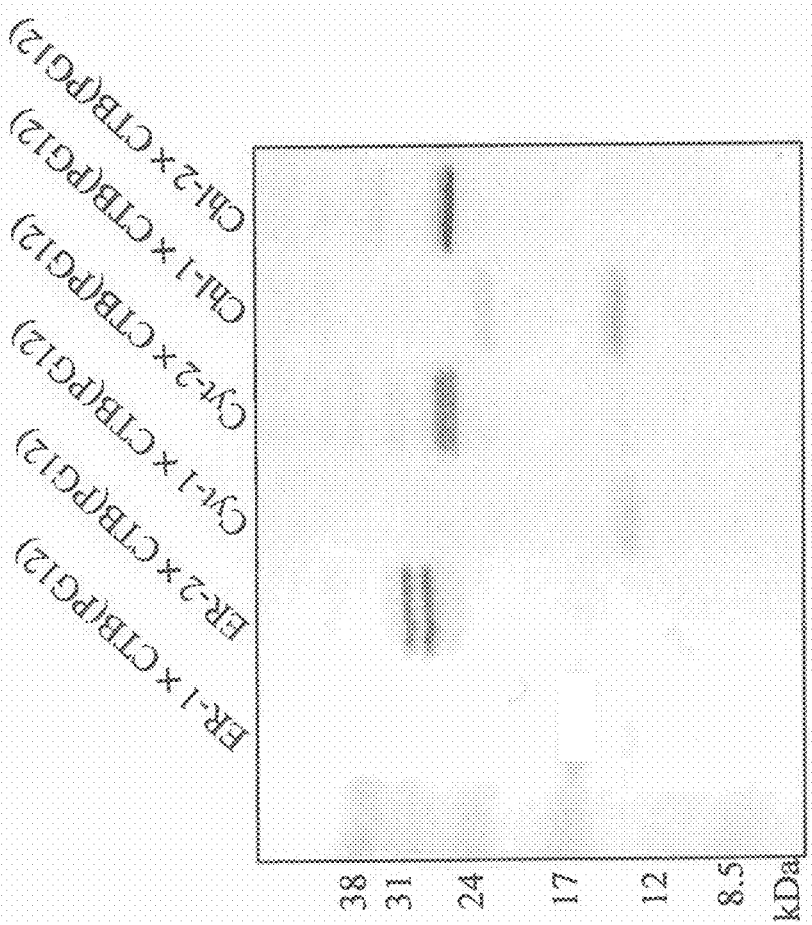
Figure 17:
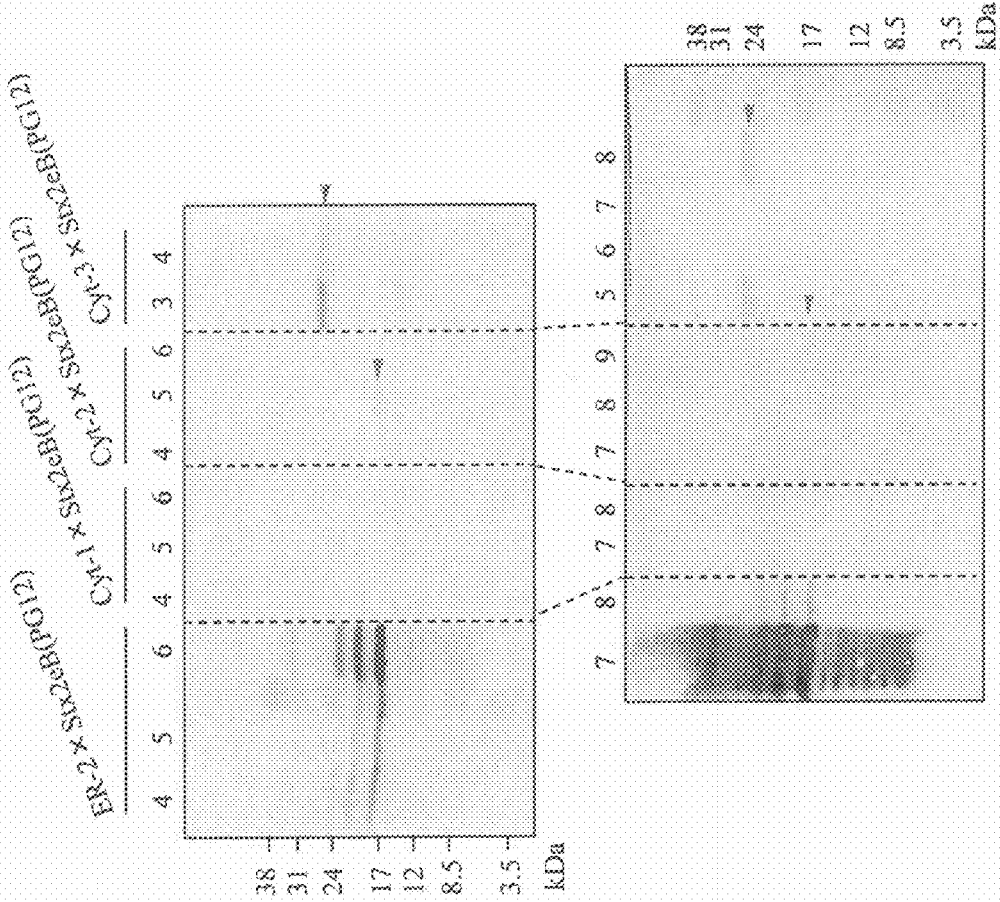
Figure 18:
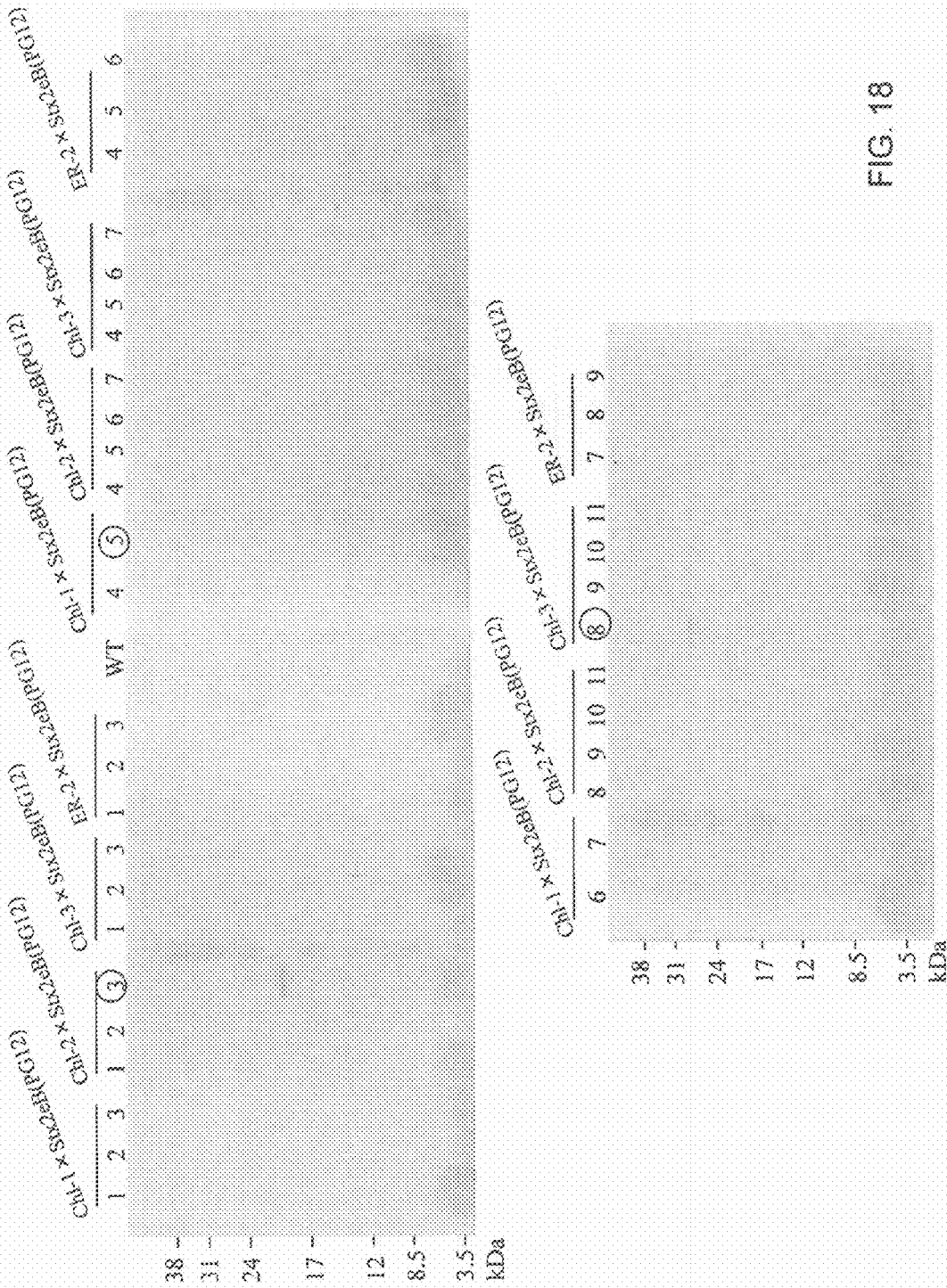
Figure 19:
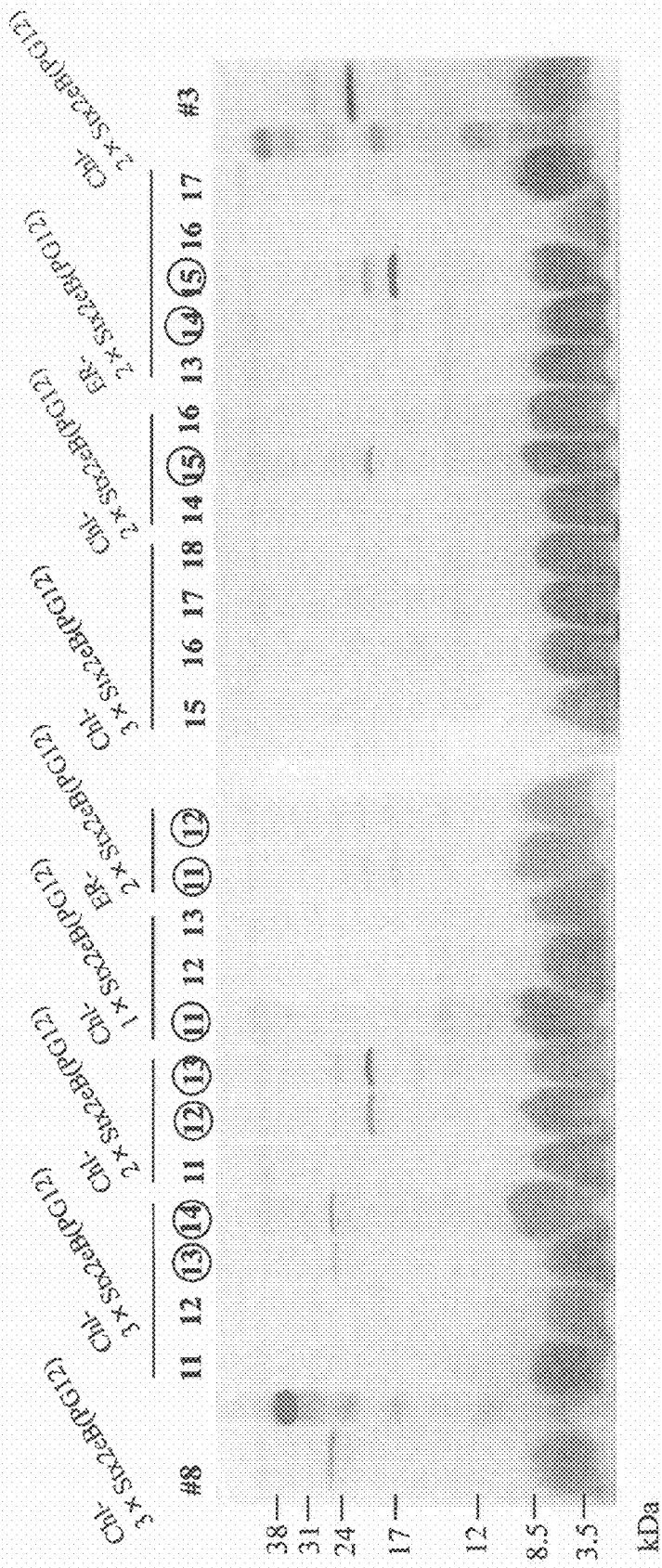

Transient expression vectors for 1×CTB (PG12) and 2×CTB (PG12) were constructed by the method in above <1> (2) (FIG. 14-A). Hereinafter, these vectors are referred to as ER-1×CTB (PG12) and ER-2×CTB (PG12).

Transient expression vectors containing the cytoplasm (Cyt) type of DNA construct (FIG. 14-B) and expression vectors containing the chloroplast (Chl) type of DNA construct (FIG. 14-C) were constructed by the following methods.

A CTB-PG12 fragment was cut out from ER-1×CTB (PG12) using BamHI and BglII, and inserted into the BamHI-BglII gap in Cyt-1×Stx2eB (PG12) and the BamHI-BglII gap in Chl-1×Stx2eB (PG12) produced in above <3> (1) to prepare cytoplasm type of 1×CTB (PG12) and chloroplast type of 1×CTB (PG12) (Cyt-1×CTB (PG12), Chl-1×CTB (PG12)).

Subsequently, a 2×(CTB-PG12) fragment was cut out from ER-2×CTB (PG12) using BamHI and BglII, and inserted into the BamHI-BglII gap of Cyt-1×Stx2eB (PG12) and the BamHI-BglII gap of Chl-1×Stx2eB (PG12) to prepare cytoplasm type of 2×CTB (PG12) and chloroplast type of 2×CTB (PG12) (Cyt-2×CTB (PG12), Chl-2×CTB (PG12)).

(3) Transient Expression Experiments and Western Analysis

Transient expression experiments were carried out using *Lactuca sativa* protoplasts in the same way as in above <1> (3). Subsequently, Stx2eB and CTB were detected in the same way as in <1> (4).

(a) Effects of Linking Number of Stx2eB

The results are shown in FIG. 15.

When ER-1×Stx2eB (PG12) was expressed, a signal was detected at the position of about 10 kDa. When ER-2×Stx2eB (PG12) was expressed, a signal was detected at the position of about 19 kDa, the signal being larger than that when ER-1×Stx2eB (PG12) was expressed. When ER-3×Stx2eB (PG12) was expressed, a signal was detected at the position of about 27 kDa, the signal being larger than that when ER-1×Stx2eB (PG12) was expressed. These corresponded to the molecular weights estimated from the design of the DNA constructs. When ER-4×Stx2eB (PG12) was expressed, a specific signal was below the detection limit.

When Cyt-1×Stx2eB (PG12) was expressed, a specific signal was below the detection limit. When Cyt-2×Stx2eB (PG12) was expressed, a signal was detected at the position of about 20 kDa. When Cyt-3×Stx2eB (PG12) was expressed, a signal was detected at the position of about 30 kDa. These corresponded to the molecular weights estimated from the design of the DNA constructs. Further, when Cyt-4×Stx2eB (PG12) was expressed, a specific signal was below the detection limit.

When Chl-1×Stx2eB (PG12) was expressed, a signal was detected faintly at the position of about 14 kDa. When Chl-2×Stx2eB (PG12) was expressed, a signal was detected at the position of about 22 kDa, the signal being at the similar level to that when ER-3×Stx2eB (PG12) was expressed. When Chl-3×Stx2eB (PG12) was expressed, a signal was detected at the position of about 30 kDa, the signal being at the similar level to that when Chl-2×Stx2eB (PG12) was expressed. These corresponded to the molecular weights estimated from the design of the DNA constructs. When Chl-4×Stx2eB (PG12) was expressed, a signal was detected faintly at the position of about 34 kDa.

Since each of the above DNA constructs contains one molecule of the HA tag (see FIG. 13), when DNA encoding two Stx2eBs is expressed and when DNA encoding three Stx2eBs is expressed, the amounts of the accumulated proteins are thought to correspond to about two times and about three times, respectively, the amount when DNA containing one Stx2eB is expressed.

Therefore, it has been found that when any of the endoplasmic reticulum type (ER), cytoplasm type (Cyt), and chloroplast type (Chl) of DNA constructs is expressed, the Stx2eB protein can be more efficiently accumulated when the protein in which two or three Stx2eBs are tandemly linked through the spacer is expressed than when one Stx2eB protein is expressed.

(b) Effects of Linking Number of CTB

The results are shown in FIG. 16.

When ER-1×CTB (PG12) was expressed, a signal was detected at the position of about 17 kDa. When ER-2×CTB (PG12) was expressed, a larger signal than that when ER-1×Stx2eB (PG12) was expressed was detected at the positions of about 28 kDa and about 30 kDa. These corresponded to the molecular weights estimated from the design of the DNA constructs.

When Cyt-1×CTB (PG12) was expressed, a signal was faintly detected at the position of about 14 kDa. When Cyt-2×CTB (PG12) was expressed, a signal was detected at the position of about 26 kDa, the signal being at the similar level to that when ER-2×CTB (PG12) was expressed. These corresponded to the molecular weights estimated from the design of the DNA constructs.

When Chl-1×CTB (PG12) was expressed, a signal was detected at the position of about 14 kDa. When Chl-2×CTB (PG12) was expressed, a signal was detected at the position of about 26 kDa, the signal being at the similar level to that when ER-2×CTB (PG12) was expressed. These corresponded to the molecular weights estimated from the design of the DNA constructs.

From the above, it has been found that when any of the endoplasmic reticulum type (ER), cytoplasm type (Cyt), and chloroplast type (Chl) of DNA constructs is expressed, CTB proteins can be more efficiently accumulated when the protein in which two CTBs are tandemly linked through the spacer is expressed than when one CTB protein is expressed.

<4> Transformation Experiments Using Cultured Tobacco Cells (1) Construction of Vectors for Transformation Transformation experiments were performed using ER-2×Stx2eB (PG12), Cyt-1×Stx2eB (PG12), Cyt-2×Stx2eB (PG12), and Cyt-3×Stx2eB (PG12) prepared above.

Vectors for transformation were prepared in the same way as the method in above <2> (1).

(2) Transformation and Western Analysis of Cultured Tobacco Cells

Transformation experiments and the western analysis were carried out in the same ways as the methods in above <2> (2) and (3).

The results are shown in FIG. 17.

When ER-2×Stx2eB (PG12) was expressed, a signal was detected at the positions of about 19, 21, and 23 kDa. When Cyt-1×Stx2eB (PG12) was expressed, a specific signal was below the detection limit. When Cyt-2×Stx2eB (PG12) was expressed, a signal was detected at the position of about 19 kDa. When Cyt-3×Stx2eB (PG12) was expressed, a signal was detected at the position of about 27 kDa, the signal being larger than that when Cyt-2×Stx2eB (PG12) was expressed.

From the above, it has been found that also in the transformant of the cultured tobacco cell, Stx2eB proteins can be more efficiently accumulated when the protein in which two or three Stx2eBs are tandemly linked through the spacer is expressed than when one Stx2eB protein is expressed. It has been also found that when the cytoplasm type of DNA construct is expressed in the transformant of the cultured tobacco cell, in particular when the protein in which three Stx2eBs are tandemly linked through the spacer is expressed, the Stx2eB proteins can be efficiently accumulated.

It has been also found that in the transformant of the cultured tobacco cell, the Stx2eB proteins can be more efficiently accumulated when the endoplasmic reticulum type of DNA construct is expressed than when the cytoplasm type of DNA construct is expressed.

<5> Transformation Experiments Using Tobacco Plant Body (1) Construction of Vectors for Transformation Transformation experiments were performed using ER-2×Stx2eB (PG12), Chl-1×Stx2eB (PG12), Chl-2×Stx2eB (PG12), and Chl-3×Stx2eB (PG12) prepared above.

Vectors for transformation were prepared in the same way as the method in above <2> (1).

(2) Transformation of Tobacco Plant Body

Tobacco plant bodies were transformed by the following method using the vectors prepared above.

Seeds of the tobacco plant body (*Nicotiana tabacum* L. cv. Petit habana SR1) were sterilized and seeded on an MS medium. A leaf portion of the sterilized *Nicotiana tabacum* was cut into pieces each having a size of about 1×1 cm without including leaf veins, and placed to face up the backside of the leaf in a petri-dish containing sterile water. An *Agrobacterium* suspension cultured for two nights in the LB medium containing 100 mg/L of kanamycin and obtained in above <2> (2) was poured in the petri-dish, and the leaf piece was immersed therein for 3 to 5 minutes. The leaf piece was picked up, and an extra bacterial medium on the leaf piece was wiped with sterile kim-towel. The leaf piece was placed on a callus formation medium and cultured at 25° C. After 2 to 3 days, when *Agrobacterium* became visible on the medium, the leaf piece was transferred into a 50-mL tube, washed five times with sterile water, placed on a callus formation medium (containing 100 mg/L of kanamycin and 250 mg/L of carbenicillin), and cultured at 25° C. for 1 to 2 weeks. When the leaf piece curled up compared with the original and showed a concavoconvex surface, the leaf piece was transferred into a shoot formation medium (containing 100 mg/L of kanamycin and 250 mg/L of carbenicillin). After additional 4 to 6 weeks, a shoot having a developed stem and leaf portion was cut off, transferred to a root formation medium (containing 100 mg/L of kanamycin and 250 mg/L of carbenicillin), and cultured at 25° C. until rhizogenesis was observed. A plant body grown to a certain size was grown as a pot plant.

(3) Western Analysis

The leaf of the genetically engineered tobacco plant body produced above was sampled, and an SDS sample buffer was added thereto in the proportion of 1 μL of SDS to 1 mg of leaf. The sample was thermally denatured at 95° C. for 2 minutes to serve as the sample for electrophoresis. Proteins were separated using 15% acrylamide gel, and then blotted onto a PVDF membrane (Hybond-P; Amersham) using an electrotransfer apparatus. The Stx2eB protein was detected using an anti-HA antibody (No. 11 867 423 001, Roche).

The results are shown in FIGS. 18 and 19.

Clones in which Stx2eB was accumulated with high efficiency were obtained in the plant body transformed with one of ER-2×Stx2eB (PG12), Chl-1×Stx2eB (PG12), Chl-2×Stx2eB (PG12), and Chl-3×Stx2eB (PG12). Also in the chloroplast type of DNA constructs, it has been found that the clone accumulating Stx2eB efficiently is obtained with a higher probability when the protein in which two or three Stx2eBs are tandemly linked through the spacer is expressed than when one Stx2eB protein is expressed.

When ER-2×Stx2eB (PG12) was expressed, signals were detected at the positions of about 15 kDa, about 19 kDa, and about 22 kDa. When Chl-1×Stx2eB (PG12) was expressed, a signal was detected at the position of about 12 kDa. When Chl-2×Stx2e8 (PG12) was expressed, a signal was detected at the position of about 19 kDa. When Chl-3×Stx2eB (PG12) was expressed, a signal was detected at the position of about 27 kDa. These corresponded to the molecular weights estimated from the design of the DNA constructs.

Figure 20:
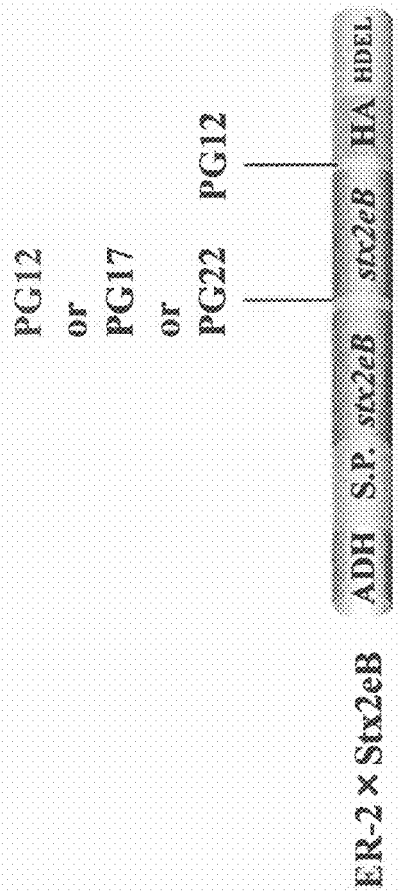

<6> Transformation Experiments Using Cultured Tobacco Cells (1) Construction of Vectors for Stx2eB Transformation ER-2×Stx2eB (PG12) was prepared by the method in above <1> (1). ER-2×Stx2eB (PG17) and ER-2×Stx2eB (PG22) were prepared by the following method. The design of the DNA constructs is shown in FIG. 20.

A PG7-F primer (SEQ ID NO: 65) and a PG7-R primer (SEQ ID NO: 66) were annealed and phosphorylated with T4 PNK. The resulting phosphorylated DNA fragment was inserted into the BglII gap of ER-1×Stx2eB (PG12) obtained in <1> (1) (plasmid 14).

A PG12-F primer (SEQ ID NO: 43) and a PG12-R primer (SEQ ID NO: 44) were annealed and phosphorylated with T4 PNK. The resulting phosphorylated DNA fragment was inserted into the BglII gap of ER-1×Stx2eB (PG12) (plasmid 15).

An Stx2eB-PG17 fragment was cut out from plasmid 14 using BamHI and BglII, and inserted into the BamHI gap of ER-1×Stx2eB (PG12) (2×Stx2eB (PG17)). An Stx2eB-PG22 fragment was cut out from plasmid 15 using BamHI and BglII, and inserted into the BamHI gap of ER-1×Stx2eB (PG12) (ER-2×Stx2eB (PG22)).

In order to produce Stx2eB using the stable transformant of the plant, each of the above DNA constructs for Stx2eB was subcloned into a vector for transformation. That is, each of ER-2×Stx2eB (PG12), ER-2×Stx2eB (PG17), and ER-2×Stx2eB (PG22) was inserted into pBI121 (Clontech) using XbaI and SacI, and allocated between the cauliflower mosaic virus 35S RNA promoter (35S pro.) and the nopaline synthetase gene transcription terminator (NOS-T).

(2) Construction of Vectors for CTB Transformation

Figure 21:
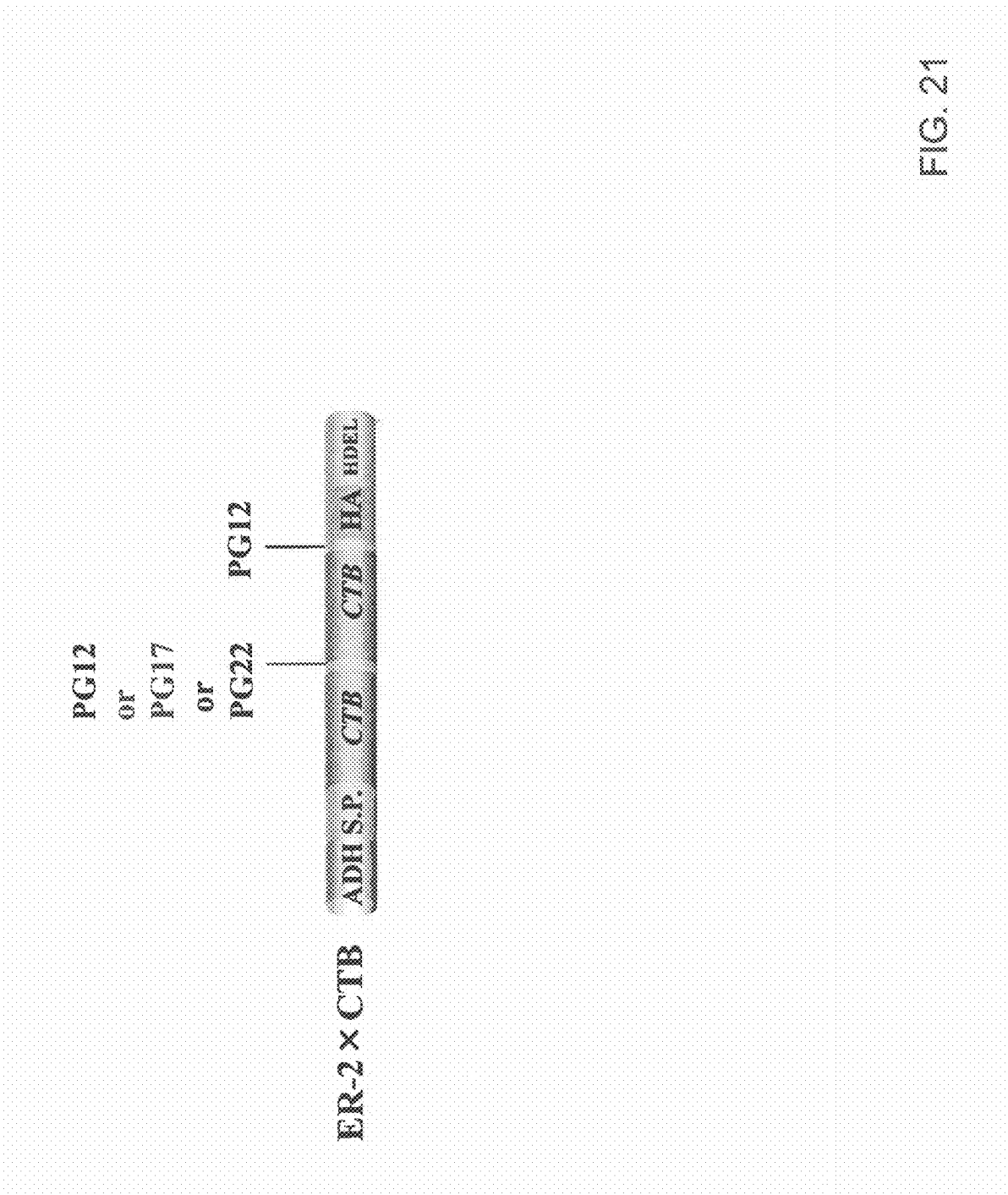

ER-2×CTB (PG12) was prepared by the method in above <1> (2). ER-2×CTB (PG17) and ER-2×CTB (PG22) were prepared by the following method. The design of the DNA constructs is shown in FIG. 21.

A PG7-F primer (SEQ ID NO: 65) and a PG7-R primer (SEQ ID NO: 66) were annealed and phosphorylated with T4 PNK. The resulting phosphorylated DNA fragment was inserted into the BglII gap of ER-1×CTB (PG12) obtained in <1> (2) (plasmid 16). A PG12-F primer (SEQ ID NO: 43) and a PG12-R primer (SEQ ID NO: 44) were annealed and phosphorylated with T4 PNK. The resulting phosphorylated DNA fragment was inserted into the BglII gap of ER-1×CTB (PG12) (plasmid 17).

A CTB-PG17 fragment was cut out from plasmid 16 using BamHI and BglII, and inserted into the BamHI gap of ER-1×CTB (PG12) (ER-2×CTB (PG17)). A CTB-PG22 fragment was cut out from plasmid 17 using BamHI and BglII, and inserted into the BamHI gap of ER-1×CTB (PG12) (ER-2× CTB (PG22)).

In order to produce CTB using the stable transformant of the plant, each of the above DNA constructs for CTB was subcloned into a vector for transformation. That is, each of ER-2×CTB (PG12), ER-2×CTB (PG17), and ER-2×CTB (PG22) was inserted into pBI121 (Clontech) using XbaI and SacI, and allocated between the cauliflower mosaic virus 35S RNA promoter (35S pro.) and the nopaline synthetase gene transcription terminator (NOS-T).

(3) Transformation Experiments and Western Analysis

Transformation experiments and western analysis were carried out by the methods in above <2> (2) and (3).

(a) Effects of Length of Spacer on Tandem Linking of Stx2eB

The results are shown in FIG. 22.

When one of ER-2×Stx2eB (PG17) and ER-2×Stx2eB (PG22) was expressed, a signal was detected at the similar level to that when ER-2×Stx2eB (PG12) was expressed. This indicates that any of PG17 and PG22 exhibits the same effect as PG12.

When ER-2×Stx2eB (PG12) was expressed, signals were detected at the positions of about 19 kDa and about 22 kDa. When ER-2×Stx2eB (PG17) was expressed, signals were detected at the positions of about 19 kDa and about 22 kDa. When ER-2×Stx2eB (PG22) was expressed, signals were detected at the positions of about 20 kDa and about 23 kDa. These corresponded to the molecular weights estimated from the design of the DNA constructs.

(b) Effects of Length of Spacer on Tandem Linking of CTB

Figure 23:
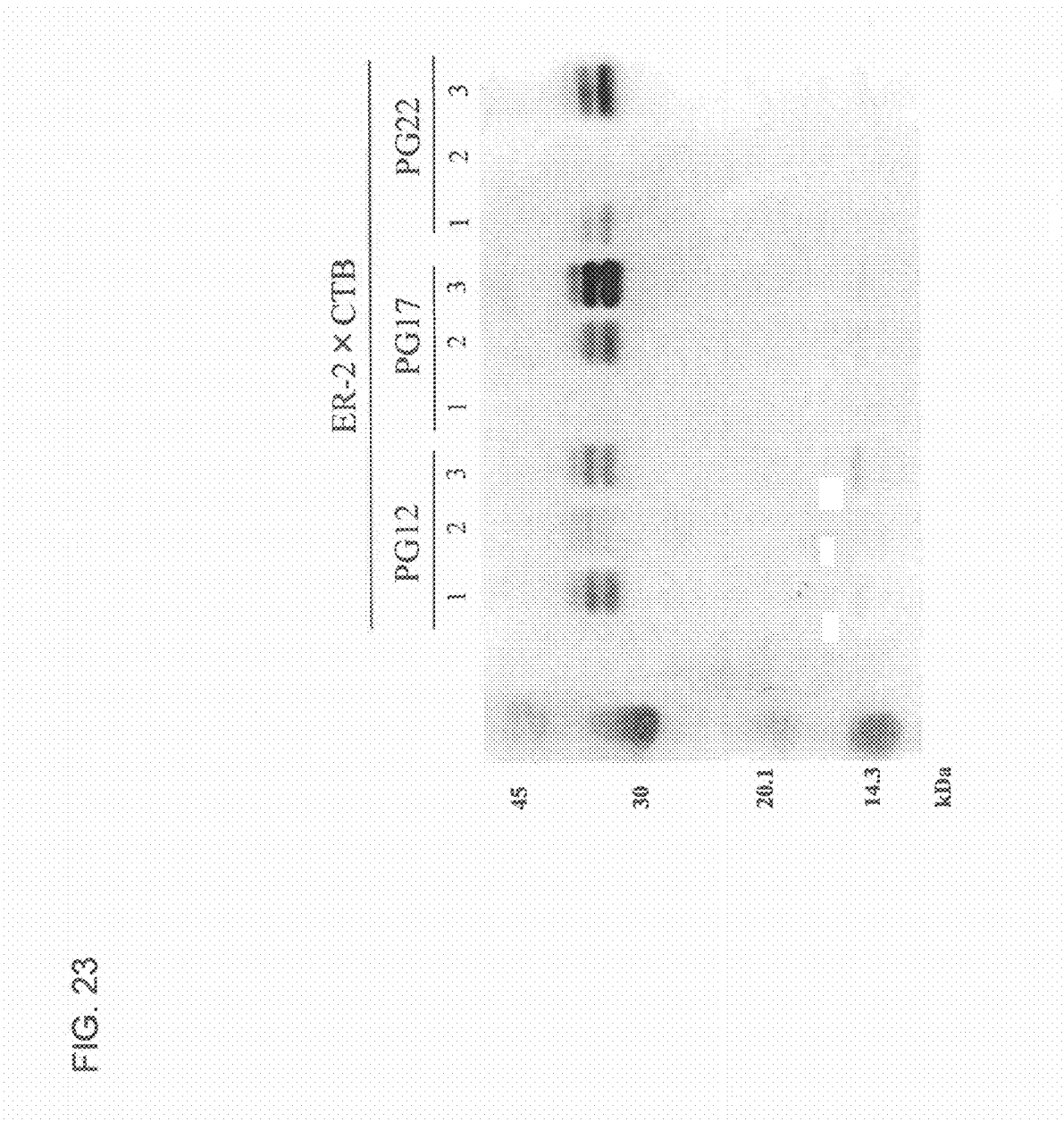
FIG. 23 is a photograph illustrating the levels of accumulated CTB obtained in a transformation experiment using the cultured tobacco cells (BY2).

The results are shown in FIG. 23.

When one of ER-2×CTB (PG17) and ER-2×CTB (PG22) was expressed, a signal was detected at the similar level to that when ER-2×CTB (PG12) was expressed. This indicates that any of PG17 and PG22 exhibits the same effect as PG12.

When ER-2×CTB (PG12) was expressed, signals were detected at the positions of about 32 kDa, about 34 kDa, and about 36 kDa. When ER-2×CTB (PG17) was expressed, signals were detected at the positions of about 32 kDa, about 34 kDa, and about 36 kDa. When ER-2×CTB (PG22) was expressed, signals were detected at the positions of about 32 kDa, about 34 kDa, and about 36 kDa. These corresponded to the molecular weights estimated from the design of the DNA constructs.

INDUSTRIAL APPLICABILITY

The hybrid protein of the present invention is highly stable and accumulated at a high level in plant cells. Besides, by producing the hybrid protein of the present invention in the plant using the DNA construct of the present invention, it is possible to efficiently produce oral vaccines for Shiga toxin, cholera toxin, and *Escherichia coli* heat-labile toxin.

The present invention enables to express a bacterial antigen in the plant at the level which is enough to induce immunity. The present invention enables to give the immunity against the bacterial antigen to the animal at low cost by giving a transgenic plant as food to the animal. For example, the present invention is useful for developing swine edema disease vaccine and cholera vaccine.

The invention claimed is:

1. A hybrid protein comprising:
   (a) two or three toxin proteins selected from the group consisting of Shiga toxin proteins, cholera toxin proteins, *Escherichia coli* heat-labile toxin proteins and combinations thereof, and
   (b) a peptide having the amino acid sequence represented by SEQ ID NO: 2, 82, or 84 or an amino acid sequence which has at least 90% identity to the amino acid sequence represented by SEQ ID NO: 2, 82, or 84 and which is tandemly linked to the C-terminus of each of the toxin proteins, wherein said hybrid protein causes an immune response when administered to an animal.

2. The hybrid protein of claim 1, wherein two of the Shiga toxin proteins, cholera toxin proteins, or *Escherichia coli* heat-labile toxin proteins are tandemly linked through a peptide having the amino acid sequence represented by SEQ ID NO: 2.

3. The hybrid protein of claim 1 or claim 2, wherein each of the toxin proteins is a Shiga toxin protein B subunit.

4. The hybrid protein of claim 1, wherein each of the toxin proteins are Stx2e proteins.

5. The hybrid protein of claim 1, wherein each of the toxin proteins are cholera toxin protein B subunits.

6. The hybrid protein of claim 1, wherein each of the toxin proteins are *Escherichia coli* heat-labile toxin protein B subunits.

7. The hybrid protein of claim 2, which comprises the amino acid sequence represented by SEQ ID NO: 10, 12, 14, or 16.

8. The hybrid protein of claim 1, which comprises the amino acid sequence represented by SEQ ID NO: 86, 88, 90, 92, 94, 96, 98, or 100.

9. The hybrid protein of claim 1, which further comprises a secretory signal peptide derived from a plant at the amino terminus of the hybrid protein.

10. The hybrid protein of claim 9, which further comprises an endoplasmic reticulum retention signal peptide at the carboxyl terminus of the hybrid protein.

11. The hybrid protein of claim 1, which further comprises a chloroplast transit signal peptide at the amino terminus of the hybrid protein.

12. A DNA construct comprising a nucleotide sequence encoding the hybrid protein of claim 1.

13. The DNA construct of claim 12, which comprises a nucleotide sequence having the nucleotide sequence represented by SEQ ID NO: 9, 11, 13, or 15.

14. The DNA construct of claim 12, which comprises a nucleotide sequence having the nucleotide sequence represented by SEQ ID NO: 85, 87, 89, 91, 93, 95, 97, or 99.

15. The DNA construct of claim 12, wherein the nucleotide sequence encoding a hybrid protein is operably-linked to a 5'-untranslated region of an alcohol dehydrogenase gene derived from a plant.

16. The DNA construct of claim 15, wherein the 5'-untranslated region of an alcohol dehydrogenase gene derived from a plant is derived from *Nicotiana tabacum*.

17. The DNA construct of claim 16, which comprises the nucleotide sequence represented by any one of SEQ ID NOS: 24 to 29.

18. The DNA construct of claim 16, which comprises the nucleotide sequence represented by any one of SEQ ID NOS: 101 to 111.

19. A recombinant vector comprising the DNA construct of claim 12.

20. A transformant transformed with the recombinant vector of claim 19.

21. The transformant of claim 20, which is a transformed plant cell or a transformed plant.

22. A peptide having the amino acid sequence represented by one of SEQ ID NO: 2, 82, or 84.

23. The hybrid protein of claim 1, wherein the peptide has the sequence represented by SEQ ID NO: 2.

24. The hybrid protein of claim 1, wherein the peptide has the sequence represented by SEQ ID NO: 82.

25. The hybrid protein of claim 1, wherein the peptide has the sequence represented by SEQ ID NO: 84.

26. The hybrid protein of claim 1, which causes an immune response when administered to pigs.

* * * * *

SEQUENCE LISTING

```
<160> NUMBER OF SEQ ID NOS: 114

<210> SEQ ID NO 1
<211> LENGTH: 36
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 1
agatcccctg gttctggtcc tggttctcct agatcc                                36

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ser Pro Gly Ser Gly Pro Gly Ser Pro Arg Ser
1               5                   10

<210> SEQ ID NO 3
<211> LENGTH: 959
<212> TYPE: DNA
<213> ORGANISM: Escherichia coli

<400> SEQUENCE: 3
atgaagtgta tattgttaaa gtggatactg tgtctgttac tgggtttttc ttcggtatcc         60
tattcccagg agtttacgat agacttttcg actcaacaaa gttatgtatc ttcgttaaat       120
agtatacgga cagcgatatc gacccctctt gaacatatat ctcagggagc tacatcggta       180
tccgttatta atcatacacc accaggaagt tatatttccg taggtatacg agggcttgat       240
gtttatcagg agcgttttga ccatcttcgt ctgattattg aacgaaataa tttatatgtg       300
gctggatttg ttaatacgac aacaaatact ttctacagat tttcagattt gcacatatat       360
cattgcccgg tgtgacaact atttccatga caacggacag cagttatacc actctgcaac       420
gtgtcgcagc gctggaacgt tccggaatgc aaatcagtcg tcactcactg gtttcatcat       480
atctggcgtt aatggagttc agtggtaata caatgaccag agatgcatca agagcagttc       540
tgcgttttgt cactgtcaca gcagaagcct acggttcag gcaaatacag agagaatttc        600
gtctggcact gtctgaaact gctcctgttt atacgatgac gccggaagac gtggacctca       660
ctctgaactg ggggagaatc agcaatgtgc ttccggagta tcggggagag ctggtgtca        720 gagtggggag aatatccttt aataatatat cagcgatact tggtactgtg ccgttatac        780 tgaattgcca tcatcagggc gcacgttctg ttcgcgccgt gaatgaagag agtcaaccag       840
aatgtcagat aactggcgac aggcccgtta taaaaataaa caatacatta tgggaaagta       900
atacagcagc agcgtttctg aacagaaagt cacagccttt atatacaact ggtgaatga        959

<210> SEQ ID NO 4
<211> LENGTH: 304
<212> TYPE: PRT
<213> ORGANISM: Escherichia coli

<400> SEQUENCE: 4

Met Lys Cys Ile Leu Leu Lys Trp Ile Leu Cys Leu Leu Leu Gly Phe
1               5                   10                  15

Ser Ser Val Ser Tyr Ser Gln Glu Phe Thr Ile Asp Phe Ser Thr Gln
                20                  25                  30

Gln Ser Tyr Val Ser Ser Leu Asn Ser Ala Ile Ser Thr Pro Leu Glu
            35                  40                  45
```

His Ile Ser Gln Gly Ala Thr Ser Val Ser Val Ile Asn His Thr Pro
            50                  55                  60

Pro Gly Ser Tyr Ile Ser Val Gly Ile Arg Gly Leu Asp Val Tyr Gln
 65                  70                  75                  80

Glu Arg Phe Asp His Leu Arg Leu Ile Ile Glu Arg Asn Asn Leu Tyr
                 85                  90                  95

Phe Val Asn Thr Thr Asn Thr Phe Tyr Arg Phe Ser Asp Phe Ala
                100                 105                 110

His Ile Ser Leu Pro Gly Val Thr Thr Ile Ser Met Thr Thr Asp Ser
                115                 120                 125

Ser Tyr Thr Thr Leu Gln Arg Val Ala Ala Leu Glu Arg Ser Gly Met
    130                 135                 140

Gln Ile Ser Arg His Ser Leu Tyr Leu Ala Leu Met Glu Phe Ser Gly
145                 150                 155                 160

Asn Thr Met Thr Arg Asp Ala Ser Arg Ala Val Leu Arg Phe Val Thr
                165                 170                 175

Val Thr Ala Glu Ala Leu Arg Phe Arg Gln Ile Gln Arg Glu Phe Arg
                180                 185                 190

Leu Ala Leu Ser Glu Thr Ala Pro Val Tyr Thr Met Thr Pro Asp Leu
                195                 200                 205

Thr Leu Asn Trp Gly Arg Ile Ser Asn Val Leu Pro Glu Tyr Arg Gly
    210                 215                 220

Glu Ala Gly Val Arg Val Gly Arg Ile Ser Phe Asn Asn Ile Ser Ala
225                 230                 235                 240

Ile Leu Gly Thr Val Ala Val Ile Leu Asn Cys His His Gln Gly Ala
                245                 250                 255

Arg Ser Val Arg Ala Glu Ser Gln Pro Glu Cys Gln Ile Thr Gly Asp
                260                 265                 270

Arg Pro Val Ile Lys Ile Asn Asn Thr Leu Trp Glu Ser Asn Thr Ala
                275                 280                 285

Ala Ala Phe Leu Asn Arg Lys Ser Gln Pro Leu Tyr Thr Thr Gly Glu
    290                 295                 300

<210> SEQ ID NO 5
<211> LENGTH: 210
<212> TYPE: DNA
<213> ORGANISM: Escherichia coli

<400> SEQUENCE: 5
gcggcggatt gtgctaaagg taaaattgag ttttccaagt ataatgagga ataccttt      60 actgtgaagg tgtcaggaag agaatactgg acgaacagat ggaatttgca gccattgtta  120
caaagtgctc agctgacagg gatgactgta acaatcatat ctaatacctg cagttcaggc  180
tcaggctttg cccaggtgaa gtttaactga                                    210

<210> SEQ ID NO 6
<211> LENGTH: 69
<212> TYPE: PRT
<213> ORGANISM: Escherichia coli

<400> SEQUENCE: 6

Ala Ala Asp Cys Ala Lys Gly Lys Ile Glu Phe Ser Lys Tyr Asn Glu
 1               5                  10                  15

Asp Asn Thr Phe Thr Val Lys Val Ser Gly Arg Glu Tyr Trp Thr Asn
                20                  25                  30

Arg Trp Asn Leu Gln Pro Leu Leu Gln Ser Ala Gln Leu Thr Gly Met

```
                35                  40                  45
Thr Val Thr Ile Ile Ser Asn Thr Cys Ser Ser Gly Ser Gly Phe Ala
        50                  55                  60

Gln Val Lys Phe Asn
65
```

<210> SEQ ID NO 7
<211> LENGTH: 312
<212> TYPE: DNA
<213> ORGANISM: Vibrio cholerae

<400> SEQUENCE: 7

```
acccccccaga acatcaccga cctctgcgcc gagagccaca acacccaaat ctacaccctc      60
aacgacaaga ttttcagcta caccgagagc ctcgccggca agagggagat ggccatcatc     120
accttcaaga acggcgccat cttccaggtc gaggtccccg gcagccagca catcgacagc     180
cagaagaagg ccatcgagag gatgaaggac accctcagga tcgcctacct caccgaggcc     240
aaggtcgaga agctctgcgt ctggaacaac aagaccccc acgccatcgc cgccatcagc      300
atggccaact ga                                                         312
```

<210> SEQ ID NO 8
<211> LENGTH: 103
<212> TYPE: PRT
<213> ORGANISM: Vibrio cholerae

<400> SEQUENCE: 8

```
Thr Pro Gln Asn Ile Thr Asp Leu Cys Ala Glu Ser His Asn Thr Gln
1               5                  10                  15

Ile Tyr Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Ile Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn
            100
```

<210> SEQ ID NO 9
<211> LENGTH: 453
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
gcggcggatt gtgctaaagg taaaattgag ttttccaagt ataatgagga taataccttt      60
actgtgaagg tgtcaggaag agaatactgg acgaacagat ggaatttgca gccattgtta     120
caaagtgctc agctgacagg gatgactgta acaatcatat ctaataccgg cagttcaggc     180
tcaggctttg cccaggtgaa gtttaacaga tcccctggtt ctggtcctgg ttctcctaga     240 tccgcggcg attgtgctaa aggtaaaatt gagttttcca gtataatga ggataatacc      300 tttactgtga aggtgtcagg aagagaatac tggacgaaca gatggaattt gcagccattg     360
```
ttacaaagtg ctcagctgac agggatgact gtaacaatca tatctaatac ctgcagttca    420
ggctcaggct ttgcccaggt gaagtttaac tga                                 453

<210> SEQ ID NO 10
<211> LENGTH: 150
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ala Ala Asp Cys Ala Lys Gly Lys Ile Glu Phe Ser Lys Tyr Asn Glu
1               5                   10                  15

Asp Asn Thr Phe Thr Val Lys Val Ser Gly Arg Glu Tyr Trp Thr Asn
            20                  25                  30

Arg Trp Asn Leu Gln Pro Leu Leu Gln Ser Ala Gln Leu Thr Gly Met
        35                  40                  45

Thr Val Thr Ile Ile Ser Asn Thr Cys Ser Ser Gly Ser Gly Phe Ala
    50                  55                  60

Gln Val Lys Phe Asn Arg Ser Pro Gly Ser Gly Pro Gly Ser Pro Arg
65                  70                  75                  80

Ser Ala Ala Asp Cys Ala Lys Gly Lys Ile Glu Phe Ser Lys Tyr Asn
                85                  90                  95

Glu Asp Asn Thr Phe Thr Val Lys Val Ser Gly Arg Glu Tyr Trp Thr
            100                 105                 110

Asn Arg Trp Asn Leu Gln Pro Leu Leu Gln Ser Ala Gln Leu Thr Gly
        115                 120                 125

Met Thr Val Thr Ile Ile Ser Asn Thr Cys Ser Ser Gly Ser Gly Phe
    130                 135                 140

Ala Gln Val Lys Phe Asn
145                 150

<210> SEQ ID NO 11
<211> LENGTH: 657
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11 acccccaga acatcaccga cctctgcgcc gagagccaca cacccaaat ctacaccctc       60 aacgacaaga ttttcagcta caccgagagc ctcgccggca agagggagat ggccatcatc    120
accttcaaga acggcgccat cttccaggtc gaggtccccg gcagccagca catcgacagc    180
cagaagaagg ccatcgagag gatgaaggac accctcagga tcgcctacct caccgaggcc    240
aaggtcgaga gctctgcgt ctggaacaac aagaccccc acgccatcgc cgccatcagc     300
atggccaaca gatcccctgg ttctggtcct ggttctccta gatccacccc ccagaacatc    360
accgacctct gcgccgagag ccacaacacc caaatctaca ccctcaacga caagattttc    420
agctacaccg agagcctcgc cggcaagagg gagatggcca tcatcacctt caagaacggc    480
gccatcttcc aggtcgaggt ccccggcagc cagcacatcg acagccagaa gaaggccatc    540
gagaggatga aggacaccct caggatcgcc tacctcaccg aggccaaggt cgagaagctc    600
tgcgtctgga caacaagac cccccacgcc atcgccgcca tcagcatggc caactga       657

<210> SEQ ID NO 12
<211> LENGTH: 218
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

Thr Pro Gln Asn Ile Thr Asp Leu Cys Ala Glu Ser His Asn Thr Gln
1               5                   10                  15

Ile Tyr Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Ile Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn Arg Ser Pro Gly Ser Gly Pro Gly Ser
            100                 105                 110

Pro Arg Ser Thr Pro Gln Asn Ile Thr Asp Leu Cys Ala Glu Ser His
        115                 120                 125

Asn Thr Gln Ile Tyr Thr Leu Asn Asp Lys Ile Phe Ser Tyr Thr Glu
    130                 135                 140

Ser Leu Ala Gly Lys Arg Glu Met Ala Ile Ile Thr Phe Lys Asn Gly
145                 150                 155                 160

Ala Ile Phe Gln Val Glu Val Pro Gly Ser Gln His Ile Asp Ser Gln
                165                 170                 175

Lys Lys Ala Ile Glu Arg Met Lys Asp Thr Leu Arg Ile Ala Tyr Leu
            180                 185                 190

Thr Glu Ala Lys Val Glu Lys Leu Cys Val Trp Asn Asn Lys Thr Pro
        195                 200                 205

His Ala Ile Ala Ala Ile Ser Met Ala Asn
    210                 215

<210> SEQ ID NO 13
<211> LENGTH: 489
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 13
gcggcggatt gtgctaaagg taaaattgag ttttccaagt ataatgagga taatacctt      60 actgtgaagg tgtcaggaag agaatactgg acgaacagat ggaatttgca gccattgtta    120
caaagtgctc agctgacagg gatgactgta acaatcatat ctaatacctg cagttcaggc    180
tcaggctttg cccaggtgaa gtttaacaga tcccctggtt ctggtcctgg ttctcctaga    240
tccgcggcgg attgtgctaa aggtaaaatt gagttttcca gtataatgag gataatacc     300 tttactgtga aggtgtcagg aagagaatac tggacgaaca gatggaattt gcagccattg    360
ttacaaagtg ctcagctgac agggatgact gtaacaatca tatctaatac ctgcagttca    420
ggctcaggct tgcccaggt gaagtttaac agatcccctg gttctggtcc tggttctcct    480
agatcttga                                                                  489

<210> SEQ ID NO 14
<211> LENGTH: 162
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ala Ala Asp Cys Ala Lys Gly Lys Ile Glu Phe Ser Lys Tyr Asn Glu
1               5                   10                  15

Asp Asn Thr Phe Thr Val Lys Val Ser Gly Arg Glu Tyr Trp Thr Asn
            20                  25                  30

Arg Trp Asn Leu Gln Pro Leu Leu Gln Ser Ala Gln Leu Thr Gly Met
        35                  40                  45

Thr Val Thr Ile Ile Ser Asn Thr Cys Ser Ser Gly Ser Gly Phe Ala
    50                  55                  60

Gln Val Lys Phe Asn Arg Ser Pro Gly Ser Gly Pro Gly Ser Pro Arg
65                  70                  75                  80

Ser Ala Ala Asp Cys Ala Lys Gly Lys Ile Glu Phe Ser Lys Tyr Asn
                85                  90                  95

Glu Asp Asn Thr Phe Thr Val Lys Val Ser Gly Arg Glu Tyr Trp Thr
            100                 105                 110

Asn Arg Trp Asn Leu Gln Pro Leu Leu Gln Ser Ala Gln Leu Thr Gly
        115                 120                 125

Met Thr Val Thr Ile Ile Ser Asn Thr Cys Ser Ser Gly Ser Gly Phe
    130                 135                 140

Ala Gln Val Lys Phe Asn Arg Ser Pro Gly Ser Gly Pro Gly Ser Pro
145                 150                 155                 160

Arg Ser

<210> SEQ ID NO 15
<211> LENGTH: 693
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15 acccccaga acatcaccga cctctgcgcc gagagccaca cacccaaat ctacaccctc        60 aacgacaaga ttttcagcta caccgagagc ctcgccggca agagggagat ggccatcatc     120
accttcaaga acggcgccat cttccaggtc gaggtccccg gcagccagca catcgacagc     180
cagaagaagg ccatcgagag gatgaaggac accctcagga tcgcctacct caccgaggcc     240
aaggtcgaga agctctgcgt ctggaacaac aagaccccc acgccatcgc cgccatcagc      300
atggccaaca gatccctgg ttctggtcct ggttctccta gatccacccc ccagaacatc       360
accgacctct cgccgagag ccacaacacc caaatctaca ccctcaacga caagattttc       420
agctacaccg agagcctcgc cggcaagagg gagatggcca tcatcacctt caagaacggc     480
gccatcttcc aggtcgaggt ccccggcagc cagcacatcg acagccagaa gaaggccatc     540
gagaggatga aggacaccct caggatcgcc tacctcaccg aggccaaggt cgagaagctc     600
tgcgtctgga acaacaagac ccccacgcc atcgccgcca tcagcatggc caacagatcc       660
cctggttctg gtcctggttc tcctagatct tga                              693

<210> SEQ ID NO 16
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Thr Pro Gln Asn Ile Thr Asp Leu Cys Ala Glu Ser His Asn Thr Gln
1               5                   10                  15

Ile Tyr Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Ile Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn Arg Ser Pro Gly Ser Gly Pro Gly Ser
            100                 105                 110

Pro Arg Ser Thr Pro Gln Asn Ile Thr Asp Leu Cys Ala Glu Ser His
        115                 120                 125

Asn Thr Gln Ile Tyr Thr Leu Asn Asp Lys Ile Phe Ser Tyr Thr Glu
    130                 135                 140

Ser Leu Ala Gly Lys Arg Glu Met Ala Ile Ile Thr Phe Lys Asn Gly
145                 150                 155                 160

Ala Ile Phe Gln Val Glu Val Pro Gly Ser Gln His Ile Asp Ser Gln
                165                 170                 175

Lys Lys Ala Ile Glu Arg Met Lys Asp Thr Leu Arg Ile Ala Tyr Leu
            180                 185                 190

Thr Glu Ala Lys Val Glu Lys Leu Cys Val Trp Asn Asn Lys Thr Pro
        195                 200                 205

His Ala Ile Ala Ala Ile Ser Met Ala Asn Arg Ser Pro Gly Ser Gly
    210                 215                 220

Pro Gly Ser Pro Arg Ser
225                 230

<210> SEQ ID NO 17
<211> LENGTH: 72
<212> TYPE: DNA
<213> ORGANISM: Nicotiana tabacum

<400> SEQUENCE: 17
atggggagaa tgtcaatacc catgatgggt tttgtggtgt tatgtctatg ggcagtggta    60
gcagaaggat cc                                                        72

<210> SEQ ID NO 18
<211> LENGTH: 24
<212> TYPE: PRT
<213> ORGANISM: Nicotiana tabacum

<400> SEQUENCE: 18

Met Gly Arg Met Ser Ile Pro Met Met Gly Phe Val Val Leu Cys Leu

```
1               5                   10                  15
Trp Ala Val Val Ala Glu Gly Ser
                20
```

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Lys Asp Glu Leu
1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

His Asp Glu Leu
1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys Asp Glu Phe
1

<210> SEQ ID NO 22
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

His Asp Glu Phe
1

<210> SEQ ID NO 23
<211> LENGTH: 91
<212> TYPE: DNA
<213> ORGANISM: Nicotiana tabacum

<400> SEQUENCE: 23
tatttaactc agtattcaga aacaacaaaa gttcttctct acataaaatt ttcctatttt    60
agtgatcagt gaaggaaatc aagaaaaata a                                  91

<210> SEQ ID NO 24
<211> LENGTH: 547
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 24

```
tatttaactc agtattcaga acaacaaaa gttcttctct acataaaatt ttcctatttt      60
agtgatcagt gaaggaaatc aagaaaaata aatggcggcg gattgtgcta aaggtaaaat    120
tgagttttcc aagtataatg aggataaatac ctttactgtg aaggtgtcag gaagagaata   180
ctggacgaac agatggaatt tgcagccatt gttacaaagt gctcagctga cagggatgac   240
tgtaacaatc atatctaata cctgcagttc aggctcaggc tttgcccagg tgaagtttaa   300
cagatcccct ggtctggtc ctggttctcc tagatccgcg gcggattgtg ctaaaggtaa    360
aattgagttt ccaagtata atgaggataa tacctttact gtgaaggtgt caggaagaga   420
atactggacg aacagatgga atttgcagcc attgttacaa agtgctcagc tgacagggat   480
gactgtaaca atcatatcta atacctgcag ttcaggctca ggctttgccc aggtgaagtt   540
taactga                                                             547
```

<210> SEQ ID NO 25
<211> LENGTH: 751
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
tatttaactc agtattcaga acaacaaaa gttcttctct acataaaatt ttcctatttt      60
agtgatcagt gaaggaaatc aagaaaaata aatgaccccc cagaacatca ccgacctctg   120
cgccgagagc cacaacaccc aaatctacac cctcaacgac aagatttca gctacaccga   180
gagcctcgcc ggcaagaggg agatggccat catcaccttc aagaacggcg ccatcttcca   240
ggtcgaggtc cccggcagcc agcacatcga cagccagaag aaggccatcg agaggatgaa   300
ggacaccctc aggatcgcct acctcaccga ggccaaggtc gagaagctct gcgtctggaa   360
caacaagacc ccccacgcca tcgccgccat cagcatggcc aacagatccc ctggttctgg   420
tcctggttct cctagatcca ccccccagaa catcaccgac ctctgcgccg agagccacaa   480
cacccaaatc tacaccctca cgacaagat tttcagctac accgagagcc tcgccggcaa   540
gagggagatg gccatcatca ccttcaagaa cggcgccatc ttccaggtcg aggtccccgg   600
cagccagcac atcgacagcc agaagaaggc catcgagagg atgaaggaca ccctcaggat   660
cgcctacctc accgaggcca aggtcgagaa gctctgcgtc tggaacaaca gaccccccca   720
cgccatcgcc gccatcagca tggccaactg a                                  751
```

<210> SEQ ID NO 26
<211> LENGTH: 637
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26

```
tatttaactc agtattcaga acaacaaaa gttcttctct acataaaatt ttcctatttt      60
agtgatcagt gaaggaaatc aagaaaaata aatgggaga atgtcaatac ccatgatggg   120
ttttgtggtg ttatgtctat gggcagtggt agcagaagga tccgcggcgg attgtgctaa   180
```

```
aggtaaaatt gagttttcca agtataatga ggataatacc tttactgtga aggtgtcagg      240
aagagaatac tggacgaaca gatggaattt gcagccattg ttacaaagtg ctcagctgac      300
agggatgact gtaacaatca tatctaatac ctgcagttca ggctcaggct ttgcccaggt      360
gaagtttaac agatcccctg gttctggtcc tggttctcct agatccgcgg cggattgtgc      420
taaaggtaaa attgagtttt ccaagtataa tgaggataat acctttactg tgaaggtgtc      480
aggaagagaa tactggacga acagatggaa tttgcagcca ttgttacaaa gtgctcagct      540
gacagggatg actgtaacaa tcatatctaa tacctgcagt tcaggctcag gctttgccca      600
ggtgaagttt aacagatctg aacatgatga attgtga                              637

<210> SEQ ID NO 27
<211> LENGTH: 841
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
tatttaactc agtattcaga acaacaaaa gttcttctct acataaaatt ttcctatttt       60
agtgatcagt gaaggaaatc aagaaaaata aatggggaga atgtcaatac ccatgatggg     120
ttttgtggtg ttatgtctat gggcagtggt agcagaagga tccacccccc agaacatcac     180
cgacctctgc gccgagagcc acaacaccca atctacacc ctcaacgaca gatttttcag     240
ctacaccgag agcctcgccg gcaagaggga gatggccatc atccacttca gaacggcgc      300 catcttccag gtcgaggtcc ccggcagcca gcacatcgac agccagaaga aggccatcga     360
gaggatgaag gacacccctca ggatcgccta cctcaccgag gccaaggtcg agaagctctg     420
cgtctggaac aacaagaccc cccacgccat cgccgccatc agcatggcca acagatcccc     480
tggttctggt cctggttctc ctagatccac ccccagaac atcaccgacc tctgcgccga     540
gagccacaac acccaaatct acacctcaa cgacaagatt tcagctaca ccgagagcct      600 cgccggcaag agggagatgg ccatcatcac cttcaagaac ggcgccatct tccaggtcga     660
ggtccccggc agccagcaca tcgacagcca gaagaaggcc atcgagagga tgaaggacac     720
cctcaggatc gcctacctca ccgaggccaa ggtcgagaag ctctgcgtct ggaacaacaa     780
gaccccccac gccatcgccg ccatcagcat ggccaacaga tctgaacatg atgaattgtg     840
a                                                                     841

<210> SEQ ID NO 28
<211> LENGTH: 667
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 28
tatttaactc agtattcaga acaacaaaa gttcttctct acataaaatt ttcctatttt       60
agtgatcagt gaaggaaatc aagaaaaata atggggaga atgtcaatac ccatgatggg      120
ttttgtggtg ttatgtctat gggcagtggt agcagaagga tccgcggcgg attgtgctaa     180
aggtaaaatt gagttttcca agtataatga ggataatacc tttactgtga aggtgtcagg    240
aagagaatac tggacgaaca gatggaattt gcagccattg ttacaaagtg ctcagctgac    300
agggatgact gtaacaatca tatctaatac ctgcagttca ggctcaggct ttgcccaggt    360
```

```
gaagtttaac agatcccctg gttctggtcc tggttctcct agatccgcgg cggattgtgc    420
taaaggtaaa attgagtttt ccaagtataa tgaggataat accttactg tgaaggtgtc     480 aggaagagaa tactggacga acagatggaa tttgcagcca ttgttacaaa gtgctcagct    540
gacagggatg actgtaacaa tcatatctaa tacctgcagt tcaggctcag gctttgccca    600
ggtgaagttt aacagatccc tggttctgg tcctggttct cctagatctg aacatgatga     660
attgtga                                                              667
```

<210> SEQ ID NO 29  
<211> LENGTH: 871  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 29

```
tatttaactc agtattcaga acaacaaaa gttcttctct acataaaatt ttcctatttt     60
agtgatcagt gaaggaaatc aagaaaaata aatggggaga atgtcaatac ccatgatggg   120
ttttgtggtg ttatgtctat gggcagtggt agcagaagga tccacccccc agaacatcac   180
cgacctctgc gccgagagcc acaacaccca atctacacc ctcaacgaca gattttcag    240 ctacaccgag agcctcgccg gcaagaggga gatggccatc atccttca agaacggcgc    300 catcttccag gtcgaggtcc ccggcagcca gcacatcgac agccagaaga aggccatcga   360
gaggatgaag gacaccctca ggatcgccta cctcaccgag gccaaggtcg agaagctctg   420
cgtctggaac aacaagaccc ccacgccat cgccgccatc agcatggcca acagatcccc    480
tggttctggt cctggttctc ctagatccac ccccagaac atcaccgacc tctgcgccga    540
gagccacaac acccaaatct acaccctcaa cgacaagatt ttcagctaca ccgagagcct   600
cgccggcaag agggagatgg ccatcatcac cttcaagaac ggcgccatct tccaggtcga   660
ggtccccggc agccagcaca tcgacagcca gaagaaggcc atcgagagga tgaaggacac   720
cctcaggatc gcctacctca ccgaggccaa ggtcgagaag ctctgcgtct ggaacaacaa   780
gaccccccac gccatcgccg ccatcagcat ggccaacaga tcccctggtt ctggtcctgg   840
ttctcctaga tctgaacatg atgaattgtg a                                  871
```

<210> SEQ ID NO 30  
<211> LENGTH: 38  
<212> TYPE: DNA  
<213> ORGANISM: Artificial Sequence  
<220> FEATURE:  
<223> OTHER INFORMATION: Description of Artificial Sequence: Synthetic primer

<400> SEQUENCE: 30

```
tatctagagc caccatggga tccgcggcgg attgtgct                            38
```

<210> SEQ ID NO 31  
<211> LENGTH: 30  
<212> TYPE: DNA  
<213> ORGANISM: Artificial Sequence  
<220> FEATURE:  
<223> OTHER INFORMATION: Description of Artificial Sequence: Synthetic primer

<400> SEQUENCE: 31

```
ttcaagatct gttaaacttc acctgggcaa                                     30
```

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gtcgacggta cccccgggga gct                                              23

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33 ccccggggt accgtcgaca gct                                               23

<210> SEQ ID NO 34
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
aatctagagt ctatttaact cagtattcag aaacaacaaa a                          41

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
aaatgcatta tttttcttga tttccttcac                                       30

<210> SEQ ID NO 36
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
aaatgcatgg ggagaatgtc aatacccatg                                       30

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tataggatcc cattatttt cttgatttcc                                        30

```
<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Ser Glu His Asp Glu Leu
1               5

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gatctgaaca tgatgaattg t                                            21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gatcacaatt catcatgttc a                                            21

<210> SEQ ID NO 41
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gatcttatcc ttatgattat cctgattatg ctg                               33

<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gatccagcat aatcaggata atcataagga taa                               33

<210> SEQ ID NO 43
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gatcccctgg ttctggtcct ggttctccta                                   30
```

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gatctaggag aaccaggacc agaaccaggg                                      30

<210> SEQ ID NO 45
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ttggatccac cccccagaac atcaccgacc tctgcgccga                           40

<210> SEQ ID NO 46
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
cgttgagggt gtagatttgg gtgttgtggc tctcggcgc                            39

<210> SEQ ID NO 47
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ccctcaacga caagattttc agctacaccg agagcctcgc                           40

<210> SEQ ID NO 48
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cttgaaggtg atgatggcca tctccctctt gccggcgagg                           40

<210> SEQ ID NO 49
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
caccttcaag aacggcgcca tcttccaggt cg                                   32

<210> SEQ ID NO 50
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
cttctggctg tcgatgtgct ggctgccggg gacctcgacc tggaa    45

<210> SEQ ID NO 51
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
agccagaaga aggccatcga gaggatgaag gacaccctca ggatc    45

<210> SEQ ID NO 52
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
gcagagcttc tcgaccttgg cctcggtgag gtaggcgatc ctg    43

<210> SEQ ID NO 53
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
aagctctgcg tctggaacaa caagaccccc    30

<210> SEQ ID NO 54
<211> LENGTH: 45
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
aaagatctgt tggccatgct gatggcggcg atggcgtggg gggtc    45

<210> SEQ ID NO 55
<211> LENGTH: 31
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
tttggatcca gcaagggcga ggagctgttc a    31

<210> SEQ ID NO 56

```
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tttagatctc ttgtacagct cgtccatgcc gag                                   33

<210> SEQ ID NO 57
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
aaaggatccg cctcctccga ggacgtcatc                                       30

<210> SEQ ID NO 58
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
aaaagatctg gcgccggtgg agtggcggcc                                       30

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gatcaaaatg gggttgtcat tcggaaagtt                                       30

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
attccatcta tgccttgctt gcgatgttgt                                       30

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ctagacaaga tccgtccatt gtgg                                             24

<210> SEQ ID NO 62
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62 accccaaca tcccacacgg tgaa                                              24

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Ser Pro Gly Ser Arg Ser
1               5

<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Ser Gly Ser Gly Ser Gly Ser Gly Ser Arg Ser
1               5                   10

<210> SEQ ID NO 65
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gatcccctgg ttcca                                                       15

<210> SEQ ID NO 66
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gatctggaac caggg                                                       15

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
gatccggttc tggttctggt tctggttcca                                       30

<210> SEQ ID NO 68
```

```
<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gatctggaac cagaaccaga accagaaccg                                           30

<210> SEQ ID NO 69
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
gtgatcagtg aaggaaatca agaaa                                                25

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
cataacacca caaaacccat cat                                                  23

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ccaagccaaa gaagatcaag ca                                                   22

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ccctgaatca tcgaccttgt agaa                                                 24

<210> SEQ ID NO 73
<211> LENGTH: 700
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
tatttaactc agtattcaga aacaacaaaa gttcttctct acataaaatt ttcctatttt          60
agtgatcagt gaaggaaatc aagaaaaata aatggggaga atgtcaatac ccatgatggg         120
ttttgtggtg ttatgtctat gggcagtggt agcagaagga tccgcggcgg attgtgctaa        180
```

```
aggtaaaatt gagttttcca agtataatga ggataatacc tttactgtga aggtgtcagg    240
aagagaatac tggacgaaca gatggaattt gcagccattg ttacaaagtg ctcagctgac    300
agggatgact gtaacaatca tatctaatac ctgcagttca ggctcaggct ttgcccaggt    360
gaagtttaac agatcccctg gttctggtcc tggttctcct agatccgcgg cggattgtgc    420
taaaggtaaa attgagtttt ccaagtataa tgaggataat acctttactg tgaaggtgtc    480
aggaagagaa tactggacga acagatggaa tttgcagcca ttgttacaaa gtgctcagct    540
gacagggatg actgtaacaa tcatatctaa tacctgcagt tcaggctcag gctttgccca    600
ggtgaagttt aacagatccc ctggttctgg tcctggttct cctagatctt atccttatga    660
ttatcctgat tatgctggat ctgaacatga tgaattgtga                          700
```

```
<210> SEQ ID NO 74
<211> LENGTH: 904
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
tatttaactc agtattcaga acaacaaaa gttcttctct acataaaatt ttcctatttt      60
agtgatcagt gaaggaaatc aagaaaaata aatggggaga atgtcaatac ccatgatggg   120
ttttgtggtg ttatgtctat gggcagtggt agcagaagga tccaccccccc agaacatcac   180 cgacctctgc gccgagagcc acaacaccca aatctacacc ctcaacgaca agattttcag   240
ctacaccgag agcctcgccg gcaagaggga gatggccatc atccacttca agaacggcgc   300
catcttccag gtcgaggtcc ccggcagcca gcacatcgac agccagaaga aggccatcga   360
gaggatgaag gacacccctca ggatcgccta cctcaccgag gccaaggtcg agaagctctg   420
cgtctggaac aacaagaccc cccacgccat cgccgccatc agcatggcca acagatcccc   480
tggttctggt cctggttctc ctagatccac ccccagaac atcaccgacc tctgcgccga   540
gagccacaac acccaaatct acaccctcaa cgacaagatt ttcagctaca ccgagagcct   600
cgccggcaag agggagatgg ccatcatcac cttcaagaac ggcgccatct tccaggtcga   660 ggtcccggc agccagcaca tcgacagcca gaagaaggcc atcgagagga tgaaggacac   720
cctcaggatc gcctacctca ccgaggccaa ggtcgagaag ctctgcgtct ggaacaacaa   780
gaccccccac gccatcgccg ccatcagcat ggccaacaga tccccctggtt ctggtcctgg   840 ttctcctaga tcttatcctt atgattatcc tgattatgct ggatctgaac atgatgaatt   900
gtga                                                                904
```

```
<210> SEQ ID NO 75
<211> LENGTH: 21
<212> TYPE: DNA
<213> ORGANISM: Nicotiana tabacum

<400> SEQUENCE: 75
gatttgttgg ttgatactat g                                               21
```

```
<210> SEQ ID NO 76
<211> LENGTH: 7
<212> TYPE: PRT
<213> ORGANISM: Nicotiana tabacum

<400> SEQUENCE: 76
```

```
Asp Leu Leu Val Asp Thr Met
1               5

<210> SEQ ID NO 77
<211> LENGTH: 45
<212> TYPE: DNA
<213> ORGANISM: Armoracia rusticana

<400> SEQUENCE: 77
ctactccatg atatggtgga ggtcgttgac tttgttagct ctatg              45

<210> SEQ ID NO 78
<211> LENGTH: 15
<212> TYPE: PRT
<213> ORGANISM: Armoracia rusticana

<400> SEQUENCE: 78

Leu Leu His Asp Met Val Glu Val Val Asp Phe Val Ser Ser Met
1               5                   10                  15

<210> SEQ ID NO 79
<211> LENGTH: 75
<212> TYPE: PRT
<213> ORGANISM: Lactuca sativa

<400> SEQUENCE: 79

Met Ala Ser Ile Ser Ser Ser Ala Ile Ala Thr Val Asn Arg Thr Thr
1               5                   10                  15

Ser Thr Gln Ala Ser Leu Ala Ala Pro Phe Thr Gly Leu Lys Ser Asn
            20                  25                  30

Val Ala Phe Pro Val Thr Lys Lys Ala Asn Asn Asp Phe Ser Ser Leu
        35                  40                  45

Pro Ser Asn Gly Gly Arg Val Gln Cys Met Lys Val Trp Pro Pro Ile
    50                  55                  60

Gly Leu Lys Lys Tyr Glu Thr Leu Ser Tyr Leu
65                  70                  75

<210> SEQ ID NO 80
<211> LENGTH: 225
<212> TYPE: DNA
<213> ORGANISM: Lactuca sativa

<400> SEQUENCE: 80
atggcctcca tctcctcctc agccatcgcc accgtcaacc ggaccacctc cacccaagct    60
agcttggcag ctccattcac cggcctcaag tctaacgtag cttttcccagt taccaagaag   120 gctaacaatg acttttcatc cctacccagc aacggtggaa gagtacaatg catgaaggtg   180
tggccaccaa ttgggttgaa gaagtacgag actctttcat accta                   225

<210> SEQ ID NO 81
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81 agatccctg gttctggtcc tggttctcct agatccctg gttccagatc t               51

<210> SEQ ID NO 82
```

<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Ser Pro Gly Ser Gly Pro Gly Ser Pro Arg Ser Pro Gly Ser Arg
1               5                   10                  15

Ser

<210> SEQ ID NO 83
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
agatcccctg gttctggtcc tggttctcct agatcccctg gttctggtcc tggttctcct    60
agatct                                                               66

<210> SEQ ID NO 84
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Ser Pro Gly Ser Gly Pro Gly Ser Pro Arg Ser Pro Gly Ser Gly
1               5                   10                  15

Pro Gly Ser Pro Arg Ser
            20

<210> SEQ ID NO 85
<211> LENGTH: 696
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
gcggcggatt gtgctaaagg taaaattgag ttttccaagt ataatgagga taatacctttt    60 actgtgaagg tgtcaggaag agaatactgg acgaacagat ggaatttgca gccattgtta   120
caaagtgctc agctgacagg gatgactgta acaatcatat ctaatacctg cagttcaggc   180
tcaggctttg cccaggtgaa gtttaacaga tcccctggtt ctggtcctgg ttctcctaga   240
tccgcggcgg attgtgctaa aggtaaaatt gagttttcca agtataatga ggataatacc   300
tttactgtga aggtgtcagg aagagaatac tggacgaaca gatggaattt gcagccattg   360
ttacaaagtg ctcagctgac agggatgact gtaacaatca tatctaatac ctgcagttca   420
ggctcaggct tgcccaggt gaagtttaac agatcccctg gttctggtcc tggttctcct   480
agatccgcgg cggattgtgc taaaggtaaa attgagtttt ccaagtataa tgaggataat   540
acctttactg tgaaggtgtc aggaagagaa tactggacga acagatggaa tttgcagcca   600
ttgttacaaa gtgctcagct gacagggatg actgtaacaa tcatatctaa tacctgcagt   660
tcaggctcag gctttgccca ggtgaagttt aactga                                696

<210> SEQ ID NO 86
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Ala Ala Asp Cys Ala Lys Gly Lys Ile Glu Phe Ser Lys Tyr Asn Glu
1               5                   10                  15

Asp Asn Thr Phe Thr Val Lys Val Ser Gly Arg Glu Tyr Trp Thr Asn
            20                  25                  30

Arg Trp Asn Leu Gln Pro Leu Leu Gln Ser Ala Gln Leu Thr Gly Met
        35                  40                  45

Thr Val Thr Ile Ile Ser Asn Thr Cys Ser Ser Gly Ser Gly Phe Ala
    50                  55                  60

Gln Val Lys Phe Asn Arg Ser Pro Gly Ser Gly Pro Gly Ser Pro Arg
65                  70                  75                  80

Ser Ala Ala Asp Cys Ala Lys Gly Lys Ile Glu Phe Ser Lys Tyr Asn
                85                  90                  95

Glu Asp Asn Thr Phe Thr Val Lys Val Ser Gly Arg Glu Tyr Trp Thr
            100                 105                 110

Asn Arg Trp Asn Leu Gln Pro Leu Leu Gln Ser Ala Gln Leu Thr Gly
        115                 120                 125

Met Thr Val Thr Ile Ile Ser Asn Thr Cys Ser Ser Gly Ser Gly Phe
    130                 135                 140

Ala Gln Val Lys Phe Asn Arg Ser Pro Gly Ser Gly Pro Gly Ser Pro
145                 150                 155                 160

Arg Ser Ala Ala Asp Cys Ala Lys Gly Lys Ile Glu Phe Ser Lys Tyr
                165                 170                 175

Asn Glu Asp Asn Thr Phe Thr Val Lys Val Ser Gly Arg Glu Tyr Trp
            180                 185                 190

Thr Asn Arg Trp Asn Leu Gln Pro Leu Leu Gln Ser Ala Gln Leu Thr
        195                 200                 205

Gly Met Thr Val Thr Ile Ile Ser Asn Thr Cys Ser Ser Gly Ser Gly
    210                 215                 220

Phe Ala Gln Val Lys Phe Asn
225                 230

<210> SEQ ID NO 87
<211> LENGTH: 732
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
gcggcggatt gtgctaaagg taaaattgag ttttccaagt ataatgagga taataccttt    60
actgtgaagg tgtcaggaag agaatactgg acgaacagat ggaatttgca gccattgtta   120
caaagtgctc agctgacagg gatgactgta acaatcatat ctaataccctg cagttcaggc   180 tcaggctttg cccaggtgaa gtttaacaga tcccctggtt ctggtcctgg ttctcctaga   240
tccgcggcgg attgtgctaa aggtaaaatt gagttttcca agtataatga ggataatacc   300

| | |
|---|---|
| tttactgtga aggtgtcagg aagagaatac tggacgaaca gatggaattt gcagccattg | 360 |
| ttacaaagtg ctcagctgac agggatgact gtaacaatca tatctaatac ctgcagttca | 420 |
| ggctcaggct ttgcccaggt gaagtttaac agatcccctg gttctggtcc tggttctcct | 480 |
| agatccgcgg cggattgtgc taaaggtaaa attgagtttt ccaagtataa tgaggataat | 540 |
| accttactg tgaaggtgtc aggaagagaa tactggacga acagatggaa tttgcagcca | 600 |
| ttgttacaaa gtgctcagct gacagggatg actgtaacaa tcatatctaa tacctgcagt | 660 |
| tcaggctcag gctttgccca ggtgaagttt aacagatccc ctggttctgg tcctggttct | 720 |
| cctagatcct ga | 732 |

```
<210> SEQ ID NO 88
<211> LENGTH: 243
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Ala Ala Asp Cys Ala Lys Gly Lys Ile Glu Phe Ser Lys Tyr Asn Glu
1               5                   10                  15

Asp Asn Thr Phe Thr Val Lys Val Ser Gly Arg Glu Tyr Trp Thr Asn
            20                  25                  30

Arg Trp Asn Leu Gln Pro Leu Leu Gln Ser Ala Gln Leu Thr Gly Met
        35                  40                  45

Thr Val Thr Ile Ile Ser Asn Thr Cys Ser Ser Gly Ser Gly Phe Ala
    50                  55                  60

Gln Val Lys Phe Asn Arg Ser Pro Gly Ser Gly Pro Gly Ser Pro Arg
65                  70                  75                  80

Ser Ala Ala Asp Cys Ala Lys Gly Lys Ile Glu Phe Ser Lys Tyr Asn
                85                  90                  95

Glu Asp Asn Thr Phe Thr Val Lys Val Ser Gly Arg Glu Tyr Trp Thr
            100                 105                 110

Asn Arg Trp Asn Leu Gln Pro Leu Leu Gln Ser Ala Gln Leu Thr Gly
        115                 120                 125

Met Thr Val Thr Ile Ile Ser Asn Thr Cys Ser Ser Gly Ser Gly Phe
    130                 135                 140

Ala Gln Val Lys Phe Asn Arg Ser Pro Gly Ser Gly Pro Gly Ser Pro
145                 150                 155                 160

Arg Ser Ala Ala Asp Cys Ala Lys Gly Lys Ile Glu Phe Ser Lys Tyr
                165                 170                 175

Asn Glu Asp Asn Thr Phe Thr Val Lys Val Ser Gly Arg Glu Tyr Trp
            180                 185                 190

Thr Asn Arg Trp Asn Leu Gln Pro Leu Leu Gln Ser Ala Gln Leu Thr
        195                 200                 205

Gly Met Thr Val Thr Ile Ile Ser Asn Thr Cys Ser Ser Gly Ser Gly
    210                 215                 220

Phe Ala Gln Val Lys Phe Asn Arg Ser Pro Gly Ser Gly Pro Gly Ser
225                 230                 235                 240

Pro Arg Ser

<210> SEQ ID NO 89
<211> LENGTH: 504
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 89

| | | | | | |
|---|---|---|---|---|---|
| gcggcggatt | gtgctaaagg | taaaattgag | ttttccaagt | ataatgagga | taataccttt | 60 |
| actgtgaagg | tgtcaggaag | agaatactgg | acgaacagat | ggaatttgca | gccattgtta | 120 |
| caaagtgctc | agctgacagg | gatgactgta | acaatcatat | ctaatacctg | cagttcaggc | 180 |
| tcaggctttg | cccaggtgaa | gtttaacaga | tcccctggtt | ctggtcctgg | ttctcctaga | 240 |
| tcccctggtt | ccagatctgc | ggcggattgt | gctaaaggta | aaattgagtt | ttccaagtat | 300 |
| aatgaggata | ataccttttac | tgtgaaggtg | tcaggaagag | aatactggac | gaacagatgg | 360 |
| aatttgcagc | cattgttaca | aagtgctcag | ctgacaggga | tgactgtaac | aatcatatct | 420 |
| aatacctgca | gttcaggctc | aggctttgcc | caggtgaagt | ttaacagatc | ccctggttct | 480 |
| ggtcctggtt | ctcctagatc | ttga | | | | 504 |

<210> SEQ ID NO 90
<211> LENGTH: 167
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Ala Ala Asp Cys Ala Lys Gly Lys Ile Glu Phe Ser Lys Tyr Asn Glu
 1               5                  10                  15

Asp Asn Thr Phe Thr Val Lys Val Ser Gly Arg Glu Tyr Trp Thr Asn
             20                  25                  30

Arg Trp Asn Leu Gln Pro Leu Leu Gln Ser Ala Gln Leu Thr Gly Met
         35                  40                  45

Thr Val Thr Ile Ile Ser Asn Thr Cys Ser Ser Gly Ser Gly Phe Ala
     50                  55                  60

Gln Val Lys Phe Asn Arg Ser Pro Gly Ser Gly Pro Gly Ser Pro Arg
 65                  70                  75                  80

Ser Pro Gly Ser Arg Ser Ala Ala Asp Cys Ala Lys Gly Lys Ile Glu
                 85                  90                  95

Phe Ser Lys Tyr Asn Glu Asp Asn Thr Phe Thr Val Lys Val Ser Gly
            100                 105                 110

Arg Glu Tyr Trp Thr Asn Arg Trp Asn Leu Gln Pro Leu Leu Gln Ser
        115                 120                 125

Ala Gln Leu Thr Gly Met Thr Val Thr Ile Ile Ser Asn Thr Cys Ser
    130                 135                 140

Ser Gly Ser Gly Phe Ala Gln Val Lys Phe Asn Arg Ser Pro Gly Ser
145                 150                 155                 160

Gly Pro Gly Ser Pro Arg Ser
                165

<210> SEQ ID NO 91
<211> LENGTH: 519
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 91

```
gcggcggatt gtgctaaagg taaaattgag ttttccaagt ataatgagga taatacctttt     60 actgtgaagg tgtcaggaag agaatactgg acgaacagat ggaatttgca gccattgtta    120
caaagtgctc agctgacagg gatgactgta acaatcatat ctaatacctg cagttcaggc    180
tcaggctttg cccaggtgaa gtttaacaga tcccctggtt ctggtcctgg ttctcctaga    240
tcccctggtt ctggtcctgg ttctcctaga tctgcggcgg attgtgctaa aggtaaaatt    300
gagttttcca gtataatga ggataatacc tttactgtga aggtgtcagg aagagaatac     360
tggacgaaca gatggaattt gcagccattg ttacaaagtg ctcagctgac agggatgact    420
gtaacaatca tatctaatac ctgcagttca ggctcaggct tgcccaggt gaagtttaac    480 agatcccctg gttctggtcc tggttctcct agatcttga                           519
```

<210> SEQ ID NO 92
<211> LENGTH: 172
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

```
Ala Ala Asp Cys Ala Lys Gly Lys Ile Glu Phe Ser Lys Tyr Asn Glu
 1               5                  10                  15

Asp Asn Thr Phe Thr Val Lys Val Ser Gly Arg Glu Tyr Trp Thr Asn
            20                  25                  30

Arg Trp Asn Leu Gln Pro Leu Leu Gln Ser Ala Gln Leu Thr Gly Met
        35                  40                  45

Thr Val Thr Ile Ile Ser Asn Thr Cys Ser Ser Gly Ser Gly Phe Ala
    50                  55                  60

Gln Val Lys Phe Asn Arg Ser Pro Gly Ser Gly Pro Gly Ser Pro Arg
65                  70                  75                  80

Ser Pro Gly Ser Gly Pro Gly Ser Pro Arg Ser Ala Ala Asp Cys Ala
                85                  90                  95

Lys Gly Lys Ile Glu Phe Ser Lys Tyr Asn Glu Asp Asn Thr Phe Thr
            100                 105                 110

Val Lys Val Ser Gly Arg Glu Tyr Trp Thr Asn Arg Trp Asn Leu Gln
        115                 120                 125

Pro Leu Leu Gln Ser Ala Gln Leu Thr Gly Met Thr Val Thr Ile Ile
    130                 135                 140

Ser Asn Thr Cys Ser Ser Gly Ser Gly Phe Ala Gln Val Lys Phe Asn
145                 150                 155                 160

Arg Ser Pro Gly Ser Gly Pro Gly Ser Pro Arg Ser
                165                 170
```

<210> SEQ ID NO 93
<211> LENGTH: 1002
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93

```
accccccaga acatcaccga cctctgcgcc gagagccaca cacccaaat ctacaccctc      60 aacgacaaga ttttcagcta caccgagagc ctcgccggca gagggagat ggccatcatc    120 accttcaaga acggcgccat cttccaggtc gaggtccccg gcagccagca catcgacagc    180
```

```
cagaagaagg ccatcgagag gatgaaggac accctcagga tcgcctacct caccgaggcc    240
aaggtcgaga agctctgcgt ctggaacaac aagaccccc acgccatcgc cgccatcagc    300
atggccaaca gatcccctgg ttctggtcct ggttctccta gatccacccc ccagaacatc    360
accgacctct cgccgagag ccacaacacc caaatctaca ccctcaacga caagattttc    420
agctacaccg agagcctcgc cggcaagagg gagatggcca tcatcacctt caagaacggc    480
gccatcttcc aggtcgaggt ccccggcagc cagcacatcg acagccagaa gaaggccatc    540
gagaggatga aggacaccct caggatcgcc tacctcaccg aggccaaggt cgagaagctc    600
tgcgtctgga acaacaagac cccccacgcc atcgccgcca tcagcatggc caacagatcc    660
cctggttctg gtcctggttc tcctagatcc acccccaga acatcaccga cctctgcgcc    720
gagagccaca cacccaaat ctacaccctc aacgacaaga ttttcagcta caccgagagc    780
ctcgccggca gagggagat ggccatcatc accttcaaga acggcgccat cttccaggtc    840
gaggtccccg gcagccagca catcgacagc cagaagaagg ccatcgagag gatgaaggac    900
accctcagga tcgcctacct caccgaggcc aaggtcgaga agctctgcgt ctggaacaac    960
aagaccccc acgccatcgc cgccatcagc atggccaact ga                      1002
```

<210> SEQ ID NO 94
<211> LENGTH: 333
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 94

```
Thr Pro Gln Asn Ile Thr Asp Leu Cys Ala Glu Ser His Asn Thr Gln
1               5                   10                  15

Ile Tyr Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Ile Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn Arg Ser Pro Gly Ser Gly Pro Gly Ser
            100                 105                 110

Pro Arg Ser Thr Pro Gln Asn Ile Thr Asp Leu Cys Ala Glu Ser His
        115                 120                 125

Asn Thr Gln Ile Tyr Thr Leu Asn Asp Lys Ile Phe Ser Tyr Thr Glu
    130                 135                 140

Ser Leu Ala Gly Lys Arg Glu Met Ala Ile Ile Thr Phe Lys Asn Gly
145                 150                 155                 160

Ala Ile Phe Gln Val Glu Val Pro Gly Ser Gln His Ile Asp Ser Gln
                165                 170                 175

Lys Lys Ala Ile Glu Arg Met Lys Asp Thr Leu Arg Ile Ala Tyr Leu
            180                 185                 190

Thr Glu Ala Lys Val Glu Lys Leu Cys Val Trp Asn Asn Lys Thr Pro
        195                 200                 205

His Ala Ile Ala Ala Ile Ser Met Ala Asn Arg Ser Pro Gly Ser Gly
```

Pro Gly Ser Pro Arg Ser Thr Pro Gln Asn Ile Thr Asp Leu Cys Ala
225                 230                 235                 240

Glu Ser His Asn Thr Gln Ile Tyr Thr Leu Asn Asp Lys Ile Phe Ser
            245                 250                 255

Tyr Thr Glu Ser Leu Ala Gly Lys Arg Glu Met Ala Ile Ile Thr Phe
        260                 265                 270

Lys Asn Gly Ala Ile Phe Gln Val Glu Val Pro Gly Ser Gln His Ile
            275                 280                 285

Asp Ser Gln Lys Lys Ala Ile Glu Arg Met Lys Asp Thr Leu Arg Ile
        290                 295                 300

Ala Tyr Leu Thr Glu Ala Lys Val Glu Lys Leu Cys Val Trp Asn Asn
305                 310                 315                 320

Lys Thr Pro His Ala Ile Ala Ala Ile Ser Met Ala Asn
            325                 330

<210> SEQ ID NO 95
<211> LENGTH: 1038
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
accccccaga acatcaccga cctctgcgcc gagagccaca acacccaaat ctacaccctc        60
aacgacaaga ttttcagcta caccgagagc ctcgccggca gagggagat ggccatcatc       120 accttcaaga acggcgccat cttccaggtc gaggtccccg gcagccagca catcgacagc       180
cagaagaagg ccatcgagag gatgaaggac acccctcagga tcgcctacct caccgaggcc       240
aaggtcgaga agctctgcgt ctggaacaac aagacccccc acgccatcgc cgccatcagc       300
atggccaaca gatcccctgg ttctggtcct ggttctccta gatccacccc ccagaacatc       360
accgacctct gcgccgagag ccacaacacc caaatctaca ccctcaacga caagattttc       420
agctacaccg agagcctcgc cggcaagagg gagatggcca tcatcacctt caagaacggc       480
gccatcttcc aggtcgaggt ccccggcagc cagcacatcg acagccagaa gaaggccatc       540
gagaggatga aggacaccct caggatcgcc tacctcaccg aggccaaggt cgagaagctc       600
tgcgtctgga acaacaagac ccccacgcc atcgccgcca tcagcatggc caacagatcc       660 ctggttctg gtcctggttc tcctagatct accccccaga acatcaccga cctctgcgcc       720
gagagccaca cacccaaat ctacaccctc aacgacaaga ttttcagcta caccgagagc       780
ctcgccggca gagggagat ggccatcatc accttcaaga acggcgccat cttccaggtc       840
gaggtccccg gcagccagca catcgacagc cagaagaagg ccatcgagag gatgaaggac       900
accctcagga tcgcctacct caccgaggcc aaggtcgaga agctctgcgt ctggaacaac       960
aagacccccc acgccatcgc cgccatcagc atggccaaca gatcccctgg ttctggtcct      1020
ggttctccta gatcttga                                                    1038

<210> SEQ ID NO 96
<211> LENGTH: 345
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

```
Thr Pro Gln Asn Ile Thr Asp Leu Cys Ala Glu Ser His Asn Thr Gln
1               5                   10                  15
Ile Tyr Thr Leu Asn Asp Lys Ile Phe Ser Tyr Thr Glu Ser Leu Ala
            20                  25                  30
Gly Lys Arg Glu Met Ala Ile Ile Thr Phe Lys Asn Gly Ala Ile Phe
        35                  40                  45
Gln Val Glu Val Pro Gly Ser Gln His Ile Asp Ser Gln Lys Lys Ala
    50                  55                  60
Ile Glu Arg Met Lys Asp Thr Leu Arg Ile Ala Tyr Leu Thr Glu Ala
65                  70                  75                  80
Lys Val Glu Lys Leu Cys Val Trp Asn Asn Lys Thr Pro His Ala Ile
                85                  90                  95
Ala Ala Ile Ser Met Ala Asn Arg Ser Pro Gly Ser Gly Pro Gly Ser
            100                 105                 110
Pro Arg Ser Thr Pro Gln Asn Ile Thr Asp Leu Cys Ala Glu Ser His
        115                 120                 125
Asn Thr Gln Ile Tyr Thr Leu Asn Asp Lys Ile Phe Ser Tyr Thr Glu
    130                 135                 140
Ser Leu Ala Gly Lys Arg Glu Met Ala Ile Ile Thr Phe Lys Asn Gly
145                 150                 155                 160
Ala Ile Phe Gln Val Glu Val Pro Gly Ser Gln His Ile Asp Ser Gln
                165                 170                 175
Lys Lys Ala Ile Glu Arg Met Lys Asp Thr Leu Arg Ile Ala Tyr Leu
            180                 185                 190
Thr Glu Ala Lys Val Glu Lys Leu Cys Val Trp Asn Asn Lys Thr Pro
        195                 200                 205
His Ala Ile Ala Ala Ile Ser Met Ala Asn Arg Ser Pro Gly Ser Gly
    210                 215                 220
Pro Gly Ser Pro Arg Ser Thr Pro Gln Asn Ile Thr Asp Leu Cys Ala
225                 230                 235                 240
Glu Ser His Asn Thr Gln Ile Tyr Thr Leu Asn Asp Lys Ile Phe Ser
                245                 250                 255
Tyr Thr Glu Ser Leu Ala Gly Lys Arg Glu Met Ala Ile Ile Thr Phe
            260                 265                 270
Lys Asn Gly Ala Ile Phe Gln Val Glu Val Pro Gly Ser Gln His Ile
        275                 280                 285
Asp Ser Gln Lys Lys Ala Ile Glu Arg Met Lys Asp Thr Leu Arg Ile
    290                 295                 300
Ala Tyr Leu Thr Glu Ala Lys Val Glu Lys Leu Cys Val Trp Asn Asn
305                 310                 315                 320
Lys Thr Pro His Ala Ile Ala Ala Ile Ser Met Ala Asn Arg Ser Pro
                325                 330                 335
Gly Ser Gly Pro Gly Ser Pro Arg Ser
            340                 345
```

<210> SEQ ID NO 97
<211> LENGTH: 708
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 97

```
acccccccaga acatcaccga cctctgcgcc gagagccaca acacccaaat ctacaccctc    60
aacgacaaga ttttcagcta caccgagagc ctcgccggca agaggagat ggccatcatc     120 accttcaaga acggcgccat cttccaggtc gaggtccccg gcagccagca catcgacagc    180
cagaagaagg ccatcgagag gatgaaggac accctcagga tcgcctacct caccgaggcc    240
aaggtcgaga agctctgcgt ctggaacaac aagaccccc acgccatcgc cgccatcagc     300
atggccaaca gatcccctgg ttctggtcct ggttctccta gatcccctgg ttccagatct    360 acccccccaga acatcaccga cctctgcgcc gagagccaca acacccaaat ctacaccctc   420
aacgacaaga ttttcagcta caccgagagc ctcgccggca agaggagat ggccatcatc     480 accttcaaga acggcgccat cttccaggtc gaggtccccg gcagccagca catcgacagc    540
cagaagaagg ccatcgagag gatgaaggac accctcagga tcgcctacct caccgaggcc    600
aaggtcgaga agctctgcgt ctggaacaac aagaccccc acgccatcgc cgccatcagc     660
atggccaaca gatcccctgg ttctggtcct ggttctccta gatcttga                 708
```

<210> SEQ ID NO 98
<211> LENGTH: 235
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 98

```
Thr Pro Gln Asn Ile Thr Asp Leu Cys Ala Glu Ser His Asn Thr Gln
1               5                   10                  15

Ile Tyr Thr Leu Asn Asp Lys Ile Phe Ser Tyr Thr Glu Ser Leu Ala
                20                  25                  30

Gly Lys Arg Glu Met Ala Ile Ile Thr Phe Lys Asn Gly Ala Ile Phe
            35                  40                  45

Gln Val Glu Val Pro Gly Ser Gln His Ile Asp Ser Gln Lys Lys Ala
        50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn Arg Ser Pro Gly Ser Gly Pro Gly Ser
            100                 105                 110

Pro Arg Ser Pro Gly Ser Arg Ser Thr Pro Gln Asn Ile Thr Asp Leu
        115                 120                 125

Cys Ala Glu Ser His Asn Thr Gln Ile Tyr Thr Leu Asn Asp Lys Ile
    130                 135                 140

Phe Ser Tyr Thr Glu Ser Leu Ala Gly Lys Arg Glu Met Ala Ile Ile
145                 150                 155                 160

Thr Phe Lys Asn Gly Ala Ile Phe Gln Val Glu Val Pro Gly Ser Gln
                165                 170                 175

His Ile Asp Ser Gln Lys Lys Ala Ile Glu Arg Met Lys Asp Thr Leu
            180                 185                 190

Arg Ile Ala Tyr Leu Thr Glu Ala Lys Val Glu Lys Leu Cys Val Trp
        195                 200                 205

Asn Asn Lys Thr Pro His Ala Ile Ala Ala Ile Ser Met Ala Asn Arg
    210                 215                 220

Ser Pro Gly Ser Gly Pro Gly Ser Pro Arg Ser
225                 230                 235
```

<210> SEQ ID NO 99
<211> LENGTH: 723
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 99

```
acccccaga acatcaccga cctctgcgcc gagagccaca cacccaaat ctacaccctc      60
aacgacaaga ttttcagcta caccgagagc ctcgccggca agagggagat ggccatcatc    120
accttcaaga acggcgccat cttccaggtc gaggtccccg gcagccagca catcgacagc    180
cagaagaagg ccatcgagag gatgaaggac accctcagga tcgcctacct caccgaggcc    240
aaggtcgaga agctctgcgt ctggaacaac aagacccccc acgccatcgc cgccatcagc    300
atggccaaca gatcccctgg ttctggtcct ggttctccta gatcccctgg ttctggtcct    360
ggttctccta gatctacccc ccagaacatc accgacctct cgccgagag ccacaacacc    420
caaatctaca ccctcaacga caagattttc agctacaccg agagcctcgc cggcaagagg    480
gagatggcca tcatcacctt caagaacggc gccatcttcc aggtcgaggt ccccggcagc    540
cagcacatcg acagccagaa gaaggccatc gagaggatga aggacacct caggatcgcc    600
tacctcaccg aggccaaggt cgagaagctc tgcgtctgga acaacaagac cccccacgcc    660
atcgccgcca tcagcatggc caacagatcc cctggttctg gtcctggttc tcctagatct    720
tga                                                                  723
```

<210> SEQ ID NO 100
<211> LENGTH: 240
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 100

```
Thr Pro Gln Asn Ile Thr Asp Leu Cys Ala Glu Ser His Asn Thr Gln
1               5                   10                  15

Ile Tyr Thr Leu Asn Asp Lys Ile Phe Ser Tyr Thr Glu Ser Leu Ala
            20                  25                  30

Gly Lys Arg Glu Met Ala Ile Ile Thr Phe Lys Asn Gly Ala Ile Phe
        35                  40                  45

Gln Val Glu Val Pro Gly Ser Gln His Ile Asp Ser Gln Lys Lys Ala
    50                  55                  60

Ile Glu Arg Met Lys Asp Thr Leu Arg Ile Ala Tyr Leu Thr Glu Ala
65                  70                  75                  80

Lys Val Glu Lys Leu Cys Val Trp Asn Asn Lys Thr Pro His Ala Ile
                85                  90                  95

Ala Ala Ile Ser Met Ala Asn Arg Ser Pro Gly Ser Gly Pro Gly Ser
            100                 105                 110

Pro Arg Ser Pro Gly Ser Gly Pro Gly Ser Pro Arg Ser Thr Pro Gln
        115                 120                 125

Asn Ile Thr Asp Leu Cys Ala Glu Ser His Asn Thr Gln Ile Tyr Thr
    130                 135                 140

Leu Asn Asp Lys Ile Phe Ser Tyr Thr Glu Ser Leu Ala Gly Lys Arg
145                 150                 155                 160
```

Glu Met Ala Ile Ile Thr Phe Lys Asn Gly Ala Ile Phe Gln Val Glu
            165                 170                 175

Val Pro Gly Ser Gln His Ile Asp Ser Gln Lys Lys Ala Ile Glu Arg
        180                 185                 190

Met Lys Asp Thr Leu Arg Ile Ala Tyr Leu Thr Glu Ala Lys Val Glu
    195                 200                 205

Lys Leu Cys Val Trp Asn Asn Lys Thr Pro His Ala Ile Ala Ala Ile
210                 215                 220

Ser Met Ala Asn Arg Ser Pro Gly Ser Gly Pro Gly Ser Pro Arg Ser
225                 230                 235                 240

<210> SEQ ID NO 101
<211> LENGTH: 583
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 101
tatttaactc agtattcaga acaacaaaa gttcttctct acataaaatt ttcctatttt      60
agtgatcagt gaaggaaatc aagaaaaata aatggcggcg gattgtgcta aaggtaaaat    120
tgagttttcc aagtataatg aggataatac ctttactgtg aaggtgtcag gaagagaata    180
ctggacgaac agatggaatt gcagccatt gttacaaagt gctcagctga cagggatgac     240
tgtaacaatc atatctaata cctgcagttc aggctcaggc tttgcccagg tgaagtttaa    300
cagatcccct ggttctggtc ctggttctcc tagatccgcg gcggattgtg ctaaaggtaa    360
aattgagttt ccaagtata atgaggataa tacctttact gtgaaggtgt caggaagaga    420
atactggacg aacagatgga atttgcagcc attgttacaa agtgctcagc tgacagggat    480
gactgtaaca atcatatcta atacctgcag ttcaggctca ggctttgccc aggtgaagtt    540
taacagatcc cctggttctg gtcctggttc tctagatcc tga                      583

<210> SEQ ID NO 102
<211> LENGTH: 682
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 102
tatttaactc agtattcaga acaacaaaa gttcttctct acataaaatt ttcctatttt      60
agtgatcagt gaaggaaatc aagaaaaata aatggggaga atgtcaatac ccatgatggg    120
ttttgtggtg ttatgtctat gggcagtggt agcagaagga tccgcggcgg attgtgctaa    180
aggtaaaatt gagttttcca agtataatga ggataatacc tttactgtga aggtgtcagg    240
aagagaatac tggacgaaca gatggaattt gcagccattg ttacaaagtg ctcagctgac    300
agggatgact gtaacaatca tatctaatac ctgcagttca ggctcaggct ttgcccaggt    360
gaagtttaac agatcccctg gttctggtcc tggttctcct agatcccctg gttccagatc    420
tgcggcggat tgtgctaaag gtaaaattga gttttccaag tataatgagg ataataccct    480
tactgtgaag gtgtcaggaa gagaatactg gacgaacaga tggaatttgc agccattgtt    540
acaaagtgct cagctgacag ggatgactgt aacaatcata tctaatacct gcagttcagg    600
ctcaggcttt gcccaggtga agtttaacag atcccctggt tctggtcctg gttctcctag    660
atctgaacat gatgaattgt ga    682

<210> SEQ ID NO 103
<211> LENGTH: 697
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 103

```
tatttaactc agtattcaga acaacaaaa gttcttctct acataaaatt ttcctatttt    60
agtgatcagt gaaggaaatc aagaaaaata aatggggaga atgtcaatac ccatgatggg   120
ttttgtggtg ttatgtctat gggcagtggt agcagaagga tccgcggcgg attgtgctaa   180
aggtaaaatt gagttttcca agtataatga ggataatacc tttactgtga aggtgtcagg   240
aagagaatac tggacgaaca gatggaattt gcagccattg ttacaaagtg ctcagctgac   300
agggatgact gtaacaatca tatctaatac ctgcagttca ggctcaggct ttgcccaggt   360
gaagtttaac agatcccctg gttctggtcc tggttctcct agatcccctg gttctggtcc   420
tggttctcct agatctgcgg cggattgtgc taaaggtaaa attgagtttt ccaagtataa   480
tgaggataat acctttactg tgaaggtgtc aggaagagaa tactggacga acagatggaa   540
tttgcagcca ttgttacaaa gtgctcagct gacagggatg actgtaacaa tcatatctaa   600
tacctgcagt tcaggctcag gctttgccca ggtgaagttt aacagatccc ctggttctgg   660
tcctggttct cctagatctg aacatgatga attgtga                            697
```

<210> SEQ ID NO 104
<211> LENGTH: 805
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 104

```
tatttaactc agtattcaga acaacaaaa gttcttctct acataaaatt ttcctatttt    60
agtgatcagt gaaggaaatc aagaaaaata aatggcctcc atctcctcct cagccatcgc   120
caccgtcaac cggaccacct ccacccaagc tagcttggca gctccattca ccggcctcaa   180
gtctaacgta gctttcccag ttaccaagaa ggctaacaat gacttttcat ccctacccag   240
caacggtgga agagtacaat gcatgaaggt gtggccacca attgggttga agaagtacga   300
gactcttca tacctagcgg cggattgtgc taaaggtaaa attgagtttt ccaagtataa   360
tgaggataat acctttactg tgaaggtgtc aggaagagaa tactggacga acagatggaa   420
tttgcagcca ttgttacaaa gtgctcagct gacagggatg actgtaacaa tcatatctaa   480
tacctgcagt tcaggctcag gctttgccca ggtgaagttt aacagatccc ctggttctgg   540
tcctggttct cctagatccg cggcggattg tgctaaaggt aaaattgagt tttccaagta   600
taatgaggat aatacccttta ctgtgaaggt gtcaggaaga gaatactgga cgaacagatg   660
gaatttgcag ccattgttac aaagtgctca gctgacaggg atgactgtaa caatcatatc   720
taatacctgc agttcaggct caggctttgc ccaggtgaag tttaacagat cccctggttc   780
tggtcctggt tctcctagat cctga                                         805
```

<210> SEQ ID NO 105
<211> LENGTH: 826

<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 105

```
tatttaactc agtattcaga acaacaaaa gttcttctct acataaaatt ttcctatttt      60
agtgatcagt gaaggaaatc aagaaaaata aatggcggcg gattgtgcta aaggtaaaat    120
tgagttttcc aagtataatg aggataatac ctttactgtg aaggtgtcag gaagagaata   180
ctggacgaac agatggaatt tgcagccatt gttacaaagt gctcagctga cagggatgac   240
tgtaacaatc atatctaata cctgcagttc aggctcaggc tttgcccagg tgaagtttaa   300
cagatcccct ggtctggtc ctggttctcc tagatccgcg cggattgtg ctaaaggtaa    360
aattgagttt tccaagtata tgaggataa tacctttact gtgaaggtgt caggaagaga   420
atactggacg aacagatgga atttgcagcc attgttacaa agtgctcagc tgacagggat   480
gactgtaaca atcatatcta atacctgcag ttcaggctca ggctttgccc aggtgaagtt   540
taacagatcc cctggttctg gtcctggttc tctagatcc gcggcggatt gtgctaaagg   600
taaaattgag ttttccaagt ataatgagga taatacctt actgtgaagg tgtcaggaag   660
agaatactgg acgaacagat ggaatttgca gccattgtta caaagtgctc agctgacagg   720
gatgactgta acaatcatat ctaatacctg cagttcaggc tcaggctttg cccaggtgaa   780
gtttaacaga tccccctggtt ctggtcctgg ttctcctaga tcctga              826
```

<210> SEQ ID NO 106
<211> LENGTH: 910
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 106

```
tatttaactc agtattcaga acaacaaaa gttcttctct acataaaatt ttcctatttt      60
agtgatcagt gaaggaaatc aagaaaaata aatggggaga atgtcaatac ccatgatggg   120
ttttgtggtg ttatgtctat gggcagtggt agcagaagga tccgcggcg attgtgctaa   180
aggtaaaatt gagttttcca agtataatga ggataatacc tttactgtga aggtgtcagg   240
aagagaatac tggacgaaca gatggaattt gcagccattg ttacaaagtg ctcagctgac   300
agggatgact gtaacaatca tatctaatac ctgcagttca ggctcaggct ttgcccaggt   360
gaagtttaac agatcccctg gttctggtcc tggttctcct agatccgcgg cggattgtgc   420
taaaggtaaa attgagtttt ccaagtataa tgaggataat accttactg tgaaggtgtc   480
aggaagagaa tactggacga acagatggaa tttgcagcca ttgttacaaa gtgctcagct   540
gacagggatg actgtaacaa tcatatctaa tacctgcagt tcaggctcag gctttgccca   600
ggtgaagttt aacagatccc ctggttctgg tcctggttct cctagatccg cggcggattg   660
tgctaaaggt aaaattgagt tttccaagta taatgaggat aataccttta ctgtgaaggt   720
gtcaggaaga gaatactgga cgaacagatg gaatttgcag ccattgttac aaagtgctca   780
gctgacaggg atgactgtaa caatcatatc taatacctgc agttcaggct caggctttgc   840
ccaggtgaag tttaacagat cccctggttc tggtcctggt tctcctagat ccgaacatga   900
tgaattgtga                                                           910
```

<210> SEQ ID NO 107
<211> LENGTH: 1048
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 107

```
tatttaactc agtattcaga acaacaaaa gttcttctct acataaaatt ttcctatttt      60
agtgatcagt gaaggaaatc aagaaaaata atggcctcc atctcctcct cagccatcgc    120
caccgtcaac cggaccacct ccacccaagc tagcttggca gctccattca ccggcctcaa   180
gtctaacgta gctttcccag ttaccaagaa ggctaacaat gacttttcat ccctacccag   240
caacggtgga agagtacaat gcatgaaggt gtggccacca attgggttga agaagtacga   300
gactctttca tacctagcgg cggattgtgc taaaggtaaa attgagtttt ccaagtataa   360
tgaggataat acctttactg tgaaggtgtc aggaagagaa tactggacga acagatggaa   420
tttgcagcca ttgttacaaa gtgctcagct gacagggatg actgtaacaa tcatatctaa   480
tacctgcagt tcaggctcag gctttgccca ggtgaagttt aacagatccc ctggttctgg   540
tcctggttct cctagatccg cggcggattg tgctaaaggt aaaattgagt tttccaagta   600
taatgaggat aatacccttta ctgtgaaggt gtcaggaaga gaatactgga cgaacagatg   660
gaatttgcag ccattgttac aaagtgctca gctgacaggg atgactgtaa caatcatatc   720
taatacctgc agttcaggct caggctttgc ccaggtgaag tttaacagat cccctggttc   780
tggtcctggt tctcctagat ccgcggcgga ttgtgctaaa ggtaaaattg agttttccaa   840
gtataatgag gataatacct ttactgtgaa ggtgtcagga agagaatact ggacgaacag   900
atggaatttg cagccattgt tacaaagtgc tcagctgaca gggatgactg taacaatcat   960
atctaatacc tgcagttcag gctcaggctt tgcccaggtg aagtttaaca gatcccctgg  1020
ttctggtcct ggttctccta gatcctga                                    1048
```

<210> SEQ ID NO 108
<211> LENGTH: 787
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 108

```
tatttaactc agtattcaga acaacaaaa gttcttctct acataaaatt ttcctatttt      60
agtgatcagt gaaggaaatc aagaaaaata atgaccccc cagaacatca ccgacctctg    120
cgccgagagc cacaacaccc aaatctacac cctcaacgac aagattttca gctacaccga   180
gagcctcgcc ggcaagaggg agatggccat catcaccttc aagaacggcg ccatcttcca   240
ggtcgaggtc cccggcagcc agcacatcga cagccagaag aaggccatcg agaggatgaa   300
ggacacctc aggatcgcct acctcaccga ggccaaggtc gagaagctct gcgtctggaa   360
caacaagacc cccacgcca tcgccgccat cagcatggcc aacagatccc ctggttctgg   420
tcctggttct cctagatcca cccccagaa catcaccgac ctctgcgccg agagccacaa   480
cacccaaatc taccctca cgacaagat tttcagctac accgagagcc tcgccggcaa   540
gagggagatg gccatcatca ccttcaagaa cggcgccatc ttccaggtcg aggtccccgg   600
cagccagcac atcgacagcc agaagaaggc catcgagagg atgaaggaca ccctcaggat   660
```

```
cgcctacctc accgaggcca aggtcgagaa gctctgcgtc tggaacaaca agaccccca     720 cgccatcgcc gccatcagca tggccaacag atccctggt tctggtcctg gttctcctag     780
atcctga                                                              787
```

<210> SEQ ID NO 109
<211> LENGTH: 886
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 109

```
tatttaactc agtattcaga acaacaaaa gttcttctct acataaaatt ttcctatttt      60
agtgatcagt gaaggaaatc aagaaaaata aatggggaga atgtcaatac ccatgatggg    120
ttttgtggtg ttatgtctat gggcagtggt agcagaagga tccacccccc agaacatcac    180
cgacctctgc gccgagagcc acaaccccca aatctacacc ctcaacgaca gattttcag    240 ctacaccgag agcctcgccg gcaagaggga gatggccatc atcaccttca gaacggcgc    300 catcttccag gtcgaggtcc ccggcagcca gcacatcgac agccagaaga aggccatcga   360
gaggatgaag gacaccctca ggatcgccta cctcaccgag gccaaggtcg agaagctctg   420
cgtctggaac aacaagaccc cccacgccat cgccgccatc agcatggcca acagatcccc    480
tggttctggt cctggttctc ctagatcccc tggttccaga tctacccccc agaacatcac    540
cgacctctgc gccgagagcc acaaccccca aatctacacc ctcaacgaca gattttcag   600 ctacaccgag agcctcgccg gcaagaggga gatggccatc atcaccttca gaacggcgc    660 catcttccag gtcgaggtcc ccggcagcca gcacatcgac agccagaaga aggccatcga   720
gaggatgaag gacaccctca ggatcgccta cctcaccgag gccaaggtcg agaagctctg   780
cgtctggaac aacaagaccc cccacgccat cgccgccatc agcatggcca acagatcccc    840
tggttctggt cctggttctc ctagatctga acatgatgaa ttgtga                  886
```

<210> SEQ ID NO 110
<211> LENGTH: 901
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 110

```
tatttaactc agtattcaga acaacaaaa gttcttctct acataaaatt ttcctatttt      60
agtgatcagt gaaggaaatc aagaaaaata aatggggaga atgtcaatac ccatgatggg    120
ttttgtggtg ttatgtctat gggcagtggt agcagaagga tccacccccc agaacatcac    180
cgacctctgc gccgagagcc acaaccccca aatctacacc ctcaacgaca gattttcag    240 ctacaccgag agcctcgccg gcaagaggga gatggccatc atcaccttca gaacggcgc    300 catcttccag gtcgaggtcc ccggcagcca gcacatcgac agccagaaga aggccatcga   360
gaggatgaag gacaccctca ggatcgccta cctcaccgag gccaaggtcg agaagctctg   420
cgtctggaac aacaagaccc cccacgccat cgccgccatc agcatggcca acagatcccc    480
tggttctggt cctggttctc ctagatcccc tggttctggt cctggttctc ctagatctac    540
cccccagaac atcaccgacc tctgcgccga gagccacaac acccaaatct acaccctcaa    600
```

```
cgacaagatt ttcagctaca ccgagagcct cgccggcaag agggagatgg ccatcatcac    660
cttcaagaac ggcgccatct tccaggtcga ggtccccggc agccagcaca tcgacagcca    720
gaagaaggcc atcgagagga tgaaggacac cctcaggatc gcctacctca ccgaggccaa    780
ggtcgagaag ctctgcgtct ggaacaacaa gaccccccac gccatcgccg ccatcagcat    840
ggccaacaga tcccctggtt ctggtcctgg ttctcctaga tctgaacatg atgaattgtg    900
a                                                                      901
```

<210> SEQ ID NO 111
<211> LENGTH: 1009
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 111

```
tatttaactc agtattcaga aacaacaaaa gttcttctct acataaaatt ttcctatttt     60
agtgatcagt gaaggaaatc aagaaaaata aatggcctcc atctcctcct cagccatcgc    120
caccgtcaac cggaccacct ccacccaagc tagcttggca gctccattca ccggcctcaa    180
gtctaacgta gctttcccag ttaccaagaa ggctaacaat gacttttcat ccctacccag    240
caacggtgga agagtacaat gcatgaaggt gtggccacca attgggttga agaagtacga    300
gactctttca tacctaaccc cccagaacat caccgacctc tgcgccgaga gccacaacac    360
ccaaatctac accctcaacg acaagatttt cagctacacc gagagcctcg ccggcaagag    420
ggagatggcc atcatcacct tcaagaacgg cgccatcttc caggtcgagg tccccggcag    480
ccagcacatc gacagccaga gaaggccat cgagaggatg aaggacaccc tcaggatcgc    540
ctacctcacc gaggccaagg tcgagaagct ctgcgtctgg aacaacaaga ccccccacgc    600
catcgccgcc atcagcatgg ccaacagatc ccctggttct ggtcctggtt ctcctagatc    660
caccccccag aacatcaccg acctctgcgc cgagagccac aacacccaaa tctacaccct    720
caacgacaag attttcagct acaccgagag cctcgccggc aagagggaga tggccatcat    780
caccttcaag aacggcgcca tcttccaggt cgaggtcccc ggcagccagc acatcgacag    840
ccagaagaag gccatcgaga ggatgaagga caccctcagg atcgcctacc tcaccgaggc    900
caaggtcgag aagctctgcg tctggaacaa caagacccccc acgccatcg ccgccatcag    960 catggccaac agatcccctg gttctggtcc tggttctcct agatcctga              1009
```

<210> SEQ ID NO 112
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112

```
tataggatcc cattattttt cttgatttcc                                       30
```

<210> SEQ ID NO 113
<211> LENGTH: 30
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 113
aaatgcatgg cctccatctc ctcctcagcc                                          30

<210> SEQ ID NO 114
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
tttggatcct aggtatgaaa gagtctcgta                                          30
```